US012758567B2

(12) United States Patent
Lian et al.

(10) Patent No.: US 12,758,567 B2
(45) Date of Patent: Oct. 13, 2026

(54) COMPOSITIONS FOR THE TREATMENT OF FIBROSIS

(71) Applicant: Viking Therapeutics, Inc., San Diego, CA (US)

(72) Inventors: Brian Lian, Rancho Santa Fe, CA (US); Hiroko Masamune, San Diego, CA (US); Geoffrey E. Barker, Carlsbad, CA (US)

(73) Assignee: Viking Therapeutics, Inc., San Diego, CA (US)

( * ) Notice: Subject to any disclaimer, the term of this patent is extended or adjusted under 35 U.S.C. 154(b) by 419 days.

(21) Appl. No.: 18/224,387

(22) Filed: Jul. 20, 2023

(65) Prior Publication Data

US 2024/0189332 A1 Jun. 13, 2024

Related U.S. Application Data

(63) Continuation of application No. 16/617,471, filed as application No. PCT/US2018/035909 on Jun. 4, 2018, now Pat. No. 11,707,472.

(Continued)

(51) Int. Cl.
*A61K 31/683* (2006.01)
*A61K 31/662* (2006.01)

(Continued)

(52) U.S. Cl.
CPC .......... *A61K 31/683* (2013.01); *A61K 31/662* (2013.01); *A61K 31/665* (2013.01); *A61P 19/04* (2018.01)

(58) Field of Classification Search
CPC .... A61K 31/19; A61K 31/662; A61K 31/663; A61K 31/664; A61K 31/665;

(Continued)

(56) References Cited

U.S. PATENT DOCUMENTS

| | | | |
|---|---|---|---|
| 3,120,551 | A | 2/1964 | Goldschmidt et al. |
| 3,357,887 | A | 12/1967 | Kagan et al. |

(Continued)

FOREIGN PATENT DOCUMENTS

| | | | |
|---|---|---|---|
| CN | 107469086 | A | 12/2017 |
| CN | 110590898 | | 12/2019 |

(Continued)

OTHER PUBLICATIONS

Rojkind et al. (Abstract , Gastroenterology, vol. 76, (4), 1979, pp. 710-719 (Year: 1979).*

(Continued)

*Primary Examiner* — Savitha M Rao
(74) *Attorney, Agent, or Firm* — Knobbe, Martens Olson & Bear, LLP

(57) ABSTRACT

The present disclosure is directed to methods of treating fibrotic conditions by administration of TRβ agonists. The disclosure provides methods wherein the abnormal deposition of extracellular matrix components, such as collagen, keratin, or elastin, is reduced, either through interaction of TRβ agonists with TGF-β—dependent inflammatory pathways, or by other mechanisms, thereby ameliorating fibrotic symptoms.

17 Claims, 8 Drawing Sheets

Related U.S. Application Data

(60) Provisional application No. 62/515,421, filed on Jun. 5, 2017.

(51) Int. Cl.
*A61K 31/665* (2006.01)
*A61P 19/04* (2006.01)

(58) Field of Classification Search
CPC .... A61K 31/675; A61K 31/683; A61K 45/06; A61K 9/0019
See application file for complete search history.

(56) References Cited

U.S. PATENT DOCUMENTS

| | | | |
|---|---|---|---|
| 4,069,343 | A | 1/1978 | Sellstedt et al. |
| 4,069,347 | A | 1/1978 | McCarthy et al. |
| 4,423,227 | A | 12/1983 | Batz et al. |
| 4,426,453 | A | 1/1984 | Cree et al. |
| 4,554,290 | A | 11/1985 | Boger et al. |
| 4,673,691 | A | 6/1987 | Bachynsky |
| 4,766,121 | A | 8/1988 | Ellis et al. |
| 4,826,876 | A | 5/1989 | Ellis et al. |
| 4,910,305 | A | 3/1990 | Ellis et al. |
| 5,061,798 | A | 10/1991 | Emmett et al. |
| 5,116,828 | A | 5/1992 | Miura et al. |
| 5,158,978 | A | 10/1992 | Rubin |
| 5,232,946 | A | 8/1993 | Hurnaus et al. |
| 5,284,971 | A | 2/1994 | Walker et al. |
| 5,324,522 | A | 6/1994 | Krenning et al. |
| 5,401,772 | A | 3/1995 | Yokoyama et al. |
| 5,519,163 | A | 5/1996 | Gibbs et al. |
| 5,569,674 | A | 10/1996 | Yokoyama et al. |
| 5,571,840 | A | 11/1996 | Mayor et al. |
| 5,627,173 | A | 5/1997 | Graeve et al. |
| 5,654,468 | A | 8/1997 | Yokoyama et al. |
| 5,663,159 | A | 9/1997 | Starrett, Jr. et al. |
| 5,741,803 | A | 4/1998 | Pool et al. |
| 5,753,254 | A | 5/1998 | Khan et al. |
| 5,854,282 | A | 12/1998 | Mellin |
| 5,883,294 | A | 3/1999 | Scanlan et al. |
| 5,922,775 | A | 7/1999 | Kun et al. |
| 5,951,989 | A | 9/1999 | Heymann |
| 6,107,517 | A | 8/2000 | Scanlan et al. |
| 6,117,873 | A | 9/2000 | Acklin et al. |
| 6,147,061 | A | 11/2000 | Reiter |
| 6,194,454 | B1 | 2/2001 | Dow |
| 6,221,911 | B1 | 4/2001 | Lavin et al. |
| 6,236,946 | B1 | 5/2001 | Scanlan et al. |
| 6,266,622 | B1 | 7/2001 | Scanlan et al. |
| 6,326,398 | B1 | 12/2001 | Chiang et al. |
| 6,344,481 | B1 | 2/2002 | Cornelius et al. |
| 6,361,992 | B1 | 3/2002 | Szkudlinski et al. |
| 6,380,255 | B1 | 4/2002 | Lavin et al. |
| 6,414,002 | B1 | 7/2002 | Cheng et al. |
| 6,414,026 | B1 | 7/2002 | Billingham |
| 6,441,015 | B2 | 8/2002 | Aspnes et al. |
| 6,465,687 | B1 | 10/2002 | Li et al. |
| 6,468,755 | B1 | 10/2002 | Shoelson |
| 6,492,424 | B1 | 12/2002 | Apelqvist et al. |
| 6,495,533 | B1 | 12/2002 | Matsui et al. |
| 6,534,676 | B2 | 3/2003 | Markin et al. |
| 6,545,015 | B2 | 4/2003 | Cheng et al. |
| 6,545,018 | B2 | 4/2003 | Chiang et al. |
| 6,555,582 | B1 | 4/2003 | Schwartz et al. |
| 6,566,372 | B1 | 5/2003 | Zhi et al. |
| 6,576,636 | B2 | 6/2003 | Webb et al. |
| 6,608,049 | B2 | 8/2003 | Waltering et al. |
| 6,620,830 | B2 | 9/2003 | Chiang |
| 6,625,201 | B1 | 9/2003 | Wang et al. |
| 6,664,291 | B2 | 12/2003 | Chiang et al. |
| 6,673,815 | B2 | 1/2004 | Devasthale et al. |
| 6,680,340 | B2 | 1/2004 | Cheng et al. |
| 6,689,896 | B2 | 2/2004 | Kukkola |
| 6,716,877 | B2 | 4/2004 | Markin |
| 6,723,744 | B2 | 4/2004 | Aspnes et al. |
| 6,727,271 | B2 | 4/2004 | Cheng et al. |
| 6,747,048 | B2 | 6/2004 | Zhang et al. |
| 6,763,607 | B2 | 7/2004 | Beyernck et al. |
| 6,787,652 | B1 | 9/2004 | Dow et al. |
| 6,794,406 | B2 | 9/2004 | Haning et al. |
| 6,806,381 | B2 | 10/2004 | Chidambaram et al. |
| 6,825,201 | B2 | 11/2004 | Wang et al. |
| 6,831,102 | B2 | 12/2004 | Rangeland |
| 6,852,706 | B1 | 2/2005 | Heber-Katz |
| 6,875,782 | B2 | 4/2005 | Cheng et al. |
| 6,982,348 | B2 | 1/2006 | Kori et al. |
| 7,015,246 | B2 | 3/2006 | Schmeck et al. |
| 7,402,602 | B2 | 7/2008 | Bigg et al. |
| 7,514,419 | B2 | 4/2009 | Erion et al. |
| 7,799,782 | B2 | 9/2010 | Munson et al. |
| 7,829,552 | B2 | 11/2010 | Erion et al. |
| 10,130,643 | B2 | 11/2018 | Cable et al. |
| 10,925,885 | B2 | 2/2021 | Cable et al. |
| 11,202,789 | B2 | 12/2021 | Lian |
| 11,351,183 | B2 | 6/2022 | Lian et al. |
| 11,707,472 | B2 | 7/2023 | Lian et al. |
| 11,707,475 | B2 | 7/2023 | Tunac |
| 11,787,828 | B2 | 10/2023 | Lian et al. |
| 12,102,646 | B2 | 10/2024 | Lian et al. |
| 12,227,533 | B2 | 2/2025 | Lian et al. |
| 2001/0051645 | A1 | 12/2001 | Chiang |
| 2001/0051657 | A1 | 12/2001 | Chiang et al. |
| 2002/0006946 | A1 | 1/2002 | Aspnes et al. |
| 2002/0045751 | A1 | 4/2002 | Kukkola |
| 2002/0049226 | A1 | 4/2002 | Chiang et al. |
| 2002/0107390 | A1 | 8/2002 | Kukkola |
| 2002/0123521 | A1 | 9/2002 | Lavin |
| 2003/0027862 | A1 | 2/2003 | Haning et al. |
| 2003/0040535 | A1 | 2/2003 | Aspnes et al. |
| 2003/0078288 | A1 | 4/2003 | Haning et al. |
| 2003/0078289 | A1 | 4/2003 | Aspnes et al. |
| 2003/0114521 | A1 | 6/2003 | Chiang et al. |
| 2003/0153513 | A1 | 8/2003 | Shiomi et al. |
| 2003/0166724 | A1 | 9/2003 | Rangeland |
| 2004/0029187 | A1 | 2/2004 | Palmer |
| 2004/0039028 | A1 | 2/2004 | Zhang et al. |
| 2004/0077694 | A1 | 4/2004 | Chiang et al. |
| 2004/0097589 | A1 | 5/2004 | Yi-Lin et al. |
| 2004/0110951 | A1 | 6/2004 | Chiang |
| 2004/0116387 | A1 | 6/2004 | Malm et al. |
| 2004/0116391 | A1 | 6/2004 | Piccariello et al. |
| 2004/0142868 | A1 | 7/2004 | Sleeman |
| 2004/0152783 | A1 | 8/2004 | Olon et al. |
| 2004/0157844 | A1 | 8/2004 | Dow et al. |
| 2004/0219218 | A1 | 11/2004 | Martino et al. |
| 2004/0220147 | A1 | 11/2004 | Malm et al. |
| 2005/0004184 | A1 | 1/2005 | Ryono et al. |
| 2005/0038122 | A1 | 2/2005 | Rangeland |
| 2005/0054727 | A1 | 3/2005 | Rangeland |
| 2005/0085541 | A1 | 4/2005 | Shiohara et al. |
| 2006/0046980 | A1 | 3/2006 | Erion et al. |
| 2008/0261913 | A1 | 10/2008 | Sommadossi et al. |
| 2009/0232879 | A1 | 9/2009 | Cable et al. |
| 2010/0081634 | A1 | 4/2010 | Erion et al. |
| 2013/0059781 | A1 | 3/2013 | Kofoed et al. |
| 2015/0045389 | A1 | 2/2015 | Madden et al. |
| 2016/0319548 | A1 | 11/2016 | Shevlin |
| 2017/0105956 | A1 | 4/2017 | Kaminski et al. |
| 2017/0112864 | A1 | 4/2017 | Cable et al. |
| 2017/0348293 | A1 | 12/2017 | Miao et al. |
| 2018/0243263 | A1 | 8/2018 | Jain et al. |
| 2018/0360846 | A1 | 12/2018 | Lefebvre |
| 2019/0255080 | A1 | 8/2019 | Lian et al. |
| 2020/0179412 | A1 | 6/2020 | Lian et al. |
| 2021/0259977 | A1 | 8/2021 | Wu et al. |
| 2021/0308155 | A1 | 10/2021 | Wu et al. |
| 2022/0016136 | A1 | 1/2022 | Lian et al. |
| 2023/0226038 | A1 | 7/2023 | Lian et al. |

(56) References Cited

U.S. PATENT DOCUMENTS

| | | | |
|---|---|---|---|
| 2025/0034183 | A1 | 1/2025 | Barker et al. |
| 2025/0134913 | A1 | 5/2025 | Lian et al. |

FOREIGN PATENT DOCUMENTS

| | | | |
|---|---|---|---|
| CN | 112812114 | | 5/2021 |
| CN | 113024552 | | 6/2021 |
| EP | 080550 | | 1/1994 |
| EP | 1297833 | | 4/2003 |
| EP | 1471049 | | 10/2004 |
| EP | 1666035 | | 6/2006 |
| EP | 1653928 | | 3/2012 |
| JP | 2008-542301 | | 11/2008 |
| JP | 7168660 | B2 | 11/2022 |
| KR | 10-2006-0109926 | | 10/2006 |
| KR | 10-2007-0029196 | | 3/2007 |
| KR | 10-2008-0019297 | | 3/2008 |
| WO | WO 1989/08458 | | 9/1989 |
| WO | WO 1990/08155 | | 7/1990 |
| WO | WO 1990/10636 | | 9/1990 |
| WO | WO 1991/06569 | | 5/1991 |
| WO | WO 1991/11181 | | 8/1991 |
| WO | WO 1995/00135 | | 1/1995 |
| WO | WO 1995/24919 | | 9/1995 |
| WO | WO 1996/05190 | | 2/1996 |
| WO | WO 1996/40048 | | 12/1996 |
| WO | WO 1997/21993 | | 6/1997 |
| WO | WO 1998/07435 | | 2/1998 |
| WO | WO 1998/41216 | | 9/1998 |
| WO | WO 1998/57919 | | 12/1998 |
| WO | WO 1999/00353 | | 1/1999 |
| WO | WO 1999/26966 | | 6/1999 |
| WO | WO 1999/29321 | | 6/1999 |
| WO | WO 1999/38376 | | 8/1999 |
| WO | WO 1999/45016 | | 9/1999 |
| WO | WO 1999/62507 | | 12/1999 |
| WO | WO 2000/00468 | | 1/2000 |
| WO | WO 2000/07972 | | 2/2000 |
| WO | WO 2000/39077 | | 7/2000 |
| WO | WO 2000/51971 | | 9/2000 |
| WO | WO 2000/52015 | | 9/2000 |
| WO | WO 2000/58279 | | 10/2000 |
| WO | WO 2001/13936 | | 3/2001 |
| WO | WO 2001/18013 | | 3/2001 |
| WO | WO 2001/36365 | | 5/2001 |
| WO | WO 2001/60784 | | 8/2001 |
| WO | WO 2001/72692 | | 10/2001 |
| WO | WO 2001/79287 | | 10/2001 |
| WO | WO 2001/94293 | | 12/2001 |
| WO | WO 2001/98256 | | 12/2001 |
| WO | WO 2002/03914 | | 1/2002 |
| WO | WO 2002/04515 | | 1/2002 |
| WO | WO 2002/05834 | | 1/2002 |
| WO | WO 2002/11666 | | 2/2002 |
| WO | WO 2002/26752 | | 4/2002 |
| WO | WO 2002/32408 | | 4/2002 |
| WO | WO 2002/060374 | | 8/2002 |
| WO | WO 2002/062780 | | 8/2002 |
| WO | WO 2002/066017 | | 8/2002 |
| WO | WO 2002/072528 | | 9/2002 |
| WO | WO 2002/079181 | | 10/2002 |
| WO | WO 2002/092550 | | 11/2002 |
| WO | WO 2003/003013 | | 1/2003 |
| WO | WO 2003/015771 | | 2/2003 |
| WO | WO 2003/018515 | | 3/2003 |
| WO | WO 2003/039456 | | 5/2003 |
| WO | WO 2003/061557 | | 7/2003 |
| WO | WO 2003/061567 | | 7/2003 |
| WO | WO 2003/070169 | | 8/2003 |
| WO | WO 2003/075835 | | 9/2003 |
| WO | WO 2003/084915 | | 10/2003 |
| WO | WO 2003/094845 | | 11/2003 |
| WO | WO 2003/099864 | | 12/2003 |
| WO | WO 2003/105760 | | 12/2003 |
| WO | WO 2004/005342 | | 1/2004 |
| WO | WO 2004/007430 | | 1/2004 |
| WO | WO 2004/014318 | | 2/2004 |
| WO | WO 2004/018421 | | 3/2004 |
| WO | WO 2004/026097 | | 4/2004 |
| WO | WO 2004/041208 | | 5/2004 |
| WO | WO 2004/065620 | | 8/2004 |
| WO | WO 2004/066929 | | 8/2004 |
| WO | WO 2004/067482 | | 8/2004 |
| WO | WO 2004/078947 | | 9/2004 |
| WO | WO 2004/091636 | | 10/2004 |
| WO | WO 2004/093799 | | 11/2004 |
| WO | WO 2004/103289 | | 12/2004 |
| WO | WO 2005/009433 | | 2/2005 |
| WO | WO 2005/016862 | | 2/2005 |
| WO | WO 2005/021895 | | 3/2005 |
| WO | WO 2005/028488 | | 3/2005 |
| WO | WO 2005/042556 | | 5/2005 |
| WO | WO 2005/123729 | | 12/2005 |
| WO | WO 2006/128055 | | 11/2006 |
| WO | WO 2006/128056 | | 11/2006 |
| WO | WO 2006/128058 | | 11/2006 |
| WO | WO 2007/009913 | | 1/2007 |
| WO | WO 2007/109605 | | 9/2007 |
| WO | WO 2009/089093 | | 7/2009 |
| WO | WO 2010/074992 | | 7/2010 |
| WO | WO 2010/125565 | | 11/2010 |
| WO | WO 2011/038207 | | 3/2011 |
| WO | WO 2012/087519 | | 6/2012 |
| WO | WO 2013/163675 | | 11/2013 |
| WO | WO 2015/134365 | | 9/2015 |
| WO | WO 2016/097933 | | 6/2016 |
| WO | WO 2016/111971 | | 7/2016 |
| WO | WO 2016/123086 | | 8/2016 |
| WO | WO 2017/148787 | | 9/2017 |
| WO | WO 2017/184811 | | 10/2017 |
| WO | WO 2017/210526 | | 12/2017 |
| WO | WO 2018/053036 | | 3/2018 |
| WO | WO 2018/094265 | | 5/2018 |
| WO | WO 2018/193006 | | 10/2018 |
| WO | WO 2018/226604 | | 12/2018 |
| WO | WO 2019/005816 | | 1/2019 |
| WO | WO 2020/023382 | | 1/2020 |
| WO | WO 2020/033382 | | 2/2020 |
| WO | WO 2020/117962 | | 6/2020 |
| WO | WO 2020/117987 | | 6/2020 |
| WO | WO 2021/190624 | | 9/2021 |
| WO | WO 2021/252392 | | 12/2021 |
| WO | WO 2022/159395 | | 7/2022 |
| WO | WO 2023/280152 | | 1/2023 |
| WO | WO 2023/158607 | | 8/2023 |
| WO | WO 2023/158616 | | 8/2023 |

OTHER PUBLICATIONS

International Search Report and Written Opinion, re PCT Application No. PCT/US2018/035909, mailed Aug. 2, 2018.

International Preliminary Report on Patentability, re PCT Application No. PCT/US2018/035909, issued Dec. 10, 2019.

Alexander et al.,Drugs and Their Structural Motifs, Chapter 1, pp. 28-29, Metabolism, Pharmacokinetics and Toxicity of Functional Groups—Impact of Chemical Building Blocsk on ADMET, 2010.

Alonso-Merino, et al., "Thyroid hormones inhibit TGF-β signaling and attenuate fibrotic responses," PNAS, 2016, vol. 113(24), pp. E3451-E3460.

Amma, L.L., et al., "Distinct Tissue-Specific Roles for Thyroid Hormone Receptors p and al in Regulation of Type 1 Deiodinase Expression," Mot. Endocrinol. 15:467-475, The Endocrine Society (2001).

Anderson, S.N., et al., "Activation of Electrophilic Aromatic Substitution by the Substituent—CH2Co(dmgH)2py. Products of Reaction of Benzylcobaloximes with Halogens in Acetic Acid," J. Chem. Soc. Perkin Trans. II 311-318, Royal Society of Chemistry (1972).

Annett, R.G., et al., "Enzymatically catalysed decarboxylation of P-carboxyaspartic acid (Asa)," Can. J. Chem. 68:886-887, NRC Research Press (1990).

Antons, K.A., et al., "Clinical Perspectives of Starin-Induced Rhabdomyolysis," Am. J. Med. 119:400-409, Excerpta Medica (May 2006).

(56) References Cited

OTHER PUBLICATIONS

Apriletti, J.W., et al., "Molecular and Structural Biology of Thyroid Hormone Receptors," Clin. Exp. Pharmacol. Physiol. 25:S2-SI 1, Blackwell Science Asia (1998).
Archer, S.J., et al., "Hepatitis C Virus NS3 Protease Requires Its NS4A Cofactor Peptide for Optimal Binding of a Boronic Acid Inhibitor as Shown by NMR, "Chem. Biol. 9:79-92, Elsevier Science Ltd (Jan. 2002).
Arnold, S., et al., "3,5-Diiodothyronine binds to subunit Va of cytochrome-c oxidase and abolishes the allosteric inhibition of respiration by ATP," Eur. J. Biochem. 252:325-330, Blackwell Science Ltd (1998).
Arnold, L.A., et al., "Discovery of Small Molecule Inhibitors of the Interaction of the Thyroid Hormone Receptor with Transciptional Coregulators," J. Biol. Chem. 280:43048-43055, American Society for Biochemistry and Molecular Biology (Dec. 2005).
Asahara, Solvent Handbook, with English translation, pp. 47-51 (1985).
Auerbach, B.J., et al., "Comparative Effects of HMG-COA reductase inhibitors on apo B production in the casein-fed rabbit: Atorvastatin versus Lovastatin," Atherosclerosis 115:173-180, Elsevier Science Ltd (1995).
Auberson, Y.P., et al., "N-Phosphonoalkyl-5-Aminomethylquinoxaline-2,3-Diones: In Vivo Active AMPA and NMDA (Glycine) Antagonists," Bioorg. Med. Chem. Lett. 9:249-254, Elsevier Science Ltd (1999).
Austin, Glycogen Storage Disease, The Paitient-Parent Handbook. May 1, 2016.
Ayajiki, K., et al., "Endothelial and Neuronal Functions in Cerebral and Temporal Arteries from Monkeys Fed a High Cholesterol Diet," J. Cardiovascular Pharmacol. 40:456-466, Lippincott Williams & Wilkins (Sep. 2002).
Ayers, et al., "Thyroid hormone analogues: their role in treatment of hyperlipidemia," J. Endocrinol. Diabetes Obes 2(3): 1042. 2014.
Ayers, "Viking's VK2809: A question of safety, not efficacy", Seeking Alpha, Jan. 8, 2018, XP055945971, https://seekingalpha.com/article/4136028-vikings-vk2809-question-of-safety-not-efficacy.
Ball, S.G., et al., "3,5-Diiodo-L-thyronine (T2) has selective thyromimetic effects in vivo and in vitro," J. Mal. Endocrinol. 19:137-147, Society for Endocrinology (1997).
Baxter, J.D., et al., "Structure-Based Design and Synthesis of a Thyroid Homone Receptor (TR) Antagonist," Endocrinology 143:517-524, Endocrine Society (Feb. 2002).
Baxter, J.D., et al., "Selective activation of thyroid hormone signaling pathways by GC-1: a new approach to controlling cholesterol and body weight," Trends Endocrinol. Metab. 15:154-157, Elsevier Science Ltd (May/Jun. 2004).
Beg, M.A.A. and Clark, H.C., "Chemistry of the Trifluoromethyl Group, Part III. Phenyltrifluoromethylphospine and Related Compounds," Can. J. Chem. 39:564-570, NRC Research Press (1962).
Beg, M.A.A. and Clark, H.C., "Chemistry of the Trifluoromethyl Group, Part IV. Diphenyltrifluoromethylphophine and Complex Formation by Phenyltrifluoromethylphospines," Can. J. Chem. 40:283-288, NRC Research Press (1962).
Benayoud, F. and Hammond, G.B., "An expedient synthesis of (a, a-difluoroprop- 2-ynyl) phosphonate esters," Chem. Commun. 1447-1448, Royal Society of Chemistry (1996).
Bhattacharya, "Investigation and management of the hepatic glycogen storage diseases," Transl Pediatrics, vol. 4, No. 3, Jan. 1, 2015.
Bianco, AC., et al., "Biochemistry, Cellular and Molecular Biology, and Physiolgical Roles of the lodothyronine Selenodeiodinases," Endocrine Rev. 23:38-89, The Endocrine Society (Feb. 2002).
Bilger, C., et al., "A Convenient One-Pot Synthesis of Aralkyl Bromides and Iodides by Reductive Halogenation of Aromatic Carbonyl Compounds," Synthesis 902-904, Georg Thieme Verlag (1988).
Blennemann, B., et al., "Tissue-Specific Regulation of Fatty Acid Synthesis by Thyroid Hormone," Endocrinology 130:637-643, The Endocrine Society (1992).
Bobyleva, V., et al., "Decrease in mitochondrial energy coupling by thyroid hormones: a physiological effect rather than a pathological hyperthyroidism consequence," FEBS Lett. 430:409-413, Elsevier Science Ltd (1998).
Bocan, T.M.A., et al., "HMG-CoA reductase and ACAT inhibitors act synergistically to lower plasma cholesterol and limit atherosclerotic lesion development in the cholesterol-fed rabbit," Atherosclerosis 139:21-30, Elsevier Science Ltd. (1998).
Bogardus, J.B. and Higuchi, T., "Kinetics and Mechanism of Hydorolysis of Labile Quaternary Ammonium Derivatives of Tertiary Amines," J. Pharm. Sci. 71:729-735, Wiley (1982).
Bohmer, V. and Vogt, W., "7.(o-Hydroxyphenyl)methylphosphonic acids: Synthesis and Potentiometric Determination of their pKa Values," Helvetica Chimica Acta 76:139-149, Verlag Helvetica Chimica Acta (1993).
Boyd, E.A., et al., "Facile Synthesis of Functionalised Phenylphosphinic Acid Derivatives," Tetrahedron Lett. 37:1651-1654, Elsevier Science Ltd (1996).
Boyd, E.A. and Regan, AC., "Synthesis of y-Keto-substituted Phosphinic Acids from Bis(trimethylsilyl)phosponite and a,P-Unsaturated Ketones," Tetrahedron Lett. 332:813-816, Elsevier Science Ltd (1992).
Boyer et al., "Synthesis and Biological Evaluation of a Series of Liver-Selective Phosphonic Acid Thyroid Hormone Receptor Agonists and Their Prodrugs", J. Med. Chem., 51:7075-7093 (2008).
Briel, D., et al., "3-Amino-5-phenoxythiophenes: Syntheses and Structure-Function Studies of a Novel Class of Inhibitors of Cellular L-Triiodothyronine Uptake," J. Med. Chem. 42:1849-1854, American Chemical Society (1999).
Brooks, et al., "Large Animal Models and New Therapies for Glycogen Storage Disease," J Inherit Metab Dis. May 2015; 38(3): 505-509.
Brown, K., et al., "Accelerator Mass Spectrometry for Biomedical Research," Meth. Enzymol. 402:423-443, Academic Press (Nov. 2005).
Byrn et al., "Pharmaceutical solids: A strategic approach to regulatory considerations", Pharmaceutical Research, vol. 12(7):945-954, (1995).
Cabalska, et al., "Treatment with D-thyroxine of patients with glycogen storage diseases type VI and Via," Materia Medica Polona, Wydawnietwa Handlu Zagranicznego, Warsaw, PL, vol. 19, No. 4, Sep. 30, 1987.
Cable, et al., "Reduction of Hepatic Steatosis in Rats and Mice After Treatment with a Liver-Targeted Thyroid Hormone Receptor Agonist," Hepatology, 2009, vol. 49, pp. 407-417.
Caira, "Crystalline polymorphism or organic compounds", Topics in Current Chemistry, vol. 198:163-208 (1998).
Carvalho, et al., "Glycogen Storage Disease type 1a—a secondary cause for hyperlipidemia: report of five cases," Journal of Diabetes & Metabolic Disorders 2013, 12:25.
Christian, M.S. and Trenton, N.A., "Evaluation of thyroid function in neonatal and adult rats: The neglected endocrine mode of action," Pure Appl. Chem. 75:2055-2068, International Union of Pure and Applied Chemistry (Nov. 2003).
Chou, et al., "Glycogen storage disease type 1 and G6Pase-β deficiency: etiology and therapy," Nat Rev Endocrinol. Dec. 2010; 6(12): 676-688.
Cimmino, M., et al., "Demonstration of in vivo metabolic effects of 3,5-di-iodothyronine," J. Endocrinol. 149:319-325, Society for Endocrinology (1996).
Clutterbuck, P.W. and Cohen, J.B., "The Aryl and Alkyl Sulphonamides," J. Chem. Soc. 123:2507-2515, Royal Society of Chemistry (1923).
Collazo, A-M.G., et al., "Thyroid receptor ligands. Part 5: Novel bicyclic agonist ligands selective for the thyroid hormone recepter B," Bioorg. Med. Chem. Lett. 16:1240-1244, Elsevier Science Ltd. (Mar. 2006).
Columbano, A., et al., "The Thyroid Hormone Receptor-Agonist GC-1 Induces Cell Proliferation in Rat Liver and Pancreas," Endocrinology 147:3211-3218, Endocrine Society (Mar. 2006).
Connolly, et al., "Future Pharmacotherapy for Non-alcoholic Steatohepatitis (NASH): Review of Phase 2 and 3 Trials," Journal of Clinical and Translational Hepatology (2018) vol. 6, pp. 264-275. Epub Jun. 28, 2018.

(56) References Cited

OTHER PUBLICATIONS

Corrie, J.E.T. and Trentham, D.R., "Synthetic, Mechanistic and Photochemical Studies of Phosphate Esters of Substituted Benzoins," J. Chem. Soc. Perkin Trans. 1: 2409-2417, Chemical Society (1992).
Crimmins, M.T., et al., "Asymmetric Aldol Additions: Use of Titanium Tetrachloride and (−)-Sparteine for the Soft Enolization of N-Acyl Oxazolidinones, Oxazolidinethiones, and Thiazolidinethiones," J. Org. Chem. 66:894-902, American Chemical Society (2001).
Croxall, W.J., et al., "Organic Reactions with Boron Fluoride. XI. The Condensation of Propylene with m-andp-Hydroxybenzoic acids," J. Am. Chem. Soc. 57:1549-1551, American Chemical Society (1935).
Danzi, S., et al., "Triiodothyronine-mediated myosin heavy chain gene transcription in the heart," Am. J. Physiol. Heart Circ. Physiol. 284:H2255-H2262, The American Physiological Society (2003).
Database Beilstein, (Online), Beilstein Registry No. 7222862, 6 pages, Beilstein Institute for Organic Chemistry, Frankfurt-Main, DE.
Database Beilstein, (Online), Beilstein Registry No. 7505261, 2 pages, Beilstein Institute for Organic Chemistry, Frankfurt-Main, DE.
Database Beilstein, (Online), Beilstein Registry No. 6636402, 4 pages, Beilstein Institute for Organic Chemistry, Frankfurt-Main, DE.
Database CAplus, Chemical Abstract Service, Columbus Ohio, Enrion, M.D., et al., "Preparation of phosphonic acid-containing liver-selective thyromimetics effective against metabolic diseases," WO 2005-0512986, 16 pages (created Jun. 2005).
Davis, R. and Untch, K.G., "Direct one-step Conversion of Alcohols into Nitriles," J. Org. Chem. 46:2985-2987, American Chemical Society (1981).
Davis, P.J., et al., "Comparison of the mechanisms of nongenomic actions of thyroid hormone and steroid hormones," J. Endocrinol. Invest. 25: 377-388, Italian Society of Endocrinology (Apr. 2002).
De Brabandere, V.I., et al., "Isotope Dilution-Liquid Chromatography/Electrospray Ionization-Tandem Mass Spectrometry for the Determination of Serum Thyroxine as a Potential Reference Method," Rapid Commun. Mass Spectrometry 12:1099-1103, Wiley (1998).
De Sandro, V., et al., "Comparison of the Effects of Propylthiouracil, Amiodarone, Diphenylhydantoin, Phenobarbital, and 3-Methylcholanthrene on Hepatic and Renal T4 Metabolisn and Thyroid Gland Function in Rats," Toxicol. Appl. Pharmacol. 111:263-278, Academic Press (1991).
Demori, I., et al., "3,-5-diiodothyronine Mimics the Effect of Triiodothyronine on Insulin-like growth Factor Binding Protein-4 Expression in Cultured Rat Hepatocytes," Harm. Metab. Res. 36:679-685, Georg Thieme Verlag (Oct. 2004).
Deprele, S. and Montchamp, J.-L., "A novel and convenient preparation of hypophosphite esters," J. Organometallic Chem. 643-644:154-163, Elsevier Science Ltd (Aug. 2002).
Detoisien et al., "A rapid method for screening crystallization conditions and phases of an active pharmaceutical ingredient", Organic Process Research & Development, vol. 13:1338-1342 (2009).
Dhawan, B. and Redmore, D., "1,2-Alkanediol Bis(Dihydrogen Phosphates)," Synth. Commun. 18:327-331, Georg Thieme Verlag (1988).
Dingwall, J.G., et al., "Diethoxymethylphosphonites and Phospinates. Intermediates for the Synthesis of a,P-and y-Aminoalkylphosphonous Acids," Tetrahedron 45:3787-3808, Pergamon Press (1989).
DiStefano III, J.J. and Feng, D., "Comparative Aspects of the Distrubution, Metabolism, and Excretion of Six lodothyronines in the Rat," Endocrinology 123:2514-2525, Endocrine Society (1988).
Docter, R., et al., "Inhibition of Uptake of Thyroid Hormone into Rat Hepatocytes by Preincubation with N-Bromoacety1-3,3 ',5-Triiodothyronine," Endocrinology 123:1520-1525, The Endocrine Society (1988).
Dow, R.L., et al., "Discovery of a Novel Series of 6-Azauracil-Based Thyroid Hormone Receptor Ligands: Potent, TRP Subtype-Selective Thyromimetics," Bioorg. Med. Chem. Lett. 13:379-382, Elsevier Science Ltd (Nov. 2003).
Duntas, "Thyroid Disease and Lipids," Thyroid, vol. 12, No. 4, 2002.
Drechsler, U. and Hanack, M., "An Easy Route from Catechols to Phthalonitriles," Synlett 1207-1208, Georg Thieme Verlag (1998).
Earle, M.J., et al., "The first high yield green route to a pharmaceutical in a room temperature ionic liquid," Green Chem. 2:261-262, Royal Society of Chemistry (2000).
Ebdrup, S., et al., "Structure-activity relationship for aryl and heteroarly boronic acid inhibitors of homone-sensitive lipase," Bioorg. Med. Chem. 13:2305-2312, Elsevier Science Ltd (Jan. 2005).
Edmundson, R.S., et al., "Cyclic Organophosphorus Compounds. Part 23. Configurational Assignments in the 4-Phenyl-l , 3,2A.5-dioxaphosphorinane Series. X-Ray Molecular Structure of cis-2-Benzylamino-4-phenyl-1,3,2-dioxaphosphorinane 2-Oxide," J. Chem. Res. Synop. 5:122-123, Science Reviews, Ltd. (1989).
Edwards, M.L., et al., "Difluoromethyldiphenylphosphine oxide. A new reagent for conversion of carbonyl compounds to 1,1-difluoroolefins," Tetrahedron Lett. 31:5571-5574, Elsevier Science Ltd (1990).
Eisch, J.J., et al., "Rearrangement and Cleavage of [(Aryloxy)methyl]silanes by Organolithium Reagents: Conversion of Phenols into Benzylic alcohols," J. Org. Chem. 47:5051-5056, American Chemical Society (1982).
Ekins, R., "Validity of Analog Free Thyroxin Immunoassays" Clin. Chem. 33:2137-2152, American Association For Clinical Chemistry (1987).
Endres, et al., "D-Thyroxine Treatment in Glycogen Storage Disease Type Via," Pediatric Research, vol. 18, No. 8, Aug. 1, 1984.
Erion, M.D., et al., "Design, Synthesis, and Characterization of a Series of Cytochrome P450 3A-Activated Prodrugs (HepDirect Prodrugs) Useful for Targeting Phosph(on)ate-Based Drugs to the Liver," J. Am. Chem. Soc. 126:5154-5163, American Chemical Society (Apr. 2004).
Erion, M.D., et al., "Liver-Targeted Drug Delivery Using HepDirect Prodrugs," J. Pharmacol. Exper. Ther. 312:554-560, American Society for Pharmacology and Experimental Therapeutics (Feb. 2005).
Erion, et al., "Targeting thyroid hormone receptor-agonists to the liver reduces cholesterol and triglycerides and improves the therapeutic index," PNAS, Sep. 25, 2007, vol. 104, No. 39.
Fabiano, E., et al., "A Simple Conversion of Alcohols into Amines," Synthesis 190-192, Georg Thieme Verlag (1987).
Faergemann, J., et al., "Dose-Response Effects of Tri-iodothyroacetic Acid (Triac) and other Thyroid Hormone Analogues on Glucocorticoid-Induced Skin Atrophy in the Haired Mouse," Acta Derm. Venereal. 82:179-183, Society for the Publication of Acta Dermato-Venereologica (Mar. 2002).
Farquhar, D., et al., "Biologically-Cleavable Phosphate Protective Groups: 4-Acyloxy-1,3,2-Dioxaphosphorinanes as Neutral Latent Precursors of Dianionic Phosphates," Tetrahedron Lett. 36:655-658, Elsevier Science Ltd. (1995).
Feinstein, S., et al., "Submitral Atheromatous Lesions in Monkey and Man", Clin. Cardiol. 6:109-115, John Wiley & Sons, Inc. (1983).
Feng, W., et al., "Hormone-Dependent Coactivator Binding to a Hydrophobic Cleft on Nuclear Receptors," Science 280:1747-1749, American Association for the Advancement of Science (1998).
Field, L.D. and Wilkinson, M.P., "A new Synthesis of 1,2-Bis(Bis(Trifluoromethyl)Phosphino)ethane," Tetrahedron Lett. 33:7601-7604, Elsevier Science Ltd (1992).
Fieser, L.F. andArdao, M.I., "Investigation of the Chemical Nature of Gonyleptidine," J. Am. Chem. Soc. 78:774-781, American Chemical Society (1956).
Fiorucci et al., "Future trends in the treament of non-alcoholic steatohepatitis", Pharmacological Research, vol. 134(17):289-298 (2018).
Fleischmann, K., et al., "Synthesis of HR 916 B: The First Technically Feasible Route to the 1-(Pivaloyloxy)ethyl Esters of Cephalosporins," Liebigs Ann. 1735-1741, Verlag Chemie (1996).
Fong, T.-L., et al., "Hyperthyroidism and Hepatic Dysfunction," J. Clin. Gastroenterol. 14:240-244, Raven Press (1992).

(56) References Cited

OTHER PUBLICATIONS

Freitas, F.R.S., et al., "Spared bone mass in rats treated with thyroid hormone receptor TRf3-selective compound GC-1," Am. J. Physiol. Endocrinol. Metab. 285:EI 135-EI 141, American Physiological Society (Sep. 2003).
Freitas, F.R.S., et al.,"The Thyroid Hormone Receptor f3-Specific Agonist GC-1 Selectivity Affects the Bone Development of Hypothyroid Rats," J. Bone Mineral Res. 20:294-304, American Society for Bone and Mineral Research (Nov. 2004).
Froestl, W., et al., "Phosphinic Acid Analogues of GABA. I. New Potent and Selective GABAB Agonists," J. Med. Chem. 38:3297-3312, American Chemical Society (1995).
Froestl, W., et al., "Phosphinic Acid Analogues of GABA. 2. Selective, Orally Active GABAB Antagonists," J. Med. Chem. 38:3313-3331, American Chemical Society (1995).
Fujitaki, et al., "Preclinical Pharmacokinetics of a HepDirect Prodrug of a Novel Phosphonate-Containing Thyroid Hormone Receptor Agonist," The American Society for Pharmacology and Experimental Therapeutics, vol. 36, No. 11, 2008.
Gallagher, M. J. and Honegger, H., "Organophosphorus Intermediates. VI. The Acid-Catalysed Reaction of Trialkyl Orthoformates with Phosphinic Acid," Aust. J. Chem. 33:287-294, Commonwealth Scientific And Industrial Research Organization (1980).
Garibaldi, et al. "Destrothyroxine treatment of phosphorylase-kinase deficiency glycogenosis in four boys," Helvetica Paediatrica Acta, Schwabe, Basel, CH, vol. 33, No. 4-5, Oct. 31, 1978.
Gilman, H. and Calloway, N_O_, "Super-Aromatic Properties ofFuran. II. The Friedel-Crafts Reaction," J. Am. Chem. Soc. 55:4197-4205, American Chemical Society (1933).
Goglia, F., et al., "In Vitro binding of 3,5-di-iodo-L-thyronine to rat liver mitochondria," J. Mo!. Endocrinol. 13: 275-282, Society for Endocrinology (1994).
Goglia, F., "Biological Effects of 3,5-Diiodothyronine (T2) ," Biochemistry (Moscow) 70:164-172, Pleiades Publishing, Inc. (Feb. 2005).
Goglia, F., et al., "Interaction of diiodothyronines with isolated cytochrome c oxidase," FEBS Lett. 346:295-298, Elsevier Science Ltd. (1994).
Goodrich, P., et al., "Kinetic Study of the Metal Triflate Catalyzed Benzoylation of Anisole in an Ionic Liquid," Ind. Eng. Chem. Res. 45:6640-6647, American Chemical Society (Sep. 2006).
Goswami, A., et al., "Inhibition by coumadin anticoagulants of enzymatic outer ring monodeiodination of iodothyronines," Biochem. Biophys. Res. Commun. 104:1231-1238, Academic Press (1982).
Goya, R.G., et al., "Effects of Growth Hormone and Thyroxine on Thymulin Secretion in Aging Rats," Neuroendocrinology 58:338-343, S. Karger AG, Basel (1993).
Greco, M.N., et al., "Discovery of Potent, Selective, Orally Active, Nonpeptide Inhibitors of Human Mast Cell Chymase," J. Med. Chem. 50:1727-1730, American Chemical Society (Mar. 2007).
Gregory, R.B. and Berry, M.N., "On the thyroid hormone-induced increase in respiratory capacity of isolated rat hepatocytes," Biochim. Biophys. Acta I 098:6 I-67, Elsevier Science Ltd. (1991).
Gronemeyer, H., et al., "Principles for Modulation of the Nuclear Receptor Superfamily" Nature Reviews, Drug Discovery 3:950-964, Nature Publishing Group (Nov. 2004).
Grover, G.J., et al., "Development of the Thyroid Homone Receptor P-Subtype Agonist KB-141: A Strategy for Body Weight Reduction and Lipid Lowering with Minimal Cardiac Side Effects," Cardiovascular Drug Rev. 23:133-148, Blackwell Publishing (Nov. 2005).
Grover, G.J., et al., "Selective thyroid hormone receptor-P activation: A strategy for reduction of weight, cholesterol, and lipoprotein (a) with reduced cardiovascular liability," PNAS J00:I0067-10072, National Academy of Sciences (Aug. 2003).
Grundy, et al., "Implications of Recent Clinical Trials for the National cholesterol Education Program Adult Treatment Panel III Guidelines," Circulation. 2004;110:227-239; downloaded from http://circ.ahajournals.org/.
Guernik, S., et al., "A novel system consisting of Rh-DuPHOS and ionic liquid for asymmetric hydrogenations," Chem. Commun. 2314-2315, Royal Society of Chemistry (2001).
Hadvary, P. and Weller, T., "202. Conformationally Restricted Analogs of Platelet-Activating Factor (PAP)," Helvetica ChimicaActa 69:1862-1871, Verlag Helvetica Chimica Acta (1986).
Hansen, et al., "Mouse models of nonalcoholic steaohepatitis in preclinical drug development," Drug Discovery Today, vol. 22, No. 11, Nov. 2017.
Hashimoto, A., et al., "Design and synthesis of complementing ligands for mutant thyroid hormone receptor TRP(R320H): a tailor-made approach toward the treatment of resistance to thyroid hormone," Bioorg. Med. Chem. 13:3627-3639, Elsevier Science Ltd (Jun. 2005).
Haugen, et al., "Drugs That Suppress TSH or Cause Central Hypothyroidism," Best Pract Res Clin endocrinol. Metab. Dec. 2009; 23(6): 793-800.
Hayakawa, Y., et al., "A General Approach to Nucleoside 3'- and 5'-Monophosphates," Tetrahedron Lett. 28:2259-2262, Elsevier Science Ltd. (1987).
Hedfors, A., et al., "Thyroid Receptor Ligands. 3. Design and Synthesis of 3,5-Dihalo-4-alkoxyphenylalkanoic Acids as Indirect Antagonistis of the Thyroid Hormone Receptor," J. Med. Chem. 48:3114-3117, American Chemical Society (May 2005).
Heimberg, M., et al., "Plasma Lipoproteins and Regulation of Heptic Metabolism of Fatty Acids in Altered Thyroid States," Endocrine Rev. 6:590-607, Endocrine Society (1985).
Hennemann, G., et al., "Carrier-Mediated Transport of Thyroid Hormone into Rat Hepatocytes is Rate-Limiting in Total Cellular Uptake and Metabolism," Endocrinology 119:1870-1872, Endocrine Society (1986).
Hennemann, G., "Notes on the History of Cellular Uptake and Deiodination of Thyroid Hormone," Thyroid 15:753-756, Mary Ann Liebert Publishers (Aug. 2005).
Hepatology, Oct. 2018, vol. 68(1) Supp. 1, p. 1448A, Abstract No. LB-4, Embase (online), dated searched Oct. 24, 2023, retrieved from STN, Accession No. 0053280282.
Hilfiker et al., "Polymorphism in the pharmaceutical industry", XP002528052: 1-19 (2006).
Hirayama, Organic Compound Crystal Preparation Handbook—Principles and Know-How, Maruzen Co., Ltd. Jul. 25, 2008, pp. 57-84, with English translation.
Holt, "Thyroxine Therapy in Glycogen-Storage Disease," Nutrition Reviews, vol. 14, No. 7, Jul. 27, 1956.
Holy, A, "Phosphonomethoxyalkyl Analogs of Nucleotides," Curr. Pharm. Des. 9:2567-2592, Bentham Science Publishers (Dec. 2003).
Hopper et al., 1999, CAS: 130:332269.
Horst, C., et al., "3,5-Di-iodo-L-thyronine suppresses TSH in rats in vivo and in rat pituitary fragments in vitro," J. Endocrinol. 145:291-297, Society for Endocrinology (1995).
Horst, C., et al., "Rapid Stimulation of hepatic oxygen consumption by 3,5-di-iodo-L-thyronine," Biochem. J. 261:945-950, Portland Press (1989).
Howarth, J., et al., "Sodium Borohydride Reduction of Aldehydes and Ketones in the Recyclable lonic Liquid [BMIM]PF 6," Synth. Commun. 31:2935-2938, Taylor & Francis (2001).
Huddleston, J.G., et al., "Characterization and comparison of hydrophilic and hydrophobic room temperature ionic liquids incorporating the imidazolium cation," Green Chem. 3:156-164, Royal Society of Chemistry (2001).
Hum, G., et al., "Synthesis of [Difluoro-(3-alkenylphenyl)-methyl]-phosphonic Acids on Non-crosslinked Polystyrene and Their Evaluation as Inhibitors of PTPIB," Bioorg. Med. Chem. Lett. 12:3471-3474, Elsevier Science Ltd (Aug. 2002).
Hume, J.R., et al., "Anion Transport in Heart," Physiol. Rev. 80:31-81, The American Physiological Society (2000).
Hunter, D.H., et al., "Crown ether catalysis of decarboxylation and decarbalkoxylation of j3-keto acids and malonates: a synthetic application," Can. J. Chem. 58:2271-2277, NRC Research Press (1980).
Ibrahini et al., 2000, CAS: 133:14000.
Ichikawa, K., et al., "Mechanism ofliver-selective thyromimetic activity of SK&F L-94901: evidence for the presence of a cell-

(56) References Cited

OTHER PUBLICATIONS type-specific nuclear iodothyronine transport process," J Endocrinol. 165:391-397, Society for Endocrinology (2000).
Ing, H.R., "The Pharmacology of Homologous Series," Fortschritte der Arzneimittelforschung. Progress in drug research. Progres des recherches pharmaceutiques 20:306-309, Birkhauser Verlag (1964).
Iyer, S. and Liebeskind, L.S., "Regiospecific Synthesis of 2-Methoxy-3-methyl-1,4-benzoquinones fromMaleoylcobalt Complexes andAlkynes via Lewis Acid Catalysis. A Highly Convergent Route to Isoquinoline Quinones," J Am. Chem. Soc. 109:2759-2770, American Chemical Society (1987).
Jain, M.R., et al., "Dual PPARα/γ agonist saroglitazar improves liver histopathology and biochemistry in experimental NASH models", Liver International, (2018) vol. 38, pp. 1084-1094. Epub Dec. 14, 2017.
Jakobsson, T., et al., "Potential Role of Thyroid Receptor β Agonists in the Treatment of Hyperlipidemia", Drugs (2017) vol. 77, pp. 1613-1621.
Jiang et al., "Structural basis of tropifexor as a potent and selective agonist of farnesoid X receptor", Biochemical Biophysical Research Communications, vol. 534:1047-1052 (2021).
Jepson, E.M., "Thyroxine analogues as hypocholesterolemic agents," Am. Heart J 67:422-424, Mosby (1964).
Johnson, E.O., et al., "Experimentally-induced hyperthyroidism is associated with activation of the rat hypothalamic-pituitay-adrenal axis," Eur. J Endocrinol. 153:177-185, BioScientifica Ltd (Jul. 2005).
Jones, P.B. and Porter, N.A., "2-Aroylbenzoyl Serine Proteases: Photoreversible Inhibtion or Photoaffinity Labeling?," J Am. Chem. Soc. 121:2753-2761, American Chemical Society (1999).
Jorgensen, E.C., "Thyroid Hormones and Analogs. II. Structure-Activity Relationships," in: Hormonal Proteins and Peptides, Li, C.H., eds., Academic Press, New York, NY, pp. 107-204 (1978).
Jorgensen, E.C., "Thyroid Hormones and Analogs. I. Synthesis, Physical Properties and Theoretical Calculations," in: Hormonal Proteins and Peptides, Li, C.H., eds., Academic Press, New York, NY, pp. 56-105 (1978).
Jorgensen, E.C. and Murray, W.J., "Thyroxine Analogs. 22. Thyromimetic Activity of Halogen-Free Derivatives of 3,5-Dimethyl-L-Thyronine, "J Med. Chem. 17:434-439 (1974).
Kadenbach, B., et al., "Mitochondrial Energy Metabolsim is Regulated via Nuclear-Coded Subunits of Cytochrome C Oxidase," Free Radical Biol. Med. 29:211-221, Elsevier Science Ltd (2000).
Kazemifard, A.G., et al., "Identification and quantitation of sodium-thyroxine and its degradation products by LC using electrochemical and MS detection," J Pharm. Biomed. Anal. 25:697-71 I, Elsevier Science Ltd. (2001).
Kennedy, J.A., et al., "Influence oflmiprarnine on the Hypothalamic/Pituitary/Thyroid Axis of the Rat," Metabolism 46:1429-1434, W.B. Saunders (1997).
Kennedy, J.F, et al., "Isolation of thyroxine-binding globulin (TBG) by immunoadsorption chromatography: some physical and immunochemical characteristics of TBG," Clinica Chimica Acta 129:251-261, Elsevier Science Ltd (1983).
Kido et al., "Current status of hepatic glycogen storage disease in Japan: clinical manifestations, treatments and long-term outcomes," Joural of Human Genetics (2013) 58, 285-292.
Kishnani, et al., "Diagnosis and management of glycogen storage disease type I: a practice guideline of the American College of Medical Genetics and Genomics," Genetics in Medicine, submitted Aug. 12, 2014.
Knolker, H-J. and Filali, S., "Transition Metal Complexes in Organic Synthesis, Part 69. Total Synthesis of theAmaryllidaceae Alkaloids Anhydrolycorinone and Hippadine Using Iron-and Palladium-Mediated Coupling Reactions," Synlett 1752-1754, Georg Thieme Verlag (Jun. 2003).
Kobayashi, H., et al., "Organization ofNucleosides Supported by Boronic-Acid-Appended Poly(L-lysine): Creation of a Novel RNA Mimic," Bull. Chem. Soc. Jpn. 74:1311-1317, The Chemical Society of Japan (2001).
Koehler, K., et al., "Thyroid Receptor Ligands. 6. A High Affinity "Direct Antagonist" Selective for the Thyroid Hormone Receptor," J. Med. Chem. 49:6635-6637, American Chemical Society (Oct. 2006).
Koerner, D., et al., "Binding of Selected Iodothyronine Analogues to Receptor Sites of Isolated Rat Hepatic Nuclei," J. Biol. Chem. 250:6417-6423, American Society for Biochemistry and Molecular Biology (1975).
Koulischer, "Glycogen-Storage Disease : A Study on the Effect of Sodium/-Thyroxine and Glucagon," AMA Journal of Diseases of Children, vol. 91, No. 2, Feb. 1, 1956.
Kowalik et al., "Thyroid hormones, thyromimetics and their metabolites in the treatment of liver disease", Frontiers in Endocrinology, vol. 9:1-11, (Jul. 10, 2018).
Krause, B.R., et al., "Opposite effects of beza:fibrate and gemfibrozil in both normal and hypertriglyceridemic rats," Atherosclerosis 127:91-101, Elsevier Science Ltd (1996).
Kvetny, J., "3,5-T2 Stimulates Oxygen Consumption, But Not Glucose Uptake in Human Mononuclear Blood Cells," Horm. Metab. Res. 24:322-325, Georg Thieme Verlag (1992).
Lacoste, AM., et al., "Research Regarding Aminoalkylphosphonic Acids. II.—Iodine Derivatives of the Phosphonic Analog of Tyrosine," Bull. Soc. Chim. Biol. 49:1827-1835, Masson Et Cie (1967).
Lacoste, A.-M., et al., "Biochemistry—Synthesis and biological properties of the phosphonic analog of thyroxine," C.R. Acad. Sci. Paris 267:1890-1892, Gauthier Villars Editeur (1968).
Lacoste, A .- M., et al., "Endrocrinology. Action of the phosphonic analog of thyroxine on post-embryonic development of the tadpole of Rana dalmatina Bon," Biol. Soc. Bordeaux 1684-1689 (1967).
Lanni, A., et al., "Specific Binding sites for 3,3'-diiodo-L-thyronine (3,3'-T2) in rat liver mitochondria," FEES Lett. 351:237-240, Elsevier Science Ltd (1994).
Lanni, A., et al., "Effect of 3,3'-di-iodothyronine and 3,5-di-iodothyronine on rat liver mitochondria," J. Endocrinol. 136:59-64, Society for Endocrinology (1993).
Lanni, A., et al., "Effect of 3,3'-diiodothyronine and 3,5-diiodothyronine on rat liver oxidative capacity," Mol. Cell. Endocrinol. 86:143-148, Elsevier Scientific Publishers Ireland (1992).
Lanni, A., et al., "Rapid stimulation in vitro ofrat liver cytochrome oxidase activity by 3,5-diiodo-l-thyronine and by 3,3'-diiodo-L-thyronine," Mol. Cell. Endocrinol. 99:89-94, Elsevier Science Ltd (1994).
Lanni, A., et al., "Expression of uncoupling protein-3 and mitochondrial activity in the transition from hypothyroid to hyperthyroid state in rat skeletal muscle," FEBS Lett. 444:250-254, Elsevier Science Ltd. (1999).
Lanni, A., et al., "Calorigenic effect of diiodothyronines in the rat," J. Physiol. 494:831-837, Blackwell Publishing (1996).
Laskorin, B.N., et al., "Preparation and Investigation of the Steric Structure of Sterically Hindered a-oxo Phosphoryl Compounds," Zhurnal Obshchei Khimii 44:1716-1720, RossiiskayaAkademiya Nauk (1974).
Lee, S.-G., et al., "Microwave-assisted Kabachnik-Fields Reaction in Ionic Liquid," Bull. Korean Chem. Soc. 23:667-668, The Korean Chemical Society (Mar. 2002).
Lee, Y.-P., et al., "Effects of Thyroid Hormones on the Guinea Pig," Endocrinology 86:241-250, The Endocrine Society (1970).
Leonard, J.L. and Rosenberg, I.N., "Iodothyronine 5'-Deiodinase from Rat Kidney: Substrate Specificity and the 5'-Deiodination of Reverse Triiodothrvonine," Endocrinolof!V 107:1376-1383, The Endocrine Society (1980).
Leonard, J.L. and Rosenberg, I.N., "Thyroxine 5'-Deiodinase Activity of Rat Kidney: Observations on Activation by Thiols and Inhibition by Propylthiouracil," Endocrinology 103:2137-2144, The Endocrine Society (1978).
Lewis, D.S., "Effects of dietary cholestrol on adipose tissue lipoprotein lipase in the baboon," Biochim. Biophys. Acta 879:44-50, Elsevier Science Ltd (1986).
Li, Y.-L., et al., "Thyroid receptor ligands. Part 4: 4'-amido bioisosteric ligands selective for the thyroid hormone receptor beta," Bioorg. Med. Chem. Lett. 16:884-886, Elsevier Science Ltd (Feb. 2006).

(56) References Cited

OTHER PUBLICATIONS

Lian, B., "Evaluation of the Thyroid Receptor Agonist VK2809 on Liver Disease in DIO-NASH Mice,", Hepatology, Oct. 2017, vol. 66, No. Suppl. 1, Sp. Iss. SI, p. 1038A.
Liddle, C., et al., "Separate and Interactive Regulation of Cytochrome P450 3A4 by Triiodothyronine, Dexamethasone, and Growth Hormone in Cultured Hepatocytes," J. Clin. Endocrinol. Metab. 83:2411-2416, The Endocrine Society (1998).
Lin, C.-C., et al., Pharmacokinetics of Pradefovir and PMEA in Healthy Volunteers After Oral Dosing of Pradefovir,11 J Clin. Pharmacol. 45:1250-1258, Sage Science Press (Nov. 2005).
Linsel-Nitschke, P. and Tall, AR., "HDL as a Target in the Treatment of Atherosclerotic Cardiovascular Disease," Nature Reviews, Drug Discovery 4:193-205, Nature Publishing Group (Mar. 2005).
Liotta, D., et al., "A Simple, Inexpensive Procedure for the Large-Scale Production of Alkyl Quinones," J Org. Chem. 48:2932-2933, American Chemical Society (1983).
Lombardi, A., et al., "Characterization of the binding of 3, 3'-di-iodo-L-thyronine to rate liver mitochondria," J Endocrinol. 154:119-124, Society for Endocrinology (1997).
Lombardi, A., et al., "Effect of 3,5-di-iodo-L-thyronine on the mitochondrial energy-transduction apparatus," Biochem. J 330:521-526, Portland Press (1998).
Lonsdale, et al., "Normalization of Hepatic Phosphorylase Kinase Activity and Glycogen Concentration in Glycogen Storage Diseas Type IX During Treatment with Sodium D Thyroxine," American Journal of Human Genetics; Annual Meeting of the American Society of Human Genetics, vol. 29, No. 6, Nov. 1, 1977.
Lukashev, N.V., et al., "Palladium-Catalyzed Cross-Coupling Reactions of Organocopper Derivatives of Methylphosphonic Esters and Amides with Aryl and Hetaryl Iodides," Russian J. Gen. Chem. 71:172-178, Kluwer Academic Publishers (2001).
Mackenzie, P.I., et al., "Regulation of UDP Glucuronosyltransferase Genes," Curr. Drug Metab. 4:249-257, Bentham Science Publishers (Jun. 2003).
Madrigal-Matute, et al., "Regulation of Liver Metabolism by Autophagy," Reviews in Basic and Clinical Gastroenterology and Hepatology, Gastroenterology 2016 150:328-339.
Mains, R.E. and Eipper, B.A., "Tissue Culture of Primary Rat Anterior Pituitary Cells" in Regulatory Peptides: From Molecular Biology to Function, Costa, E., Trabucchi, M., eds., Raven Press, New York City, NY, pp. 1-8 (1982).
Makinen, M.W. and Lee, C.-P., "Biochemical Studies of Skeletal Muscle Mitochondria: I. Microanalysis of Cytochrome Content, Oxidative and Phosphorylative Activities of Mammalian Skeletal Muscle Mitochondria," Arch. Biochem. Biophys. 126:75-82, Academic Press (1968).
Malevannaya, R.A., et al., "(Dialkoxyphosphinyl) Acetic Acids and Some of Their Analogs," Zhurnal Obshchei Khimii 41:1426-1434, Rossiiskaya Akademiya Nauk (1971).
Marcus et al., "Alternate-day dosing with statins", The American Journal of Medicine, vol. 126:99-104 (2013).
Marcune, B.F., et al., "Selective displacement of aryl fluorides with hydroquinone: synthesis of 4-phenoxyphenols" Tetrahedron Lett. 46:7823-7826, Elsevier Science Ltd (Nov. 2005).
Marimuthu, A., et al., "TR Surfaces and Conformations Required to Bind Nuclear Receptor Corepressor" Mal. Endocrinol. 16:271-286, The Endocrine Society (Feb. 2002).
Matsui, T., et al., "Discovery of Novel Phosphonic Acid Derivatives as New Chemical Leads for Inhibitors of TNF-a Production," Bioorg. Med. Chem. 10:3807-3815, Elsevier Science Ltd (Aug. 2002).
McClain, R.M., "Mechanistic considerations for the relevance of animal data on thyroid neoplasia to human risk assessment," Mutation Res. 333:131-142, Elsevier Science Ltd. (1995).
Mertins, K., et al., "Transition-Metal-Catalyzed Benzylation of Arenes and Heteroarenes," Angew. Chem. Int. Ed. 44:238-242, Wiley-VCR Verlag GmbH & Co. (Dec. 2004).
Middleton, W.J., "New Fluorinating Reagents. Dialkylaminosulfur Fluorides," J. Org. Chem. 40:574-578, American Chemical Society (1975).
Miyahara, E.H., et al., "Thyroid hormone receptor-P-selective agonist GC-24 spares skeletal muscle type I to II fiber shift," Cell Tissue Res. 321:233-241, Springer-Verlag (Aug. 2005).
Mocchegiani, E., et al., "Neuroendocrine-thymus interactions. I. In vitro modulation of thymic factor secretion by thyroid hormones," J. Endocrinol. Invest. 13:139-147, Italian Society of Endocrinology (1990).
Moreno, M., et al., "How the thyroid controls metabolism in the rat: different roles for triiodothyronine and diiodothyronines," J. Physiol. 505:529-538, Cambridge Univ. Press (1997).
Morkin, E., et al., "Pilot Studies on the Use of 3, 5-Diiodothyropropionic Acid, a Thyroid Hormone Analog, in the Treatment of Congestive Heart Failure," Cardiology 97:218-225, S. Karger AG, Basel (Jul. 2002).
Moscioni, AD. and Gartner, L.M., "Thyroid Hormone and Hepatic UDP-Glucuronosyl Transferase Activity: Contrary Effects in Rat and Mouse," Res. Commun. Chem. Pathol. Pharmacol. 39:445-462, Pjd Publications Ltd (1983).
Murphy-Jolly, M.B., et al., "The synthesis of tris(perfluoroalkyl)phosphines," Chem. Commun. 4479-4480, Royal Society of Chemistry (Aug. 2005).
Nabeshima, T., et al., "Rate-accelerating Metal Ion Effects on Decarboxylation of a-Keto Acids by a Thiazolium lon bearing a Metal Binding Site," J. Chem. Soc. Chem. Commun. 373-374, Royal Society of Chemistry (1991).
Ness, G.C., et al., "Effects of L-Triiodothyronine and the Thyromimetic L-94901 on Serum Lipoprotein Levels and Hepatic Low-Density Lipoprotein Receptor, 3-Hydroxy-3-methylglutaryl Coenzyme A Reductase, and Apo A-I Gene Expression," Biochem. Pharmacol. 56:121-129, Elsevier Science Ltd (1998).
Nguyen, N.-H., et al., "Hammett Analysis of Selective Thyroid Hormone Receptor Modulators Reveals Structural and Electronic Requirements for Homone Antagonists," J. Am. Chem. Soc. 127:4599-4608, American Chemical Society (Mar. 2005).
Nishinaga, et al., "Model Reactions for the Biosynthesis of Thyroxine. XII. The Nature of a Thyroxine Precursor Formed in the Synthesis of Thyroxine from Diiodotyrosine and Its Keto Acid Analog," Biochemistry 7:388-397, American Chemical Society (1968).
Nurtdinov, S.Kh., et al., "Reactions of Alkylphosphonous Dichlorides with Carboxylic Acid Chlorides," Zhurnal Obshchei Khimii 41:2486-2490, Rossiiskaya Akademiya Nauk (1971).
Ocasio, Cory A, and Scanlan, T.S., "Clinical prospects for new thyroid hormone analogues" Curr. Opin. Endocrinol. Diabetes 12:363-370, Lippincott Williams & Wilkins (Oct. 2005).
Ocasio, Cory A, and Scanlan, T.S., "Design and characterization of a thyroid hermone receptor a (TRa)-Specific Agonist," ACS Chem. Biol. 1:585-593, American Chemical Society (Oct. 2006).
O'Reilly, Ian, and Murphy, M.P., "Studies on the rapid stimulation of mitochondrial respiration by thyroid hormones." Acta Endocrinol. 127:542-546, Romanian Society for Endocrinology (1992).
O'Reilly, Ian, and Murphy, M.P., "Treatment of hypothyroid rats with T2 (3,5-di-iodo-L-thyronine) rapidly stimulates respiration in subsequently isolated mitochondria," Biochem. Soc. Trans. 20:59S, Portland Press (1991).
Osuka, A, et al., "Synthesis of Arenephosphonates by Copper(!) Iodide-Promoted Arylation of Phosphite Anions," Synthesis 69-71, George Thieme Verlag-Stuttart (1983).
Pan, S.-Y., et al., "Bifendate treatment attenuates hepatic steatosis in cholesterol/bile salt- and high-fat diet-induced hypercholesterolemia in mice," Eur. J. Pharmacol. 552:170-175 Elsevier Science Ltd (Dec. 2006).
Panne, P., et al., "Cyanide initiated perfluoroorganylations with perfluoroorgano silicon comoounds" J. Fluorine Chem. 112:283-286 Elsevier Science Ltd (2001).
Petervari, E., et al., "Hyperphagia of hyperthyroidism: Is neuropeptide Y involved?" Regulatory Peptides 131:103-110, Elsevier Science Ltd (Nov. 2005).
Prashad, M., "Phosphonate vs. Phosphinate Elimination during Olefination of Aldehydes," Tetrahedron Lett. 34:1585-1588, Elsevier Science Ltd (1993).
Psarra, A.-M.G., et al., "The mitochondrion as a primary site of action of steroid and thyroid hormones: Presence and action of

(56) References Cited

OTHER PUBLICATIONS steroid and thyroid hormone receptors in mitochondria of animal cells." Mo!. Cell. Endocrinol. 246:21-33, Elsevier Science Ltd (Feb. 2006).
PubChem CID 15942005, National Center for Biotechnology Information, PubChem Compound Summary for CID 15942005, Unii3Z11398fnq, https://pubchem.ncbi.nlm.nih.gov/compound/15942005, accessed Aug. 18, 2022, create date Feb. 21, 2007.
Pue, M.A., et al., "The disposition of SK&F L-94901, a selective thyromimetic in rat, dog and cynomolgus monkey," Eur. J. Drug Metab. Pharmacokinetics 14:209-219, Edition Medecine Et Hygiene (1989).
Radominska-Pandya, A., et al., "A Historical Overview of the Heterologous Expression of Mammalian UDP-Glucuronosyltransferase Isoforms Over the Past Twenty Years," Curr. Drug Metab. 6:141-160, Bentham Science Publishers Ltd. (Apr. 2005).
Rai, R., and Katzenellenbogen, J.A., "Effect of Conformational Mobility and Hydrogen-Bonding Interactions on the Selectivity of Some Guanidinoaryl-Substituted Mechanism-Based Inhibitors of Trypsin-like Serine Proteases," J. Med. Chem. 35:4297-4305, American Chemical Society (1992).
Raparti et al., "Selective thyroid hormone receptor modulators," Indian J. Endocrinol. Metab. Mar.-Apr. 2013; 17(2): 211-218.
Rashid, S., et al., "Effect of Atorvastatin on High-Density Lipoprotein Apolipoprotein A-I Production and Clearance in the New Zealand White Rabbit," Circulation 106:2955-2960, Lippincott Williams & Wilkins (Dec. 2002).
Razumov, A.I. and Gazizov, M.B., "Reactivity of Organophosphorus Carbonyl-Containing Compounds IV. Synthesis, Properties, and Structure of Acylphosphinic Esters," Zhurnal Obshchei Khimii 37:2738-2742, Rossiiskaya Akademiya Nauk (1967).
Reiter et al. {Phosphinic acid-based MMP-13 inhibitors that spare MMP-1 and MMP-3, Bioorganic & Medicinal Chemistry Letters (2003), 13(14), 2331-2336.
Ren, S.G., et al., "Dose-Response Relationship Between Thyroid Hormone and Growth Velocity in Cynomolgus Monkeys," J. Clin. Endocrinol. Metab. 66:1010-1013, The Endocrine Society (1988).
Reuters Market News, "BRIEF—Viking Therapeutics says statistically significant reductions in fibrosis, liver collage, after 8 weeks of VK2809 treatment," [retrieved from Internet on Jul. 28, 2018] <URL: https://www.reuters.com/article/brief-viking-therapeutics-says-statistic/brief-viking-therapeutics-says-statistically-significant-reductions-in-fibrosis-liver-collagen-after-8-weeks-of-vk2809-treatment-idUSFWN1J308Y> Published online Jun. 6, 2017.
Ribeiro, R.C.J., et al., "X-ray Crystallographic and Functional Studies of Thyroid Hormone Receptor," J. Steroid Biochem. Molec. Biol. 65:133-141, Pergamon Press (1998).
Rooda, S.J.E., et al., "Metabolism of Triiodothyronine in Rat Hepatocytes," Endocrinology 125:2187-2197, The Endocrine Society (1989).
Ross, J. and Xiao, J., "Friedel-Crafts acylation reactions using metal triflates in ionic liquid," Green Chem. 4:129-133, Royal Society of Chemistry (Feb. 2002).
Ruhlandt-Senge, K. and Englich, U., "Synthesis and characterization of the first discrete potassium thiolates displaying three different coordination spheres at potassium in one molecule," Chem. Commun. 147-148, Royal Society of Chemistry (1996).
Ryono et al. CAS: 141:395288.
Ryono et al., 2004, CAS: 927006.
Saitoh, H. and Aungst, B.J., "Improvement of the Intestinal Absorption of a Peptidomimetic, Boronic Acid Thrombin Inhibitor Possibly Utilizing the Oligopeptide Transporter," Pharm. Res. 16:1786-1789, Plenum Publishing Corporation (1999).
Sakamoto, T., et al., "Cross-Coupling of N-Heteroaryl Halides with Active Methylene Compounds in the Presence of Tetrakis(triphenylphosphine)palladium," Chem. Pharm. Bull. 36:1664-1668, Pharmaceutical Society of Japan (1988).
Sakamoto, T., et al., "Palladium-Catalyzed Condensation of Aryl Halides with Phenylsulfonylacetonitrile and Diethyl Cyanomethylphosphonate," Chem. Pharm. Bull. 38:1513-1517, Pharmaceutical Society of Japan (1990).
Samuels, H.H., et al., "Depletion ofL-3,5,3'-Triiodothyronine and L-Thyroxine in Euthyroid Calf Serum for Use in Cell Culture Studies of the Action of Thyroid Hormone," Endocrinolof!V 105:80-85, The Endocrine Society (1979).
Sano, M. and Yamatera, H., "Potential Energy Surface of [Cu(H20)6]2+ and [Zn(H20)6] 2+ Derived From Ab Initio MO Calculations," Chem. Lett. 1495-1496, The Chemical Society of Japan (1980).
Sass, D.A., et al., "Nonalcoholic Fatty Liver Disease: A Clinical Review," Dig. Dis. Sci. 50:171-180, Springer Science Business Media, Inc. (Jan. 2005).
Saulnier, M.G., et al., "Microwave-assisted synthesis of primary amine HX salts from halides and 7M ammonia in methanol," Tetrahedron Lett. 45:397-399, Elsevier Science Ltd. (Jan. 2004).
Schlosser, M. and Geneste, H., "The Organometallic Route to Benzylamine Type Monoamine Oxidase Inhibitors," Tetrahedron 54:10119-10124, Pergamon Press (1998).
Schmitt, L., et al., "Synthesis of Arylalkylmonofluorophosphonates as Myo-Inositol monophosphatase Ligands," Tetrahedron Lett. 39:4009-4012, Elsevier Science Ltd. (1998).
Schroder-van der Elst, J.P., et al., "Effects of 5,5'-diphenylhydantoin on the thyroid status in rats," Eur. J. Endocrinol. 134:221-224, BioScientifica Ltd (1996).
Selenkow, H.A. and Asper, Jr., S.P., "Biological Activity of Compounds Structurally Related to Thyroxine," Physiol. Rev. 35:426-474, American Physiological Society (1955).
Shi, Y., et al., "Mutant-Selective Thyromimetics for the Chemical Rescue of Thyroid Hormone Receptor Mutants Associated with Resistance to Thyroid Hormone," Biochemistry 44:4612-4626, American Chemical Society (Mar. 2005).
Smith, C.L. and O'Malley, B.W., "Coregulator Function: A Key to Understanding Tissue Specificity of Selective Receptor Modulators," Endocrine Rev. 25:45-71, The Endocrine Society (Feb. 2004).
Soldin, SJ., et al., "The measurement of free thyroxine by isotope dilution tandem mass spectrometry," Clinica Chimica Acta 358:113-118, Elsevier Science Ltd (Aug. 2005).
Song, K., et al., "Induction of angiotensin converting enzyme and angiotensin II receptors in the atherosclerotic aorta of high-cholesterol fed Cynomolgus monkeys," Atherosclerosis 138:171-182, Elsevier Science Ltd (1998).
Stanton, J.L., et al., "Synthesis and Biological Activity of Phenoxyphenyl Oxamic Acid Derivatives Related to L-Thyronine," Bioorg. Med. Chem. Lett. 10:1661-1663, Elsevier Science Ltd (2000).
Sterling, K. and Brenner, M.A., "Thyroid Hormone Action: Effect of Triiodothyronine on Mitochondrial Adenine Nucleotide Translocase In Vivo and In Vitro," Metabolism 44:193-199, W.B. Saunders (1995).
Tacke, et al., "An update on the recent advances in antifibrotic therapy," Expert Review of Gastroenterology & Hepatology (2018) vol. 12(11), pp. 1143-1152. Epub Oct. 3, 2018.
Tai, S.S.-C., et al., "Candidate Reference Method for Total Thyroxine in Human Serum: Use of Isotope-Dilution Liquid Chromatography-Mass Spectrometry with Electrospray lonizaton," Clin. Chem. 48:637-642, American Association For Clinical Chemistry (Jan. 2002).
Takayama, S., et al., "Antithyroid Effects of Propylthiouracil and Sulfamonomethoxine in Rats and Monkeys," Toxicol. Applied Pharmacol. 82:191-199, Academic Press (1986).
Tal, D.M. and Karlish, S.J.D., "Synthesis of a Novel Series of Arylmethylisothiouronium Derivatives," Tetrahedron 51:3823-3830, Pergamon Press (1995).
Taylor, A.H., et al., "Beneficial Effects of a Novel Thyromimetic on Lipoprotein Metabolism," Mo!. Pharmacol. 52:542-547, American Society for Pharmacology and Experimental Therapeutics (1997).
Taylor, S.D., et al., "Synthesis of Aryl(DifluoromethylenePhosphonates) via Electrophilic Fluorination of a-Carbanions ofBenzylic Phosphonates with N-Fluorobenzenesulfonimide," Tetrahedron 54:1691-1714, Pergamon Press (1998).
Thienpont, L.M., et al., "Isotope Dilution-Gas Chromatography/Mass Spectrometry and Liquid Chromatography/Electrospray Ionization-Tandem Mass Spectrometry for the Determination of Triiodo-

(56) References Cited

OTHER PUBLICATIONS

L-Thyronine in Serum," Rapid Commun. Mass Spectrometry 13:1924-1931, John Wiley & Sons, Ltd (1999).
Thornber, C.W., "Isosterismand Molecular Modification in Drug Design," Chem. Soc. Rev. 8:563-580, Chemical Society (1979).
Togashi, M., et al., "Conformational adaptation of nuclear receptor ligand binding domains to agonists: Potential for novel approaches to ligand design," J. Steroid Biochem. Mo!. Biol. 93:127-137, Elsevier Science Ltd (Feb. 2005).
Tomilov, AP., et al., "Electrochemical synthesis of diethyl fluoromethanephosphonate," J. Fluorine Chem. 82:39-41, Elsevier Science Ltd. (1997).
Toussaint, 0., et al., "The Copper(I)-Catalyzed Decarboxylation of Malonic Acids: AN ew Mild and Quantitative Method," Synthesis 1029-1031, Georg Thieme Verlag (1986).
Trost, S.U., et al., "The Thyroid Hormone Receptor-13-Selective Agonist GC-1 Differentially Afftects Plasma Lipids and Cardiac Activity," Endocrinology 141:3057-3064, The Endocrine Society (2000).
Tsuchimoto, T., et al., "Scandium(III) Triflate Catalyzed Friedel-Crafts Alkylation Reactions," J. Org. Chem. 62:6997-7005, American Chemical Society (1997).
Tully et al., "Discovery of Tropifexor (LJN452), a highly potent non-bile acid FXR agonist for the treatment of cholestatic liver deseases and nonalcoholic steatohepatitis (NASH)", J. Med. Chem. vol. 60:9960-9973 (2017).
Tyree, E.B., et al., "Effect of L-Triiodothyronine on Radiation-Induced Pulmonary Fibrosis in Dogs", Radiation Research (1966) vol. 28, pp. 30-36.
Underwood, A.H., et al., "A thyromimetic that decreases plasma cholesterol levels without increasing cardiac activity," Nature 324:425-429, Nature Publishing Group (1986).
Van Rompaey, K., et al., "A versatile synthesis of 2-substituted 4-amino-1,2,4,5-tetrahydro-2-benzazepine-3-ones," Tetrahedron 59:4421-4432, Pergamon Press (Apr. 2003).
Vaughan, M.K., et al., "Chronic Exposure to Short Photoperiod Inhibits Free Thyroxine Index and Plasma Levels of TSH, T4, Triiodothyronine (T3) and Cholesterol in Female Syrian Hamsters," Comp. Biochem. Physiol. 7JA:615-618, Pergamon Press Ltd (1982).
Veer, G.V.D.S., et al., "Temperature Effects on Free-Thyroxine Measurements: Analytical and Clinical Consequences," Clin. Chem. 38:1327-1331, American Association For Clinical Chemistry (1992).
Verd, J.C., et al., "Different effect of simvastatin and atorvastatin on key enzymes :involved in VLDL synthesis and catabolismin high fat/cholestrol fed rabbits," Br. J. Pharmacol. 127:1479-1485, Nature Publishing Group (1999).
Villicev, C.M., et al., "Thyroid hormone receptor-specific agonist GC-1 increases energy expenditure and prevents fat-mass accumulation in rats," J. Endocrinol. 193:21-29, Society for Endocrinology (Jan. 2007).
Visser, T.J., et al., "Deiodination of Thyroid Hormone by Human Liver," J. Clin. Endocrinol. Metab. 67:17-24, The Endocrine Society (1988).
Walker, D.M., et al., "Design and Synthesis of y-Oxygenated Phosphinothricins as Inhibitors of Gluamine Synthetase," J. Chem. Soc. Perkin Trans. 1 659-666, Royal Society of Chemistry (1990).
Wang, B., et al., "Effects of triiodo-thyronine on angiotensin-induced cardiomyocyte hypertrophy: reversal of increased -myosin heavy chain gene expression," Can. J. Physiol. Pharmacol. 84:935-941, NRC Research Press (Aug. 2006).
Wang, R., et al., "Salsalate Administration—A Potential Pharmacological Model of the Sick Euthyroid Syndrome," J. Clin. Endocrinol. Metab. 83:3095-3099, Endocrine Society (1998).
Waschbusch, R., et al., "A high yield:ing synthesis of diethyl-l-fluoromethylphosphonate in pure form," C. R Acad. Sci. Paris, t. I, Serie II c 1:49-52, Elsevier Science Ltd (1998).
Wasserscheid, P. and Keim, W., "Ionic Liquids—New "Solutions" for Transition Metal Catalysis," Angew Chem. Int. Ed. 39:3772-3789, Wiley-VCR Verlag GmbH (2000).
Webb, P., et al., "Design of thyroid hormone receptor antagonists from first principles," J. Steroid Biochem. Mo!. Biol. 83:59-73, Elsevier Science Ltd (Dec. 2002).
Wechter, W.J., et al., "Hypocholesterolemic Agents. Thyroalkanols," J. Med. Chem. 8:474-478, American Chemical Society (1965).
Weiskirchen, "Hepatoprotective and anti-fibrotic agents: It's time to take the next step", Frountiers in Pharmacology, vol. 6(7):1-40 (2016).
Wells, P.G., et al., "Effect ofthyrotoxicosis on liver blood flow andpropranolol disposition after long-term dosing," Clin. Pharmacol. Ther. 33:603-608, Nature Publishing Group (1983).
Welton, T., "Room-Temperature Ionic Liquids. Solvents for Synthesis and Catalysis," Chem. Rev. 99:2071-2083, American Chemical Society (1999).
Wibom, R., et al., "A sensitive method for measuring ATP-formation in rat muscle mitochondria," Scand. J Clin. Lab. Invest. 50:143-152, Taylor & Francis Health Sciences (1990).
Wienand, A, et al., "Design, Synthesis and Biological Evaluation of Selective Boron-containing Thrombin Inhibitors," Bioorg. Med. Chem. 7:1295-1307, Elsevier Science Ltd. (1999).
Willnow, T.E. and Herz, J., "Animal models for disorders of hepatic lipoprotein metabolism," J Mal. Med. 73:213-220, Springer-Verlag (1995).
Winder, W.W., et al., "Effects of thyroid hormone administration on skeletal muscle mitochondria," Am. J Physiol. 228:1341-1345, American Physiological Society (1975).
Wondisford, F.E., "Unlikely partners in weight loss?," Cell Metab. 3:81-82, Cell Press (Feb. 2006).
Wu, K.-M. and Farrelly, J.G., "Preclinical Development of New Drugs that Enhance Thyroid Hormone Metabolism and Clearance: Inadequacy of Using Rats as an Animal Model for Predicting Human Risks in an IND and NDA," Am. J Therap. 13:141-144, Lippincott Williams & Wilkins (Mar./Apr. 2006).
Wu, Y., et al., "Removal of Thiazolidinethione Auxiliaries with Benzyl Alcohol Mediated by DMAP," J Org. Chem. 69:6141-6144, American Chemical Society (May 2004).
Xu, L., et al., "Heck Reaction in lonic Liquids and the in Situ Identification of N-Heterocyclic Carbene Complexes of Palladium," Organometallics 19:1123-1127, American Chemical Society (2000).
Yang, W., et al., "Boronic Acid Compounds as Potential Pharmaceutical Agents," Med. Res. Rev. 23:346-368, Wiley Periodicals, Inc. (May 2003).
Yang, C. and Pittman, Jr., C.U., "Reductions of Organic Functional Groups Using NaBHi or NaBH, JLiCl in Diglyme at 125 to 162° C.," Synth. Commun. 28:2027-2041, Georg Thieme Verlag (1998).
Yao, et al., "Regulation of fatty acid composition and lipid storage by thyroid hormone in mouse liver," Cell & Bioscience, Biomed Central Ltd. Vo. 4, No. 1 Jul. 30, 2014.
Ye, L., et al., "Thyroid Receptor Ligands. I. Agonist Ligands Selective for the Thyroid Receptor pl," J Med. Chem. 46:1580-1588, American Chemical Society (Mar. 2003).
Yen, P.M., "Physiological and Molecular Basis of Thyroid Hormone Action," Physiol. Rev. 81:1097-1142, American Physiological Society (2001).
Yoshihara, H.A.1., et al., "Structural Determinants of Selective Thyromimetics" J. Med. Chem. 46:3152-3161, American Chemical Society (Jul. 2003).
Yoshioka, R., et al., "The Optical Resolution and Asymmetric Transformation of DL-p-Hydroxypheny!glycine with (+)-1-Phenylethanesulfonic Acid," Bull. Chem. Soc. Jpn. 60:649-652, The Chemical Society of Japan (1987).
Yu, K.-L., et al., "Concerning the Phosphorylation of Vicinal Dials," Synth. Commun. 18:465-468, Taylor & Francis, Inc. (1988).
Yu et al., "Thyroid hormone inhibits lung fibrosis in mice by improving epithelial mitochondrial function", Nature Medicine (2018) vol. 24(1), pp. 39-49. Epub Dec. 4, 2017.
Viking Therapeutics, Press releases, "Viking Therapeutics Announces Presentation of Data from In Vivo Proof-of-Concept Study of VK2809 in Glycogen Storage Disease la (GSD la) at the 13th International Congress of Inborn Errors of Metabolism (ICIEM)", [retrieved from internet on Jun. 8, 2018] <URL: http://ir.vikingtherapeutics.com/2017-09-07-Viking-Therapeutics-Announces-Presentation-of-Data-from-In-Vivo-Proof-of-Concept-Study-of-

(56) References Cited

OTHER PUBLICATIONS

VK2809-in-Glycogen-Storage-Disease-la-GSD-la-at-the-13th-International-Congress-of-Inborn-Errors-of-Metabolism-ICIEM> published on Sep. 7, 2017.
Viking Therapeutics—News & Events, "Viking Therapeutics Presents Results from In Vivo Study of VK2809 in Biopsy—Confirmed Non-Alcoholic Steatohepatitis (NASH) at the Annual Meeting of the American Association for the Study of Liver Diseases (AASLD)", Oct. 24, 2017, San Diego <URL: http://ir.vikingtherapeutics.com/2017-10-24-Viking-Therapeutics-Presents-Results-from-In-Vivo-Study-of-VK2809-in-Biopsy-Confirmed-Non-Alcoholic-Steatohepatitis-NASH-at-the-Annual-Meeting-of-the-American-Association-for-the-Study-of-Liver-Diseases-AASLD> [retrieved from Internet on Feb. 9, 2020].
Viking Therapeutics—News & Events, "Viking Therapeutics Announces Results of Gene Expression Analysis from In Vivo Study of VK2809 in Non-Alcoholic Steatohepatitis (NASH)", Sep. 11, 2017, San Diego <URL: http://ir.vikingtherapeutics.com/2017-09-11-Viking-Therapeutics-Announces-Results-of-Gene-Expression-Analysis-from-In-Vivo-Study-of-VK2809-in-Non-Alcoholic-Steatohepatitis-NASH> [retrieved from Internet on Feb. 9, 2020].
Zalkow, L.H., et al., "Studies in the Synthesis of Camptothecin. An Efficient Synthesis of2,3-Dihydro-1H-pyrrolo[3,4-b]quinoline," J. Chem. Soc. 3551-3554, Royal Society of Chemistry (1971).
Zenker, N. and Jorgensen, E.C., "Thyroxine Analogs. I. Synthesis of 3,5-Diiodo-4-(2'-alkylphenoxy)-DL-phenylalanines," J. Am. Chem. Soc. 81:4643-4647, American Chemical Society (1959).
Zhang, N. and Casida, J.E., "Novel Irreversible Butyrylcholinesterase Inhibitors: 2-Chloro-1-(substituted-phenyl)ethylphosphonic Acids," Bioorg. Med. Chem. 10:1281-1290, Elsevier Science Ltd (Nov. 2002).
Zhang, J. and Lazar, M.A., "The Mechanism of Action of Thyroid Hormones," Annu. Rev. Physiol. 62:439-466, Annual Reviews (2000).
Zhou et al., "A liver-specific thyromimetic, VK2809, Decreases Hepatosteatosis in Glycogen Storage Disease Type 1a", Thyroid, vol. 29(8):1158-1167 (2019).
Newsome et al., "The effect of semaglutide on liver enzymes in subjects with obesity and elevated alanine aminotransferase: data from a randomized phase 2 trial", Conference Reports for NATAP, The Liver Meeting, San Francisco, Nov. 2018, in 10 pages (2018).
Ofosu et al., "Non-alcoholic fatty liver disease: controlling an emerging epidemic, challenges, and future directions", Annals of Gastroenterology, vol. 31:288-295 (2018).
Rojkind et al., "Collagen types in normal and cirrhotic liver", vol. 76(4):710-719 (1979).

* cited by examiner

Vehicle

Compound 2 (low)

Compound 2 (high)

Compound 1

Elafibranor

Vehicle

Compound 2 (low)

Compound 2 (high)

Compound 1

Elafibranor

COMPOSITIONS FOR THE TREATMENT OF FIBROSIS

FIELD

The compositions and methods of the present disclosure relate generally to the field of treatments for fibrotic disease.

BACKGROUND

Fibrosis is a pathogenic hallmark of a vast number of conditions, implicating a wide variety of tissues, among them the liver (e.g., non-alcoholic steatohepatitis, glycogen storage disease type IX, cirrhosis), the lung (e.g., chronic interstitial lung disease, pneumoconiosis, silicosis, emphysema, fibrosing lung diseases, idiopathic pulmonary fibrosis, nonspecific interstitial pneumonia, cryptogenic organizing pneumonia), the vasculature (e.g., diffuse interstitial fibrosis; atherosclerosis), the heart (e.g., cardiac fibrosis; atrial fibrosis; endomyocardial fibrosis), the skin (e.g., keloid lesions, nephrogenic systemic fibrosis, scleroderma), joints and interstitial tissues (e.g., arthrofibrosis, Dupuytren's disease), the pancreas (e.g., pancreatitis), the mouth (e.g., fibrous proliferative lesions of the oral cavity), the gut (e.g., fibrosing strictures, for example, related to Crohn's disease), the brain (glial scarring, leptomeningeal fibrosis associated with bacterial meningitis). Fibrosis may also result from environmental insults or a variety of injuries, such as, for example, exposure to ionizing radiation (such as during cancer treatments), as a result of cystic rupture in the breast, (causing palpable lesions in mammary tissue), and generally as a result of overdeposition of collagen following a wound or tissue insult, such as after injury or surgery.

While some types of fibrosis involve underlying genetic predispositions (e.g., Dupuytren's disease), most types involve prolonged inflammation of the affected tissue (e.g., hepatic fibroses and pneumoconial fibroses). Symptoms may be as minor as pruritis and aesthetic concerns (e.g., in the case of keloid lesions of the skin) or as significant as pulmonary failure and death (e.g., as terminal symptoms of pulmonary fibroses and cardiac fibroses). While fibrosis is essentially irreversible once established, treatments exist to slow the progression of various fibrotic conditions, or to ameliorate fibrosis or fibrotic conditions. Current antifibrotic treatments include anti-inflammatory compounds such as pirfenidone and fibroblast growth factor receptor antagonist nintedanib. For dermal and subdermal fibroses, examples of current therapies include surgery, phototherapy and injections of *Clostridium histolyticum* collagenase. However, due to the irreversible nature of the various fibroses, as well as the limited efficacy of current therapies, there remains a need for additional therapeutic approaches to this class of conditions.

SUMMARY

Disclosed herein are methods of treating fibroses, fibrotic conditions or fibrotic symptoms in a subject in need thereof comprising administering to said subject at least one compound of Formula I:

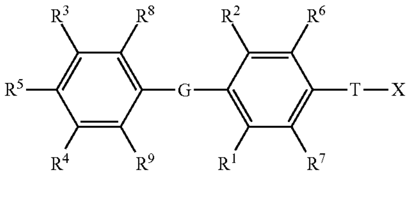

or a pharmaceutically acceptable salt thereof, wherein:

G is selected from the group consisting of —O—, —S—, —S(=O)—, —S(=O)$_2$—, —Se—, —CH$_2$—, —CF$_2$—, —CHF—, —C(O)—, —CH(OH)—, —CH(C$_1$-C$_4$ alkyl)-, —CH(C$_1$- C$_4$ alkoxy)-, —C(=CH$_2$)—, —NH—, and —N(C$_1$-C$_4$ alkyl)-;

T is selected from the group consisting of —(CR$^a_2$)$_k$—, —CR$^b$=CR$^b$—(CR$^a_2$)$_n$—, —(CR$^a_2$)$_n$—CR$^b$=CR$^b$—, —(CR$^a_2$)—CR$^b$=CR$^b$—(CR$^a_2$)—, —O(CR$^b_2$)(CR$^a_2$)$_n$—, —S(CR$^b_2$)(CR$^a_2$)n-, N(R$^c$)(CR$^b_2$)(CR$^a_2$)$_n$—, N(R$^b$)C(O)(CR$^a_2$)$_n$, —C(O)(CR$^a_2$)$_m$—, —(CR$^a_2$)$_m$C(O)—, —(CR$^a_2$)C(O)(CR$^a_2$)$_n$, —(CR$^a_2$)$_n$C(O)(CR$^a_2$)—, and —C(O)NH(CR$^b_2$)(CR$^a_2$)$_p$—;

k is an integer from 1-4;

m is an integer from 0-3;

n is an integer from 0-2;

p is an integer from 0-1;

each R$^a$ is independently selected from the group consisting of hydrogen, optionally substituted —C$_1$-C$_4$ alkyl, halogen, —OH, optionally substituted —O—C$_1$-C$_4$ alkyl, —OCF$_3$, optionally substituted —S—C$_1$-C$_4$ alkyl, —NR$^b$R$^c$, optionally substituted —C$_2$- C$_4$ alkenyl, and optionally substituted —C$_2$-C$_4$ alkynyl; with the proviso that when one R$^a$ is attached to C through an O, S, or N atom, then the other R$^a$ attached to the same C is a hydrogen, or attached via a carbon atom;

each R$^b$ is independently selected from the group consisting of hydrogen and optionally substituted —C$_1$-C$_4$ alkyl;

each R$^c$ is independently selected from the group consisting of hydrogen and optionally substituted —C$_1$-C$_4$ alkyl, optionally substituted —C(O)—C$_1$-C$_4$ alkyl, and —C(O)H;

R$^1$, and R$^2$ are each independently selected from the group consisting of halogen, optionally substituted —C$_1$-C$_4$ alkyl, optionally substituted —S—C$_1$-C$_3$ alkyl, optionally substituted —C$_2$-C$_4$ alkenyl, optionally substituted —C$_2$-C$_4$ alkynyl, —CF$_3$, —OCF$_3$, optionally substituted-O—C$_1$-C$_3$ alkyl, and cyano;

R$^6$, R$^7$, R$^8$, and R$^9$ are each independently selected from the group consisting of are each independently selected from the group consisting of hydrogen, halogen, optionally substituted —C C$_1$-C$_4$ alkyl, optionally substituted —S—C$_1$-C$_3$ alkyl, optionally substituted —C$_2$-C$_4$ alkenyl, optionally substituted —C$_2$-C$_4$ alkynyl, —CF$_3$, —OCF$_3$, optionally substituted-O—C$_1$-C$_3$ alkyl, and cyano; or R$^6$ and T are taken together along with the carbons they are attached to form a ring of 5 to 6 atoms including 0 to 2 heteroatoms independently selected from —NR$^i$—, —O—, and —S—, with the proviso that when there are 2 heteroatoms in the ring and both heteroatoms are different than nitrogen then both heteroatoms have to be separated by at least one carbon atom; and X is attached to this ring by a direct bond to a ring carbon, or by —(CR$^a_2$)— or —C(O)— bonded to a ring carbon or a ring nitrogen;

R$^i$ is selected from the group consisting of hydrogen, —C(O)C$_1$-C$_4$ alkyl, —C$_1$-C$_4$ alkyl, and —C$_1$-C$_4$-aryl;

R$^3$ and R$^4$ are independently selected from the group consisting of hydrogen, halogen, —CF$_3$, —OCF$_3$, cyano, optionally substituted —C$_1$-C$_{12}$ alkyl, optionally substituted —C$_2$-C$_{12}$ alkenyl, optionally substituted —C$_2$-C$_{12}$ alkynyl, —SR$^d$, —S(=O)R$^e$, —S(=O)$_2$R$^e$, —S(=O)$_2$NR$^f$R$^g$, —C(O)OR$^h$, —C(O)R$^e$, —N(R$^b$)C(O)NR$^f$R$^g$, —N(R$^b$)S(=O)$_2$R$^e$, —N(R$^b$)S(=O)$_2$NR$^f$R$^g$, and —NR$^f$R$^g$;

each $R^d$ is selected from the group consisting of optionally substituted —$C_1$-$C_{12}$ alkyl, optionally substituted —$C_2$-$C_{12}$ alkenyl, optionally substituted —$C_2$-$C_{12}$ alkynyl, optionally substituted —$(CR^b{}_2)_n$ aryl, optionally substituted —$(CR^b{}_2)_n$ cycloalkyl, optionally substituted —$(CR^b{}_2)_n$ heterocycloalkyl, and —C(O)$NR^f R^g$;

each $R^e$ is selected from the group consisting of optionally substituted —$C_1$-$C_{12}$ alkyl, optionally substituted —$C_2$-$C_{12}$ alkenyl, optionally substituted —$C_2$-$C_{12}$ alkynyl, optionally substituted —$(CR^a{}_2)_n$ aryl, optionally substituted —$(CR^a{}_2)_n$ cycloalkyl, and optionally substituted —$(CR^a{}_2)_n$ heterocycloalkyl;

$R^f$ and $R^g$ are each independently selected from the group consisting of hydrogen, optionally substituted —$C_1$-$C_{12}$ alkyl, optionally substituted —$C_2$-$C_{12}$ alkenyl, optionally substituted —$C_2$-$C_{12}$ alkynyl, optionally substituted —$(CR^b{}_2)_n$ aryl, optionally substituted —$(CR^b{}_2)$n cycloalkyl, and optionally substituted —$(CR^b{}_2)_n$ heterocycloalkyl, or $R^f$ and $R^g$ may together form an optionally substituted heterocyclic ring, which may contain a second heterogroup selected from the group consisting of O, $NR^C$, and S, wherein said optionally substituted heterocyclic ring may be substituted with 0-4 substituents selected from the group consisting of optionally substituted —$C_1$-$C_4$ alkyl, —$OR^b$, oxo, cyano, —$CF_3$, optionally substituted phenyl, and —C(O)$OR^h$;

each $R^h$ is selected from the group consisting of optionally substituted —$C_1$-$C_{12}$ alkyl, optionally substituted —$C_2$-$C_{12}$ alkenyl, optionally substituted —$C_2$-$C_{12}$ alkynyl, optionally substituted —$(CR^b{}_2)_n$ aryl, optionally substituted —$(CR^b{}_2)_n$ cycloalkyl, and optionally substituted —$(CR^b{}_2)_n$ heterocycloalkyl;

$R^5$ is selected from the group consisting of —OH, optionally substituted —$OC_1$-$C_6$ alkyl, OC(O)$R^e$, —OC(O)$OR^h$, —F, —NHC(O)$R^e$, —NHS(═O)$R^e$, —NHS(═O)$_2R^e$, —NHC(═S)NH($R^h$), and —NHC(O)NH($R^h$);

X is P(O)$YR^{11}Y'R^{11}$;

Y and Y' are each independently selected from the group consisting of —O—, and —$NR^v$—;

when Y and Y' are —O—, $R^{11}$ attached to —O— is independently selected from the group consisting of —H, alkyl, optionally substituted aryl, optionally substituted heterocycloalkyl, optionally substituted $CH_2$-heterocycloakyl wherein the cyclic moiety contains a carbonate or thiocarbonate, optionally substituted -alkylaryl, —$C(R^z)_2OC(O)NR^z{}_2$, —$NR^z$—C(O)—$R^y$, —$C(R^z)_2$—OC(O)$R^y$, —$C(R^z)_2$—O—C(O)$OR^y$, —$C(R^z)_2OC(O)SR^y$, - alkyl-S—C(O)$R^y$, -alkyl-S—S-alkylhydroxy, and -alkyl-S—S—S-alkylhydroxy;

when Y and Y' are —$NR^v$—, then $R^{11}$ attached to —$NR^v$— is independently selected from the group consisting of —H, —$[C(R^z)_2]_q$—$COOR^y$, —$C(R^x)_2$ $COOR^Y$, —$[C(R^z)_2]_q$—C(O)$SR^y$, and -cycloalkylene-$COOR^y$;

when Y is —O— and Y' is $NR^v$, then $R^{11}$ attached to —O— is independently selected from the group consisting of —H, alkyl, optionally substituted aryl, optionally substituted heterocycloalkyl, optionally substituted $CH_2$-heterocycloakyl wherein the cyclic moiety contains a carbonate or thiocarbonate, optionally substituted -alkylaryl, —$C(R^z)_2OC(O)NR^z{}_2$, —$NR^z$—C(O)—$R^y$, —$C(R^z)_2$—OC(O)$R^y$, —$C(R^z)_2$—O—C(O)$OR^y$, —$C(R^z)_2OC(O)SR^y$, -alkyl-S—C(O)$R^y$, -alkyl-S—S-alkylhydroxy, and -alkyl-S—S—S-alkylhydroxy; and $R^{11}$ attached to —$NR^v$— is independently selected from the group consisting of H, —$[C(R^z)_2]_q$—$COOR^y$, —$C(R^x)_2COOR^y$, —$[C(R^z)_2]_q$—C(O)$SR^y$, and -cycloalkylene-$COOR^y$;

or when Y and Y' are independently selected from —O— and $NR^v$, then together $R^{11}$ and $R^{11}$ are -alkyl-S—S-alkyl- to form a cyclic group, or together $R^{11}$ and $R^{11}$ are the group:

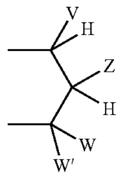

wherein:

V, W, and W' are independently selected from the group consisting of hydrogen, optionally substituted alkyl, optionally substituted aralkyl, heterocycloalkyl, aryl, substituted aryl, heteroaryl, substituted heteroaryl, optionally substituted 1-alkenyl, and optionally substituted 1-alkynyl;

or together V and Z are connected via an additional 3-5 atoms to form a cyclic group containing 5-7 atoms, wherein 0-1 atoms are heteroatoms and the remaining atoms are carbon, substituted with hydroxy, acyloxy, alkylthiocarbonyloxy, alkoxycarbonyloxy, or aryloxycarbonyloxy attached to a carbon atom that is three atoms from both Y groups attached to the phosphorus;

or together V and Z are connected via an additional 3-5 atoms to form a cyclic group, wherein 0-1 atoms are heteroatoms and the remaining atoms are carbon, that is fused to an aryl group at the beta and gamma position to the Y attached to the phosphorus;

or together V and W are connected via an additional 3 carbon atoms to form an optionally substituted cyclic group containing 6 carbon atoms and substituted with one substituent selected from the group consisting of hydroxy, acyloxy, alkoxycarbonyloxy, alkylthiocarbonyloxy, and aryloxycarbonyloxy, attached to one of said carbon atoms that is three atoms from a Y attached to the phosphorus;

or together Z and W are connected via an additional 3-5 atoms to form a cyclic group, wherein 0-1 atoms are heteroatoms and the remaining atoms are carbon, and V must be aryl, substituted aryl, heteroaryl, or substituted heteroaryl;

or together W and W' are connected via an additional 2-5 atoms to form a cyclic group, wherein 0-2 atoms are heteroatoms and the remaining atoms are carbon, and V must be aryl, substituted aryl, heteroaryl, or substituted heteroaryl;

Z is selected from the group consisting of —$CHR^zOH$, —$CHR^zOC(O)R^y$, —$CHR^zOC(S)R^y$, —$CHR^zOC(S)OR^y$, —$CHR^zOC(O)SR^y$, —$CHR^zOCO_2R^y$, —$OR^z$, —$SR^z$, —$CHR^zN_3$, —$CH_2$-aryl, —CH(aryl)OH, —CH(CH═$CR^z{}_2$)OH, —CH(C≡$CR^z$)OH, —$R^z$, —$NR^z{}_2$, —$OCOR^y$, —$OCO_2R^y$, —$SCOR^y$, —$SCO_2R^y$, —$NHCOR^z$, —$NHCO_2R^y$, —$CH_2$NH-aryl, —$(CH_2)$q-$OR^z$, and —$(CH_2)$q-$SR^z$;

q is an integer 2 or 3;

each $R^z$ is selected from the group consisting of $R^y$ and —H;

each $R^y$ is selected from the group consisting of alkyl, aryl, heterocycloalkyl, and aralkyl;

each $R_x$ is independently selected from the group consisting of —H, and alkyl, or together $R^x$ and $R^x$ form a cyclic alkyl group; and each $R^v$ is selected from the group consisting of —H, lower alkyl, acyloxyalkyl, alkoxycarbonyloxyalkyl, and lower acyl.

According to the methods and compositions described herein, the compound to be administered may comprise one or more of the compounds having a structure selected from the group consisting of:

(Compound 1)

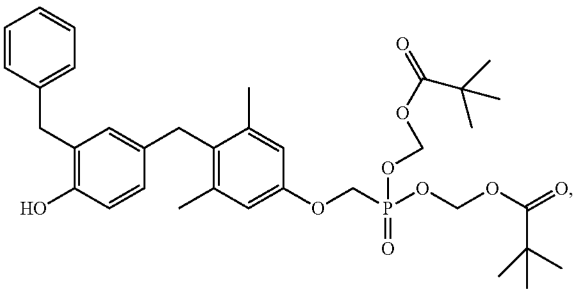

(Compound 2)

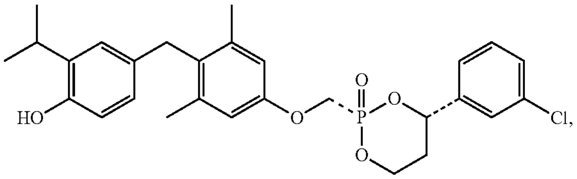

(Compound 3)

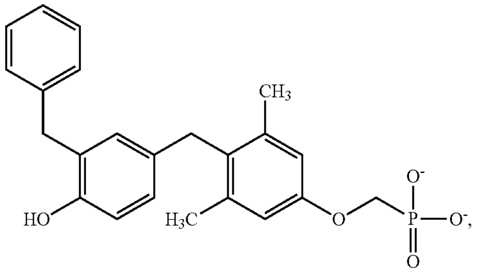

and (Compound 4)

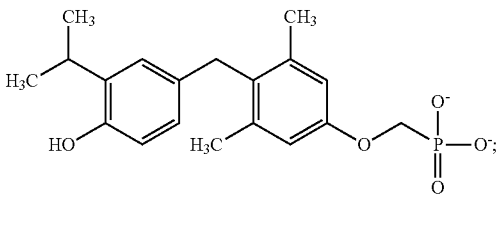

or pharmaceutically acceptable salts thereof.

According to the methods and compositions disclosed herein, the compounds described above may be administered to treat, ameliorate, prevent, or cure one or more fibrotic conditions selected from glycogen storage disease type III (GSD III), glycogen storage disease type VI (GSD VI), glycogen storage disease type IX (GSD IX), non-alcoholic steatohepatitis (NASH), cirrhosis, hepatitis, scleroderma, alcoholic fatty liver disease, atherosclerosis, asthma, cardiac fibrosis, organ transplant fibrosis, muscle fibrosis, pancreatic fibrosis, bone-marrow fibrosis, liver fibrosis, cirrhosis of liver and gallbladder, fibrosis of the spleen, pulmonary fibrosis, idiopathic pulmonary fibrosis, diffuse parenchymal lung disease, idiopathic interstitial fibrosis, diffuse interstitial fibrosis, interstitial pneumonitis, desquamative interstitial pneumonia, respiratory bronchiolitis, interstitial lung disease, chronic interstitial lung disease, acute interstitial pneumonitis, hypersensitivity pneumonitis, nonspecific interstitial pneumonia, cryptogenic organizing pneumonia, lymphocytic interstitial pneumonia, pneumoconiosis, silicosis, emphysema, interstitial fibrosis, sarcoidosis, mediastinal fibrosis, cardiac fibrosis, atrial fibrosis, endomyocardial fibrosis, renal fibrosis, chronic kidney disease, Type II diabetes, macular degeneration, keloid lesions, hypertrophic scar, nephrogenic systemic fibrosis, injection fibrosis, complications of surgery, fibrotic chronic allograft vasculopathy and/or chronic rejection in transplanted organs, fibrosis associated with ischemic reperfusion injury, post-vasectomy pain syndrome, fibrosis associated with rheumatoid arthritis, arthrofibrosis, Dupuytren's disease, dermatomyositis-polymyositis, mixed connective tissue disease, fibrous proliferative lesions of the oral cavity, fibrosing intestinal strictures, Crohn's disease, glial scarring, leptomeningeal fibrosis, meningitis, systemic lupus erythematosus, fibrosis due to radiation exposure, fibrosis due to mammary cystic rupture, myelofibrosis, retroperitoneal fibrosis, progressive massive fibrosis, psoriasis, or symptoms or sequelae thereof, or other diseases or conditions resulting in the excessive deposition of extracellular matrix components, such as collagen, which may be affected by interventions within the TRβ pathway, or any combination thereof. The methods and compositions according to the present disclosure may comprise a primary fibrosis, or a condition in which said fibrosis, fibrotic condition or fibrotic symptom is secondary to or symptomatic of another condition.

In some embodiments according to the methods and compositions as disclosed herein, said fibrosis, fibrotic condition or fibrotic symptom may comprise one or more of scleroderma, atherosclerosis, cardiac fibrosis, organ transplant fibrosis, muscle fibrosis, pancreatic fibrosis, bone-marrow fibrosis, liver fibrosis, fibrosis of the spleen, pulmonary fibrosis, idiopathic pulmonary fibrosis, idiopathic interstitial fibrosis, diffuse interstitial fibrosis, interstitial lung disease, chronic interstitial lung disease, pneumoconiosis, silicosis, interstitial fibrosis, sarcoidosis, mediastinal fibrosis, cardiac fibrosis, atrial fibrosis, endomyocardial fibrosis, renal fibrosis, macular degeneration, keloid lesions, hypertrophic scar, nephrogenic systemic fibrosis, injection fibrosis, fibrotic complications of surgery, fibrotic chronic allograft vasculopathy, fibrosis associated with ischemic reperfusion injury, arthrofibrosis, Dupuytren's disease, fibrous proliferative lesions of the oral cavity, fibrosing intestinal strictures, glial scarring, leptomeningeal fibrosis, fibrosis due to radiation exposure, fibrosis due to mammary cystic rupture, myelofibrosis, retroperitoneal fibrosis, progressive massive fibrosis or any combination thereof.

In some other embodiments, said fibrosis, fibrotic condition or fibrotic symptom may be secondary to one or more of glycogen storage disease type III (GSD III), glycogen storage disease type VI (GSD VI), glycogen storage disease type IX (GSD IX), non-alcoholic steatohepatitis (NASH), cirrhosis, hepatitis, scleroderma, alcoholic fatty liver disease, atherosclerosis, asthma, cirrhosis of the gallbladder, diffuse parenchymal lung disease, interstitial pneumonitis, desquamative interstitial pneumonia, respiratory bronchiolitis, interstitial lung disease, chronic interstitial lung disease, acute interstitial pneumonitis, hypersensitivity pneumonitis, nonspecific interstitial pneumonia, cryptogenic organizing pneumonia, lymphocytic interstitial pneumonia, emphysema, chronic kidney disease, Type II diabetes, macular degeneration, chronic rejection in transplanted organs, post-vasectomy pain syndrome, rheumatoid arthritis, dermatomyositis-polymyositis, mixed connective tissue disease, Crohn's disease, meningitis, systemic lupus erythematosus, or symptoms or sequelae thereof, or other diseases or conditions resulting in the excessive deposition of extracellular matrix components, such as collagen, which may be affected by interventions within the TRβ pathway, or any combination thereof.

In some other embodiments, said fibrosis, fibrotic condition or fibrotic symptom may comprise a symptom or sequela of GSD III, GSD IX, Non Alcoholic Steatohepatitis, cirrhosis of the liver or pancreas, Dupuytren's disease, scleroderma, idiopathic pulmonary fibrosis, or alcoholic fatty liver disease, or any combination thereof.

The methods and compositions of the present disclosure may further comprise a method of treating a fibrosis, a fibrotic condition or a fibrotic symptom in a subject, comprising administering one or more of

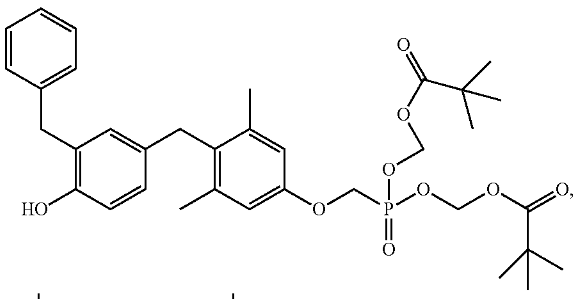

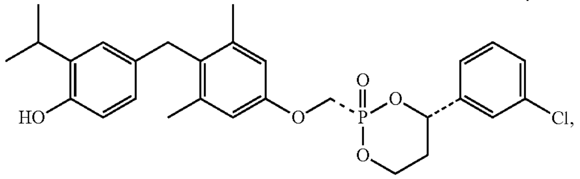

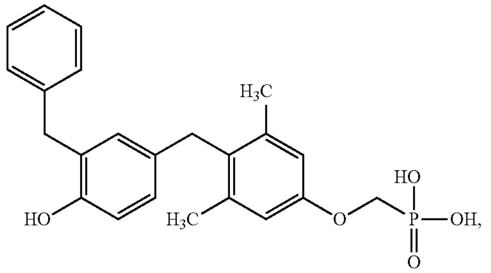

or

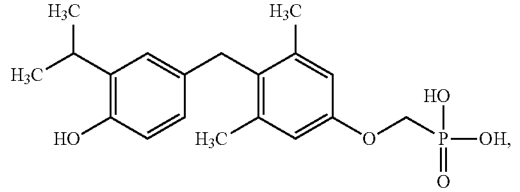

to a subject in need thereof.

The methods and compositions according to the present disclosure further provide for the administration of one or more of the compounds listed above to a subject, wherein said subject has one or more conditions selected from glycogen storage disease type III (GSD III), glycogen storage disease type VI (GSD VI), glycogen storage disease type IX (GSD IX), hepatitis, scleroderma, atherosclerosis, asthma, cardiac fibrosis, organ transplant fibrosis, muscle fibrosis, pancreatic fibrosis, bone-marrow fibrosis, liver fibrosis, cirrhosis of the gallbladder, fibrosis of the spleen, pulmonary fibrosis, idiopathic pulmonary fibrosis, diffuse parenchymal lung disease, idiopathic interstitial fibrosis, diffuse interstitial fibrosis, interstitial pneumonitis, desquamative interstitial pneumonia, respiratory bronchiolitis, interstitial lung disease, chronic interstitial lung disease, acute interstitial pneumonitis, hypersensitivity pneumonitis, nonspecific interstitial pneumonia, cryptogenic organizing pneumonia, lymphocytic interstitial pneumonia, pneumoconiosis, silicosis, emphysema, interstitial fibrosis, sarcoidosis, mediastinal fibrosis, cardiac fibrosis, atrial fibrosis, endomyocardial fibrosis, renal fibrosis, chronic kidney disease, Type II diabetes, macular degeneration, keloid lesions, hypertrophic scar, nephrogenic systemic fibrosis, injection fibrosis, complications of surgery, fibrotic chronic allograft vasculopathy and/or chronic rejection in transplanted organs, fibrosis associated with ischemic reperfusion injury, post-vasectomy pain syndrome, fibrosis associated with rheumatoid arthritis, arthrofibrosis, Dupuytren's disease, dermatomyositis-polymyositis, mixed connective tissue disease, fibrous proliferative lesions of the oral cavity, fibrosing intestinal strictures, Crohn's disease, glial scarring, leptomeningeal fibrosis, meningitis, systemic lupus erythematosus, fibrosis due to radiation exposure, fibrosis due to mammary cystic rupture, myelofibrosis, retroperitoneal fibrosis, progressive massive fibrosis, or symptoms or sequelae thereof, or other diseases or conditions resulting in the excessive deposition of extracellular matrix components, such as collagen, which may be affected by interventions within the TRβ pathway, or any combination thereof. The methods and compositions of the present disclosure contemplate said administration wherein the condition is a primary fibrosis, a secondary fibrosis, or a fibrotic symptom of a condition.

According to the methods and compositions of the present disclosure, a primary fibrosis may comprise one or more of scleroderma, atherosclerosis, cardiac fibrosis, organ transplant fibrosis, muscle fibrosis, pancreatic fibrosis, bone-marrow fibrosis, liver fibrosis, fibrosis of the spleen, pulmonary fibrosis, idiopathic pulmonary fibrosis, idiopathic interstitial fibrosis, diffuse interstitial fibrosis, interstitial lung disease, chronic interstitial lung disease, pneumoconiosis, silicosis, interstitial fibrosis, sarcoidosis, mediastinal fibrosis, cardiac fibrosis, atrial fibrosis, endomyocardial fibrosis, renal fibrosis, macular degeneration, keloid lesions, hypertrophic scar, nephrogenic systemic fibrosis, injection fibrosis, fibrotic complications of surgery, fibrotic chronic allograft vasculopathy, fibrosis associated with ischemic reperfusion injury, arthrofibrosis, Dupuytren's disease, fibrous proliferative lesions of the oral cavity, fibrosing intestinal strictures, glial scarring, leptomeningeal fibrosis, fibrosis due to radiation exposure, fibrosis due to mammary cystic rupture, myelofibrosis, retroperitoneal fibrosis, progressive massive fibrosis or any combination thereof.

According to the methods and compositions of the present disclosure, a secondary fibrosis may comprise a fibrosis associated with one or more of glycogen storage disease type III (GSD III), glycogen storage disease type VI (GSD VI), glycogen storage disease type IX (GSD IX), hepatitis, scleroderma, atherosclerosis, asthma, cirrhosis of the gallbladder, diffuse parenchymal lung disease, interstitial pneumonitis, desquamative interstitial pneumonia, respiratory bronchiolitis, interstitial lung disease, chronic interstitial lung disease, acute interstitial pneumonitis, hypersensitivity pneumonitis, nonspecific interstitial pneumonia, cryptogenic organizing pneumonia, lymphocytic interstitial pneumonia, emphysema, chronic kidney disease, Type II diabetes, macular degeneration, chronic rejection in transplanted organs, post-vasectomy pain syndrome, rheumatoid arthritis, dermatomyositis-polymyositis, mixed connective tissue disease, Crohn's disease, meningitis, systemic lupus erythematosus, or symptoms or sequelae thereof, or other diseases or conditions resulting in the excessive deposition of extracellular matrix components, such as collagen, which may be affected by interventions within the TRβ pathway, or any combination thereof.

According to the methods and compositions of the present disclosure, a primary fibrosis may comprise a symptom or sequela of GSD III, GSD IX, cirrhosis of the pancreas, Dupuytren's disease, scleroderma, idiopathic pulmonary fibrosis, or alcoholic fatty liver disease, or any combination thereof.

According to the methods and compositions of the present disclosure, the compositions to be administered may further comprise one or more pharmaceutically acceptable excipients, and may be formulated for oral, intravenous, intraarterial, intestinal, rectal, vaginal, nasal, pulmonary, topical, intradermal, transdermal, transbuccal, translingual, sublingual, or opthalmic administration, or any combination thereof.

According to the methods and compositions of the present disclosure, a subject to which the compositions listed above are to be administered may show abnormal or excessive deposition of collagen type 1, 1a, or III. In some embodiments according to the methods and compositions of the present disclosure, administration of said composition results in the prevention, amelioration, or cure of said fibrosis, fibrotic condition, or fibrotic symptom, and may further result in the reduction in the amount of extracellular matrix proteins present in one or more tissues of said subject. In some embodiments, said reduction in the amount of extracellular matrix proteins present in one or more tissues of said subject may comprise a reduction in the amount of collagen present in one or more tissues of said subject, and may further comprise a reduction in the amount of Type I, Type Ia, or Type III collagen present in one or more tissues of said subject.

DETAILED DESCRIPTION

Figure 1:
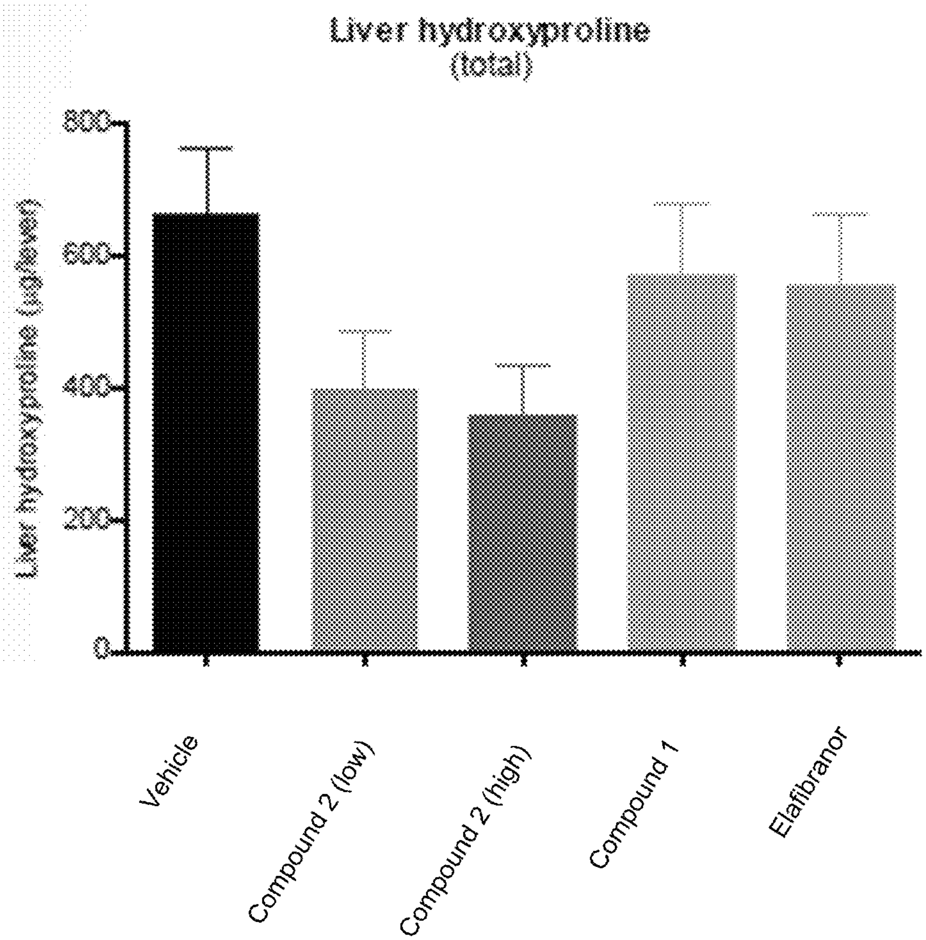
FIG. 1 shows total liver hydroxyproline content in mice following 8 weeks of treatment with vehicle, low dose Compound 2 (see Example 1), high dose Compound 2 (see Example 1), Compound 1, or elafibranor (control). Compound 2-treated animals show lower total liver hydroxyproline levels than control-treated or mock-treated animals.

The present disclosure provides compounds and methods for treating fibrosis, fibrotic conditions, or fibrotic symptoms by administering thyroid hormone receptor-β (TRβ) agonists. In some embodiments, such fibrosis, fibrotic conditions, or conditions giving rise to fibrotic symptoms may include glycogen storage disease type III (GSD III), glycogen storage disease type VI (GSD VI), glycogen storage disease type IX (GSD IX), non-alcoholic steatohepatitis (NASH), cirrhosis, hepatitis, scleroderma, alcoholic fatty liver disease, atherosclerosis, asthma, cardiac fibrosis, organ transplant fibrosis, muscle fibrosis, pancreatic fibrosis, bone-marrow fibrosis, liver fibrosis, cirrhosis of liver and gallbladder, fibrosis of the spleen, scleroderma, pulmonary fibrosis, idiopathic pulmonary fibrosis, diffuse parenchymal lung disease, idiopathic interstitial fibrosis, diffuse interstitial fibrosis, interstitial pneumonitis, desquamative interstitial pneumonia, respiratory bronchiolitis, interstitial lung disease, chronic interstitial lung disease, acute interstitial pneumonitis, hypersensitivity pneumonitis, nonspecific interstitial pneumonia, cryptogenic organizing pneumonia, lymphocytic interstitial pneumonia, pneumoconiosis, silicosis, emphysema, interstitial fibrosis, sarcoidosis, mediastinal fibrosis, cardiac fibrosis, atrial fibrosis, endomyocardial fibrosis, renal fibrosis, chronic kidney disease, Type II diabetes, macular degeneration, keloid lesions, hypertrophic scar, nephrogenic systemic fibrosis, injection fibrosis, complications of surgery, fibrotic chronic allograft vasculopathy and/or chronic rejection in transplanted organs, fibrosis associated with ischemic reperfusion injury, post-vasectomy pain syndrome, fibrosis associated with rheumatoid arthritis, arthrofibrosis, Dupuytren's disease, dermatomyositis-polymyositis, mixed connective tissue disease, fibrous proliferative lesions of the oral cavity, fibrosing intestinal strictures, Crohn's disease, glial scarring, leptomeningeal fibrosis, meningitis, systemic lupus erythematosus, fibrosis due to radiation exposure, fibrosis due to mammary cystic rupture, myelofibrosis, retroperitoneal fibrosis, progressive massive fibrosis, or symptoms or sequelae thereof, or other diseases or conditions resulting in the excessive deposition of extracellular matrix components, such as collagen, which may be affected by interventions within the TRβ pathway. Such conditions may be associated with inflammation and/or injury, and further may involve responses mediated by TGF-β-dependent pathways which can be modulated by thyroid hormones (see, e.g., Alfonso-Merino et al., Proc. Nat. Acad. Sci. 113(24):E3451-60 (2016), which is incorporated herein for its disclosure of the ability of thyroid hormones to modulate TGF-β signaling and related fibrosis in mice). Because TGF-β-dependent pathways are implicated in fibroblast differentiation and the stimulation of collagen production, and thyroid hormones such as T3 and T4 may impinge on these pathways via the TRβ receptor, the present disclosure provides compositions and methods for the prevention, amelioration, or reduction in collagen deposition in one or more tissues of a subject by administering TRβ agonist compounds.

Definitions

The term "mammal" is used in its usual biological sense. Thus, it specifically includes humans and non-human mammals such as dogs, cats, horses, donkeys, mules, cows, domestic buffaloes, camels, llamas, alpacas, bison, yaks, goats, sheep, pigs, elk, deer, domestic antelopes, and non-human primates as well as many other species.

"Subject" as used herein, means a human or a non-human mammal including but not limited to a dog, cat, horse, donkey, mule, cow, domestic buffalo, camel, llama, alpaca, bison, yak, goat, sheep, pig, elk, deer, domestic antelope, or a non-human primate selected for treatment or therapy.

"Subject suspected of having" means a subject exhibiting one or more clinical indicators of a disease or condition. In certain embodiments, the disease or condition is one or more fibroses, fibrotic conditions, or fibrotic symptoms. In certain embodiments, the disease or condition is scleroderma. In certain embodiments, the disease or condition is non-alcoholic steatohepatitis. In certain embodiments, the disease or condition is cirrhosis. In certain embodiments, the disease or condition is non-alcoholic fatty liver disease. In certain embodiments, the disease or condition is idiopathic pulmonary fibrosis. In certain embodiments, the disease or condition is atherosclerosis. In certain embodiments, the disease or condition is hepatitis, alcoholic fatty liver disease, asthma, cardiac fibrosis, organ transplant fibrosis, muscle fibrosis, pancreatic fibrosis, bone-marrow fibrosis, liver fibrosis, cirrhosis of liver and gallbladder, fibrosis of the spleen, scleroderma, pulmonary fibrosis, diffuse parenchymal lung disease, idiopathic interstitial fibrosis, diffuse interstitial fibrosis; interstitial pneumonitis, desquamative interstitial pneumonia, respiratory bronchiolitis, interstitial lung disease, chronic interstitial lung disease, acute interstitial pneumonitis, hypersensitivity pneumonitis, nonspecific interstitial pneumonia, cryptogenic organizing pneumonia, lymphocytic interstitial pneumonia, pneumoconiosis, silicosis, emphysema, interstitial fibrosis, sarcoidosis, mediastinal fibrosis, cardiac fibrosis, atrial fibrosis, endomyocardial fibrosis, renal fibrosis, chronic kidney disease, Type II diabetes, macular degeneration, keloid lesions, hypertrophic scar, nephrogenic systemic fibrosis, injection fibrosis, complications of surgery, fibrotic chronic allograft vasculopathy and/or chronic rejection in transplanted organs, fibrosis associated with ischemic reperfusion injury, post-vasectomy pain syndrome, fibrosis associated with rheumatoid arthritis, arthrofibrosis, Dupuytren's disease, dermatomyositis-polymyositis, mixed connective tissue disease, fibrous proliferative lesions of the oral cavity, fibrosing intestinal strictures, Crohn's disease, glial scarring, leptomeningeal fibrosis, meningitis, systemic lupus erythematosus, fibrosis due to radiation exposure, fibrosis due to mammary cystic rupture, myelofibrosis, retroperitoneal fibrosis, progressive massive fibrosis, or symptoms or sequelae thereof, or other diseases or conditions resulting in the excessive deposition of extracellular matrix components.

As used herein, "fibrosis" refers to the abnormal deposition of extracellular matrix proteins. Such proteins include but are not limited to collagen, elastin, fibronectin, laminin, keratin, keratin, keratin sulfate, fibrin, perlecan, agrin, or agrecan. As used herein, "collagen" refers to any one of the subtypes of collagen, including but not limited to Type I, II, III, IV, V, VI, VII, VIII, IX, X, XI, XII, XIII, XIV, XV, XVI, XVII, or XVIII. Exemplary collagen types and subtypes especially include Type I, Type Ia, Type II, Type III, Type IV, and Type V. As used herein, fibrosis may occur by itself or as a symptom or sequela of another condition. As used herein, fibrosis may result from a genetic condition, a genetic predisposition, an environmental insult, an injury, healing of an injury, an autoimmune condition, or a chronic inflammation, a chronic inflammatory condition, or another condition leading to abnormal or excessive deposition of extracellular matrix components. Fibrosis as referred to herein may be assessed by assaying for, or determining the presence or level of, one or more biomarkers. Biomarkers for the presence of fibrosis include, but are not limited to, expression of the Cola1, Col3a1, αSMA, and/or Galectin1 genes or any combination or product thereof. Diagnosis or assessment of fibrosis may further be made by determination of the presence or level of type I collagen and/or hydroxyproline or any combination or product thereof. Diagnosis or assessment of fibrosis may also be made by histological, histochemical, or immunohistochemical analysis of one or more samples from a subject.

"Glycogen storage disease" means any one or more of a group of disorders marked by dysfunction in the synthesis, transport, or utilization of glycogen, generally due to the loss of a necessary enzyme activity. Glycogen storage diseases are generally classified by type according to their symptoms and etiologies. Known types include GSD type 0 (aglycogenesis, glycogen synthase deficiency); GSD type 1 (von Gierke disease, glucose-6-phosphatase translocase/transporter deficiency, GSD I); GSD type 2 (Pompe disease, alpha-1-4-glucosidase deficiency, GSD II); GSD type 3 (Cori disease, Forbes disease, limit dextrinosis, debranching enzyme disease; amylo-1-6-glucosidase deficiency due to loss of glucosidase, and/or transferase activity, GSD III); GSD type 4 (Andersen disease, glycogen phosphorylase deficiency, brancher deficiency, amylopectinosis, glycogen branching enzyme deficiency; amylo-1,4 to 1,6 transglucosidase deficiency, GSD IV); GSD type 5 (McArdle disease; glycogen phosphorylase (muscle type) deficiency, GSD V); GSD type 6 (Hers disease; glycogen phosphorylase E (liver type) deficiency, GSD VI); GSD type 7 (Tarui disease; phosphofructokinase deficiency, GSD VII); GSD type 8, 9 (GSD with phosphorylase activation system defects; phosphorylase kinase (liver or muscle isoforms) deficiency, GSD VIII and GSD IX); GSD type 10 (cyclic AMP-dependent kinase deficiency, GSD X); GSD type 11 (Fanconi-Bickel syndrome; glucose transporter type 2 (GLUT2) deficiency, GSD XI); and GSD type 12 (aldolase A deficiency, GSD XII). Subtypes of glycogen storage diseases are also known, in particular GSD 1a, which results from mutations in the gene for glucose-6-phosphatase (G6PC) and leads to, among other symptoms, the excess accumulation of glycogen and lipids in liver tissue, hepatomegaly, hepatic adenomas, and hepatocellular carcinoma. Symptoms of glycogen storage diseases may include elevated or reduced blood sugar, insulin insensitivity, myopathies, as well as hepatic symptoms such as steatosis, hyperlipidemia, hypercholesterolemia, cardiomegaly, hepatomegaly, fibrosis, cirrhosis, hepatocellular adenoma, and hepatocellular carcinoma. Symptoms may also include insulin insensitivity, elevated or reduced blood glucose, renal dysfunction, and/or fibrosis.

"Subject in need thereof" means a subject identified as in need of a therapy or treatment.

A therapeutic effect relieves, to some extent, one or more of the symptoms of a disease or disorder, and includes curing the disease or disorder. "Curing" means that the symptoms of active disease are eliminated. However, certain long-term or permanent effects of the disease may exist even after a cure is obtained (such as extensive tissue damage).

"Treat," "treatment," or "treating," as used herein refers to administering a pharmaceutical composition for prophylactic and/or therapeutic purposes. The term "prophylactic treatment" refers to treating a patient who does not yet have the relevant disease or disorder, but who is susceptible to, or otherwise at risk of, a particular disease or disorder, whereby the treatment reduces the likelihood that the patient will develop the disease or disorder. The term "therapeutic treatment" refers to administering treatment to a patient already having a disease or disorder.

"Preventing" or "prevention" refers to delaying or forestalling the onset, development or progression of a condition or disease for a period of time, including weeks, months, or years.

"Amelioration" means a lessening of severity of at least one indicator of a condition or disease. In certain embodiments, amelioration includes a delay or slowing in the progression of one or more indicators of a condition or disease. The severity of indicators may be determined by subjective or objective measures which are known to those skilled in the art "Modulation" means a perturbation of function or activity. In certain embodiments, modulation means an increase in gene expression. In certain embodiments, modulation means a decrease in gene expression. In certain embodiments, modulation means an increase or decrease in total serum levels of a specific protein. In certain embodiments, modulation means an increase or decrease in free serum levels of a specific protein. In certain embodiments, modulation means an increase or decrease in total serum levels of a specific non-protein factor. In certain embodiments, modulation means an increase or decrease in free serum levels of a specific non-protein factor. In certain embodiments, modulation means an increase or decrease in total bioavailability of a specific protein. In certain embodiments, modulation means an increase or decrease in total bioavailability of a specific non-protein factor.

"Administering" means providing a pharmaceutical agent or composition to a subject, and includes, but is not limited to, administering by a medical professional and self-administering.

Administration of the compounds disclosed herein or the pharmaceutically acceptable salts thereof can be via any of the accepted modes of administration for agents that serve similar utilities including, but not limited to, orally, subcutaneously, intravenously, intranasally, topically, transdermally, intraperitoneally, intramuscularly, intrapulmonarilly, vaginally, rectally, or intraocularly. Oral and parenteral administrations are customary in treating the indications that are the subject of the preferred embodiments.

"Parenteral administration," means administration through injection or infusion. Parenteral administration includes, but is not limited to, subcutaneous administration, intravenous administration, intramuscular administration, intraarterial administration, and intracranial administration.

"Subcutaneous administration" means administration just below the skin.

"Intravenous administration" means administration into a vein.

"Intraarterial administration" means administration into an artery.

The term "agent" includes any substance, molecule, element, compound, entity, or a combination thereof. It includes, but is not limited to, e.g., protein, polypeptide, peptide or mimetic, small organic molecule, polysaccharide, polynucleotide, and the like. It can be a natural product, a synthetic compound, or a chemical compound, or a combination of two or more substances.

"Pharmaceutical agent" means a substance that provides a therapeutic effect when administered to a subject.

"Pharmaceutical composition" means a mixture of substances suitable for administering to an individual that includes a pharmaceutical agent. For example, a pharmaceutical composition may comprise a modified oligonucleotide and a sterile aqueous solution.

"Active pharmaceutical ingredient" means the substance in a pharmaceutical composition that provides a desired effect.

The term "pharmaceutically acceptable salt" refers to salts that retain the biological effectiveness and properties of the compounds with which they are associated and, which are not biologically or otherwise undesirable. In many cases, the compounds herein are capable of forming acid and/or base salts by virtue of the presence of phenol and/or phosphonate groups or groups similar thereto. One of ordinary skill in the art will be aware that the protonation state of any or all of these compounds may vary with pH and ionic character of the surrounding solution, and thus the present disclosure contemplates multiple charge states of each compound. Pharmaceutically acceptable acid addition salts can be formed with inorganic acids and organic acids. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Pharmaceutically acceptable base addition salts can be formed with inorganic and organic bases. Inorganic bases from which salts can be derived include, for example, sodium, potassium, lithium, ammonium, calcium, magnesium, iron, zinc, copper, manganese, aluminum, and the like; particularly preferred are the ammonium, potassium, sodium, calcium and magnesium salts. Organic bases from which salts can be derived include, for example, primary, secondary, and tertiary amines, substituted amines including naturally occurring substituted amines, cyclic amines, basic ion exchange resins, and the like, specifically such as isopropylamine, trimethylamine, diethylamine, triethylamine, tripropylamine, and ethanolamine. Many such salts are known in the art, as described in WO 87/05297, Johnston et al., published Sep. 11, 1987 (incorporated by reference herein in its entirety).

"Solvate" refers to the compound formed by the interaction of a solvent and an EPI, a metabolite, or salt thereof. Suitable solvates are pharmaceutically acceptable solvates including hydrates.

The term "atherosclerosis" refers to a condition characterized by irregularly distributed lipid deposits in the intima of large and medium-sized arteries wherein such deposits provoke fibrosis and calcification. Atherosclerosis raises the risk of angina, stroke, heart attack, or other cardiac or cardiovascular conditions.

Compounds

In some embodiments, the TRβ agonists for use as described herein include compounds according to Formula I:

Formula I

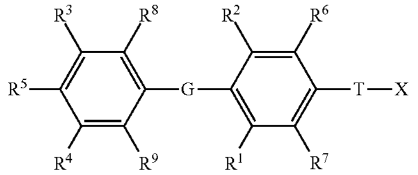

wherein:

- G is selected from the group consisting of —O—, —S—, —S(═O)—, —S(═)$_2$—, —Se—, —$CH_2$—, —$CF_2$—, —CHF—, —C(O)—, —CH(OH)—, —CH($_1$-$C_4$ alkyl)-, —CH($C_1$-$C_4$ alkoxy)-, —C(═$CH_2$)—, —NH—, and —N($C_1$-$C_4$ alkyl)-;
- T is selected from the group consisting of —$(CR^a_2)_k$—, —$CR^b$═$CR^b$—$(CR^a_2)_n$—, —$(CR^a_2)_n$—$CR^b$═$CR^b$—, —$(CR^a_2)$—$CR^b$═$CR^b$—$(CR^a_2)$—, —O$(CR^b_2)(CR^a_2)_n$—, —S$(CR^b_2)(CR^a_2)$n-, N$(R^c)(CR^b_2)(CR^a_2)_n$—, N$(R^b)$C(O)$(CR^a_2)_n$, —C(O)$(CR^a_2)_m$—, —$(CR^a_2)_m$C(O)—, —$(CR^a_2)$C(O)$(CR^a_2)_n$, —$(CR^a_2)_n$C(O)$(CR^a_2)$—, and —C(O)NH$(CR^b_2)(CR^a_2)$p—;
- k is an integer from 1-4;
- m is an integer from 0-3;
- n is an integer from 0-2;
- p is an integer from 0-1;
- each $R^a$ is independently selected from the group consisting of hydrogen, optionally substituted —$C_1$-$C_4$ alkyl, halogen, —OH, optionally substituted —O—$C_1$-$C_4$ alkyl, —$OCF_3$, optionally substituted —S—$C_1$-$C_4$ alkyl, —$NR^bR^c$, optionally substituted —$C_2$- $C_4$ alkenyl, and optionally substituted —$C_2$-$C_4$ alkynyl; with the proviso that when one $R^a$ is attached to C through an O, S, or N atom, then the other $R^a$ attached to the same C is a hydrogen, or attached via a carbon atom;
- each $R^b$ is independently selected from the group consisting of hydrogen and optionally substituted —$C_1$-$C_4$ alkyl;
- each $R^c$ is independently selected from the group consisting of hydrogen and optionally substituted —$C_1$-$C_4$ alkyl, optionally substituted —C(O)—$C_1$-$C_4$ alkyl, and —C(O)H;
- $R^1$, and $R^2$ are each independently selected from the group consisting of halogen, optionally substituted —$C_1$-$C_4$ alkyl, optionally substituted —S—$C_1$-$C_3$ alkyl, optionally substituted —$C_2$-$C_4$ alkenyl, optionally substituted —$C_2$-$C_4$ alkynyl, —$CF_3$, —$OCF_3$, optionally substituted-O—$C_1$-$C_3$ alkyl, and cyano;
- $R^6$, $R^7$, $R^8$, and $R^9$ are each independently selected from the group consisting of are each independently selected from the group consisting of hydrogen, halogen, optionally substituted —C $C_1$-$C_4$ alkyl, optionally substituted —S—$C_1$-$C_3$ alkyl, optionally substituted —$C_2$-$C_4$ alkenyl, optionally substituted —$C_2$-$C_4$ alkynyl, —$CF_3$, —$OCF_3$, optionally substituted-O—$C_1$-$C_3$ alkyl, and cyano; or $R^6$ and T are taken together along with the carbons they are attached to form a ring of 5 to 6 atoms including 0 to 2 heteroatoms independently selected from —$NR^i$—, —O—, and —S—, with the proviso that when there are 2 heteroatoms in the ring and both heteroatoms are different than nitrogen then both heteroatoms have to be separated by at least one carbon atom; and X is attached to this ring by a direct bond to a ring carbon, or by —$(CR^a_2)$— or —C(O)— bonded to a ring carbon or a ring nitrogen;
- $R^i$ is selected from the group consisting of hydrogen, —C(O)$C_1$-$C_4$ alkyl, —$C_1$-$C_4$ alkyl, and —$C_1$-$C_4$-aryl;
- $R^3$ and $R^4$ are independently selected from the group consisting of hydrogen, halogen, —$CF_3$, —$OCF_3$, cyano, optionally substituted —$C_1$-$C_{12}$ alkyl, optionally substituted —$C_2$-$C_{12}$ alkenyl, optionally substituted —$C_2$-$C_{12}$ alkynyl, —$SR^d$, —S(═O)$R^e$, —S(═O)$_2R^e$, —S(═O)$_2NR^fR^g$, —C(O)$OR^h$, —C(O)$R^e$, —N$(R^b)$C(O)$NR^fR^g$, —N$(R^b)$S(═O)$_2R^e$, —N$(R^b)$S(═O)$_2NR^fR^g$, and $NR^fR^g$;
- each $R^d$ is selected from the group consisting of optionally substituted —$C_1$-$C_{12}$ alkyl, optionally substituted —$C_2$-$C_{12}$ alkenyl, optionally substituted —$C_2$-$C_{12}$ alkynyl, optionally substituted —$(CR^b_2)_n$ aryl, optionally substituted —$(CR^b_2)_n$ cycloalkyl, optionally substituted —$(CR^b_2)_n$ heterocycloalkyl, and —C(O)$NR^fR^g$;
- each $R^e$ is selected from the group consisting of optionally substituted —$C_1$-$C_{12}$ alkyl, optionally substituted —$C_2$-$C_{12}$ alkenyl, optionally substituted —$C_2$-$C_{12}$ alkynyl, optionally substituted —$(CR^a_2)_n$ aryl, optionally substituted —$(CR^a_2)_n$ cycloalkyl, and optionally substituted —$(CR^a_2)_n$ heterocycloalkyl;
- $R^f$ and $R^g$ are each independently selected from the group consisting of hydrogen, optionally substituted —$C_1$-$C_{12}$ alkyl, optionally substituted —$C_2$-$C_{12}$ alkenyl, optionally substituted —$C_2$-$C_{12}$ alkynyl, optionally substituted —$(CR^b_2)_n$ aryl, optionally substituted —$(CR^b_2)_n$ cycloalkyl, and optionally substituted —$(CR^b_2)_n$ heterocycloalkyl, or $R^f$ and $R^g$ may together form an optionally substituted heterocyclic ring, which may contain a second heterogroup selected from the group consisting of O, $NR^c$, and S, wherein said optionally substituted heterocyclic ring may be substituted with 0-4 substituents selected from the group consisting of optionally substituted —$C_1$-$C_4$ alkyl, —$OR^b$, oxo, cyano, —$CF_3$, optionally substituted phenyl, and —C(O)$OR^h$;
- each $R^h$ is selected from the group consisting of optionally substituted —$C_1$-$C_{12}$ alkyl, optionally substituted —$C_2$-$C_{12}$ alkenyl, optionally substituted —$C_2$-$C_{12}$ alkynyl, optionally substituted —$(CR^b{}_2)_n$ aryl, optionally substituted —$(CR^b{}_2)_n$ cycloalkyl, and optionally substituted —$(CR^b{}_2)_n$ heterocycloalkyl;

$R^5$ is selected from the group consisting of —OH, optionally substituted —$OC_1$-$C_6$ alkyl, $OC(O)R^e$, —OC(O)$OR^h$, —F, —$NHC(O)R^e$, —NHS(═O)$R^e$, —NHS(═O)$_2R^e$, —NHC(═S)$NH(R^h)$, and —NHC(O)NH$(R^h)$;

X is $P(O)YR^{11}Y'R^{11}$;

Y and Y' are each independently selected from the group consisting of —O—, and —$NR^v$—; when Y and Y' are —O—, $R^{11}$ attached to —O— is independently selected from the group consisting of —H, alkyl, optionally substituted aryl, optionally substituted heterocycloalkyl, optionally substituted $CH_2$-heterocycloakyl wherein the cyclic moiety contains a carbonate or thiocarbonate, optionally substituted -alkylaryl, —$C(R^z)_2OC(O)NR^z{}_2$, —$NR^z$—C(O)—$R^y$, —$C(R^z)_2$—$OC(O)R^y$, —$C(R^z)_2$—O—$C(O)OR^y$, —$C(R^z)_2OC(O)SR^y$, —alkyl-S—$C(O)R^y$, -alkyl-S—S-alkylhydroxy, and -alkyl-S—S—S-alkylhydroxy;

when Y and Y' are —$NR^v$—, then $R^{11}$ attached to —$NR^v$— is independently selected from the group consisting of —H, —$[C(R^z)_2]_q$—$COOR^y$, —$C(R^x)_2COOR^Y$, —$[C(R^z)_2]_q$—$C(O)SR^y$, and -cycloalkylene-$COOR^y$;

when Y is —O— and Y' is $NR^v$, then $R^{11}$ attached to —O— is independently selected from the group consisting of —H, alkyl, optionally substituted aryl, optionally substituted heterocycloalkyl, optionally substituted $CH_2$-heterocycloakyl wherein the cyclic moiety contains a carbonate or thiocarbonate, optionally substituted -alkylaryl, —$C(R^z)_2OC(O)NR^z{}_2$, —$NR^z$—C(O)—$R^y$, —$C(R^z)_2$—$OC(O)R^y$, —C—$(R^z)_2$—O—C(O)$OR^y$, —$C(R^z)_2OC(O)SR^y$, -alkyl-S—$C(O)R^y$, -alkyl-S—S-alkylhydroxy, and -alkyl-S—S—S-alkylhydroxy; and $R^{11}$ attached to —$NR^v$— is independently selected from the group consisting of H, —$[C(R^z)_2]_q$—$COOR^y$, —$C(R^x)_2COOR^y$, —$[C(R^z)_2]_q$—$C(O)SR^y$, and -cycloalkylene-$COOR^y$;

or when Y and Y' are independently selected from —O— and $NR^v$, then together $R^{11}$ and $R^{11}$ are -alkyl-S—S-alkyl- to form a cyclic group, or together $R^{11}$ and $R^{11}$ are the group:

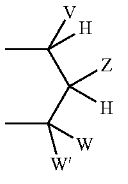

wherein:

V, W, and W' are independently selected from the group consisting of hydrogen, optionally substituted alkyl, optionally substituted aralkyl, heterocycloalkyl, aryl, substituted aryl, heteroaryl, substituted heteroaryl, optionally substituted 1-alkenyl, and optionally substituted 1-alkynyl;

or together V and Z are connected via an additional 3-5 atoms to form a cyclic group containing 5-7 atoms, wherein 0-1 atoms are heteroatoms and the remaining atoms are carbon, substituted with hydroxy, acyloxy, alkylthiocarbonyloxy, alkoxycarbonyloxy, or aryloxycarbonyloxy attached to a carbon atom that is three atoms from both Y groups attached to the phosphorus;

or together V and Z are connected via an additional 3-5 atoms to form a cyclic group, wherein 0-1 atoms are heteroatoms and the remaining atoms are carbon, that is fused to an aryl group at the beta and gamma position to the Y attached to the phosphorus;

or together V and W are connected via an additional 3 carbon atoms to form an optionally substituted cyclic group containing 6 carbon atoms and substituted with one substituent selected from the group consisting of hydroxy, acyloxy, alkoxycarbonyloxy, alkylthiocarbonyloxy, and aryloxycarbonyloxy, attached to one of said carbon atoms that is three atoms from a Y attached to the phosphorus;

or together Z and W are connected via an additional 3-5 atoms to form a cyclic group, wherein 0-1 atoms are heteroatoms and the remaining atoms are carbon, and V must be aryl, substituted aryl, heteroaryl, or substituted heteroaryl;

or together W and W' are connected via an additional 2-5 atoms to form a cyclic group, wherein 0-2 atoms are heteroatoms and the remaining atoms are carbon, and V must be aryl, substituted aryl, heteroaryl, or substituted heteroaryl;

Z is selected from the group consisting of —$CHR^zOH$, —$CHR^zOC(O)R^y$, —$CHR^zOC(S)R^y$, —$CHR^zOC(S)OR^y$, —$CHR^zOC(O)SR^y$, —$CHR^zOCO_2R^y$, —$OR^z$, —$SR^z$, —$CHR^zN_3$, —$CH_2$-aryl, —CH(aryl)OH, —CH$(CH{=}CR^z{}_2)$OH, —CH$(C{\equiv}CR^z)$OH, —$R^z$, —$NR^z{}_2$, —$OCOR^y$, —$OCO_2R^y$, —$SCOR^y$, —$SCO_2R^y$, —$NHCOR^z$, —$NHCO_2R^y$, —$CH_2$NH-aryl, —$(CH_2)$q-$OR^z$, and —$(CH_2)$q-$SR^z$;

q is an integer 2 or 3;

each $R^z$ is selected from the group consisting of $R^y$ and —H;

each $R^y$ is selected from the group consisting of alkyl, aryl, heterocycloalkyl, and aralkyl;

each $R^x$ is independently selected from the group consisting of —H, and alkyl, or together $R^x$ and $R^x$ form a cyclic alkyl group;

each $R^v$ is selected from the group consisting of —H, lower alkyl, acyloxyalkyl, alkoxycarbonyloxyalkyl, and lower acyl;

and pharmaceutically acceptable salts thereof.

In some embodiments, the compound of Formula I has the following provisos:

a) when G is —O—, T is —$CH_2$—, $R^1$ and $R^2$ are each bromo, $R^3$ is iso-propyl, $R^4$ is hydrogen, and $R^5$ is —OH, then X is not $P(O)(OH)_2$ or $P(O)(OCH_2CH_3)_2$;

b) V, Z, W, W' are not all —H; and c) when Z is —$R^z$, then at least one of V, W, and W' is not —H, alkyl, aralkyl, or heterocycloalkyl;

d) when G is —O—, T is —$(CH_2)_{1-4}$—, $R^1$ and $R^2$ are independently halogen, alkyl, and cycloalkyl, $R^3$ is alkyl, $R^4$ is hydrogen, and $R^5$ is —OH, then X is not —$P(O)(OH)_2$ or —P(O))(O)-lower alkyl$)_2$; and e) when G is —O—, $R^5$ is —$NHC(O)R^e$, —NHS(═O)$_{1-2}R^e$, —$NHC(S)NH(R^b)$, or —$NHC(O)NH(R^h)$, T is —$(CH_2)^m$—, —CH═CH—, —$O(CH_2)_{1-2}$—, or —$NH(CH_2)_{1-2}$—, then X is not —$P(OX(OH)_2$ or —$P(O)(OH)NH_2$.

In some embodiments, the compound is selected from one or more of the following:

(Compound 1)
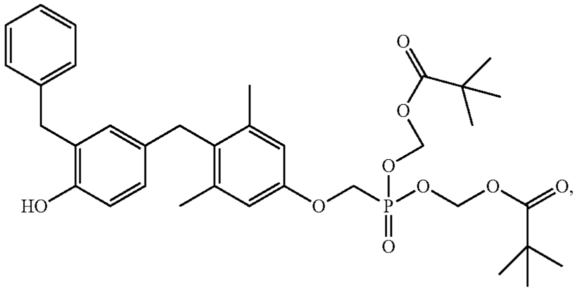
(Compound 2)
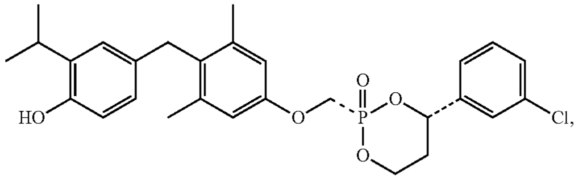
-continued
(Compound 3)
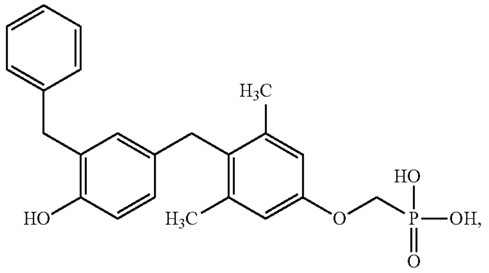
or
(Compound 4)
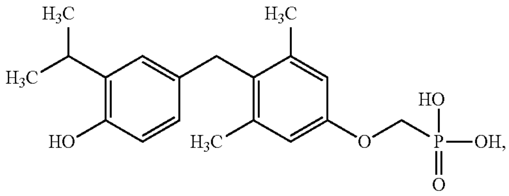
or pharmaceutically acceptable salts thereof.
In other embodiments, the compound is selected from:
| Structure | Compound Number |
|---|---|
| 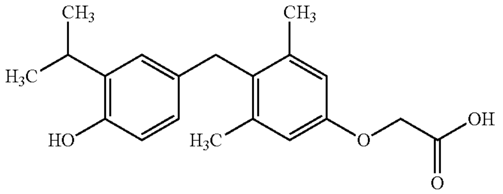 [SMILES: Cc1cc(OCC(=O)O)cc(C)c1Cc1ccc(O)c(C(C)C)c1] | 17 |
| 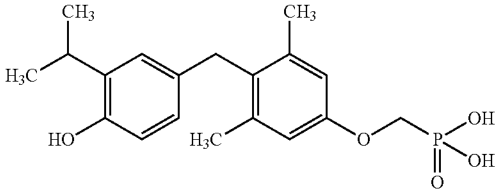 [SMILES: Cc1cc(OCP(=O)(O)O)cc(C)c1Cc1ccc(O)c(C(C)C)c1] | 7 |
| 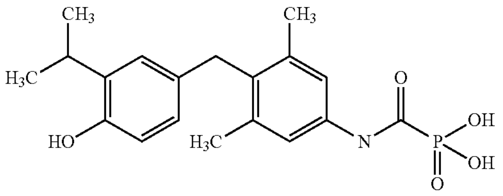 [SMILES: Cc1cc(NC(=O)P(=O)(O)O)cc(C)c1Cc1ccc(O)c(C(C)C)c1] | 1a |
| 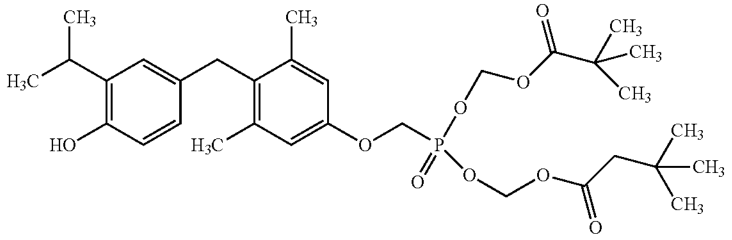 [SMILES: Cc1cc(OCP(=O)(OCOC(=O)CC(C)(C)C)OCOC(=O)C(C)(C)C)cc(C)c1Cc1ccc(O)c(C(C)C)c1] | 12-1 |

-continued
| Structure | Compound Number |
|---|---|
| 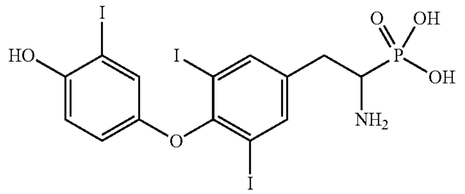 [SMILES: NC(Cc1cc(I)c(Oc2ccc(O)c(I)c2)c(I)c1)P(=O)(O)O] | 2a |
| 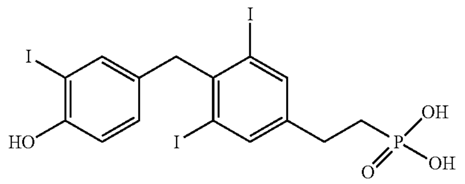 [SMILES: O=P(O)(O)CCc1cc(I)c(Cc2ccc(O)c(I)c2)c(I)c1] | 3a |
| 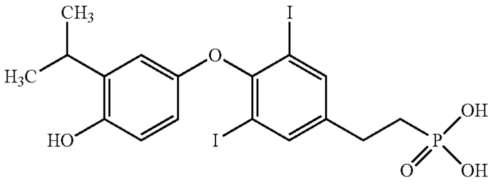 [SMILES: CC(C)c1cc(Oc2c(I)cc(CCP(=O)(O)O)cc2I)ccc1O] | 4a |
| 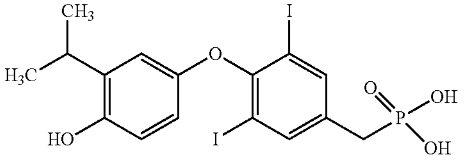 [SMILES: CC(C)c1cc(Oc2c(I)cc(CP(=O)(O)O)cc2I)ccc1O] | 5 |
| 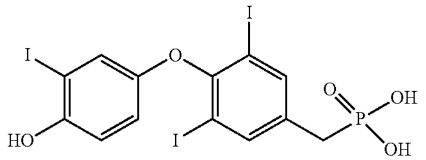 [SMILES: O=P(O)(O)Cc1cc(I)c(Oc2ccc(O)c(I)c2)c(I)c1] | 6 |
| 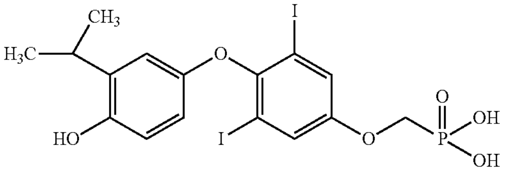 [SMILES: CC(C)c1cc(Oc2c(I)cc(OCP(=O)(O)O)cc2I)ccc1O] | 8 |
| 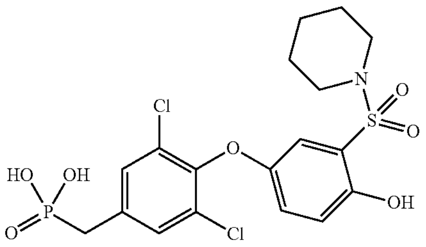 [SMILES: O=P(O)(O)Cc1cc(Cl)c(Oc2ccc(O)c(S(=O)(=O)N3CCCCC3)c2)c(Cl)c1] | 9 |

-continued
| Structure | Compound Number |
|---|---|
| 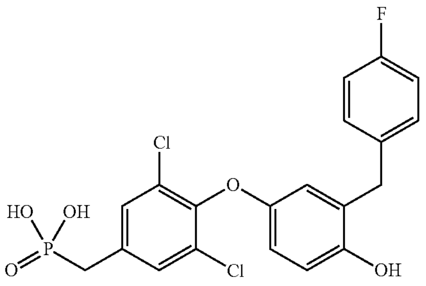 [SMILES: O=P(O)(O)Cc1cc(Cl)c(Oc2ccc(O)c(Cc3ccc(F)cc3)c2)c(Cl)c1] | 11 |
| 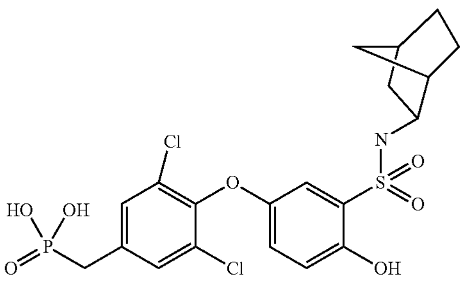 [SMILES: O=P(O)(O)Cc1cc(Cl)c(Oc2ccc(O)c(S(=O)(=O)NC3CC4CCC3C4)c2)c(Cl)c1] | 10 |
| 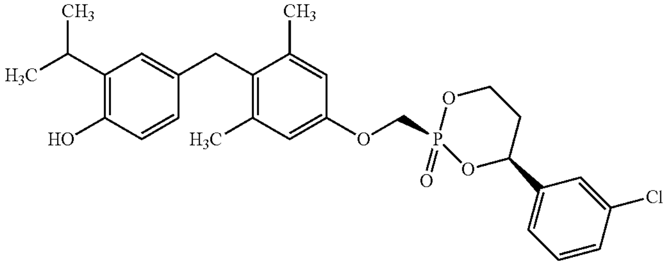 [SMILES: Cc1cc(OC[P@@]2(=O)OCC[C@@H](c3cccc(Cl)c3)O2)cc(C)c1Cc1ccc(O)c(C(C)C)c1] | cis-13-1 |
| 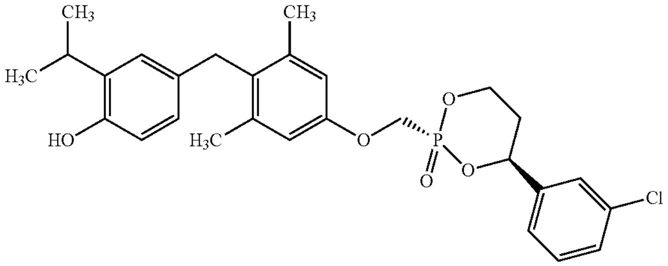 [SMILES: Cc1cc(OC[P@]2(=O)OCC[C@@H](c3cccc(Cl)c3)O2)cc(C)c1Cc1ccc(O)c(C(C)C)c1] | trans-13-1 |
| 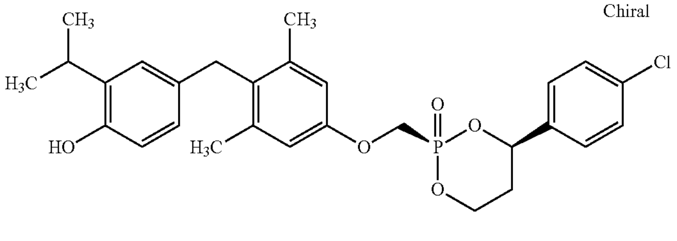 [SMILES: Cc1cc(OC[P@]2(=O)OCC[C@H](c3ccc(Cl)cc3)O2)cc(C)c1Cc1ccc(O)c(C(C)C)c1] Chiral | cis-13-6 |

-continued
| Structure | | Compound Number |
|---|---|---|
| 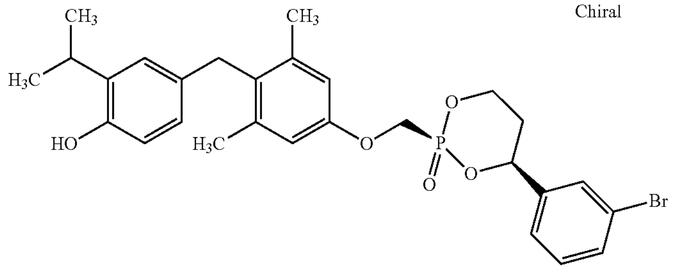 [SMILES: Cc1cc(OC[P@@]2(=O)OCC[C@@H](c3cccc(Br)c3)O2)cc(C)c1Cc1ccc(O)c(C(C)C)c1] | Chiral | cis-13-2 |
| 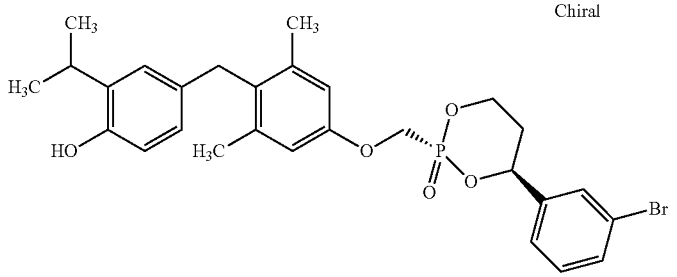 [SMILES: Cc1cc(OC[P@]2(=O)OCC[C@@H](c3cccc(Br)c3)O2)cc(C)c1Cc1ccc(O)c(C(C)C)c1] | Chiral | trans-13-2 |
| 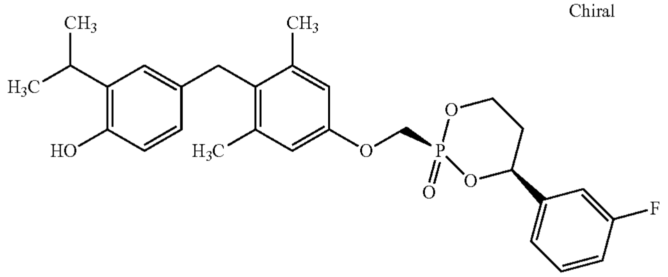 [SMILES: Cc1cc(OC[P@@]2(=O)OCC[C@@H](c3cccc(F)c3)O2)cc(C)c1Cc1ccc(O)c(C(C)C)c1] | Chiral | cis-13-3 |
| 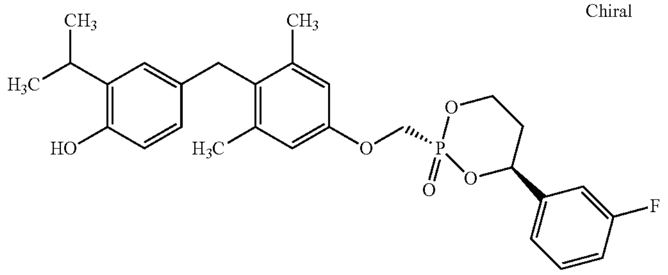 [SMILES: Cc1cc(OC[P@]2(=O)OCC[C@@H](c3cccc(F)c3)O2)cc(C)c1Cc1ccc(O)c(C(C)C)c1] | Chiral | trans-13-3 |
| 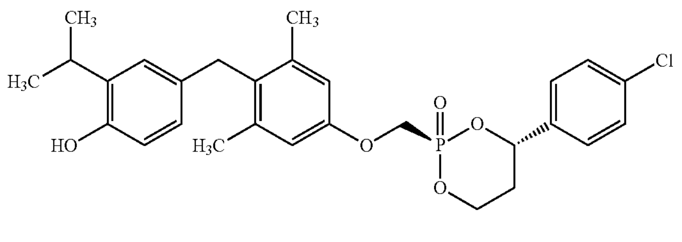 | Chiral | trans-13-6 |

-continued
| Structure | Compound Number |
| --- | --- |
| 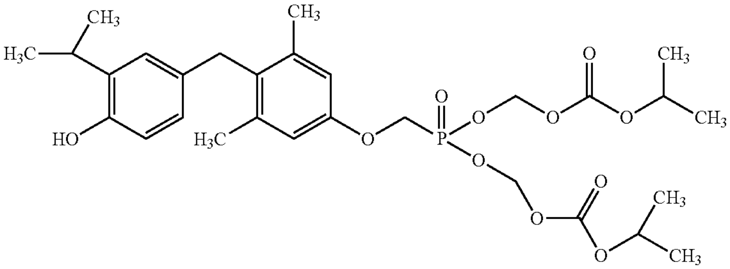 [SMILES: Cc1cc(OCP(=O)(OCOC(=O)OC(C)C)OCOC(=O)OC(C)C)cc(C)c1Cc1ccc(O)c(C(C)C)c1] | 12-3 |
| 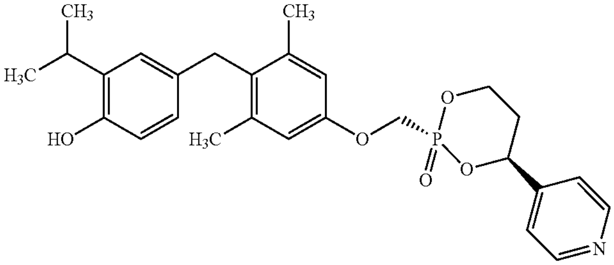 [SMILES: Cc1cc(OC[P@]2(=O)OCC[C@@H](c3ccncc3)O2)cc(C)c1Cc1ccc(O)c(C(C)C)c1] | trans-13-5 |
| 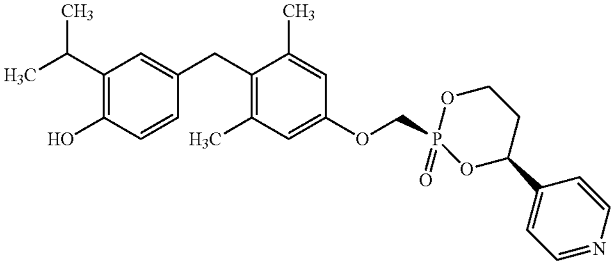 [SMILES: Cc1cc(OC[P@@]2(=O)OCC[C@@H](c3ccncc3)O2)cc(C)c1Cc1ccc(O)c(C(C)C)c1] | cis-13-5 |
| Chiral 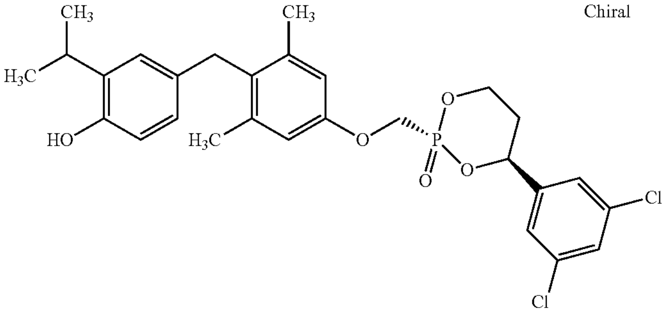 [SMILES: Cc1cc(OC[P@]2(=O)OCC[C@@H](c3cc(Cl)cc(Cl)c3)O2)cc(C)c1Cc1ccc(O)c(C(C)C)c1] | trans-13-7 |
| Chiral 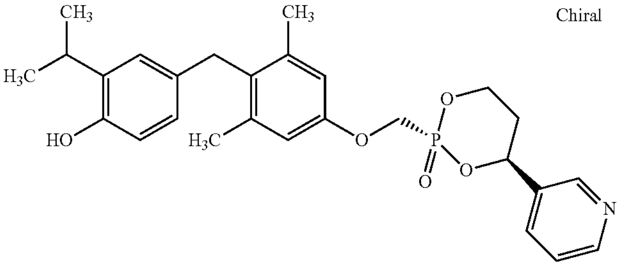 [SMILES: Cc1cc(OC[P@]2(=O)OCC[C@@H](c3cccnc3)O2)cc(C)c1Cc1ccc(O)c(C(C)C)c1] | trans-13-4 |

-continued
| Structure | Compound Number |
| --- | --- |
| 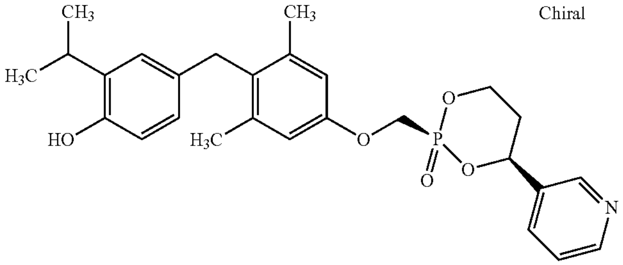 [SMILES: Cc1cc(OC[P@@]2(=O)OCC[C@@H](c3cccnc3)O2)cc(C)c1Cc1ccc(O)c(C(C)C)c1] Chiral | cis-13-4 |
| 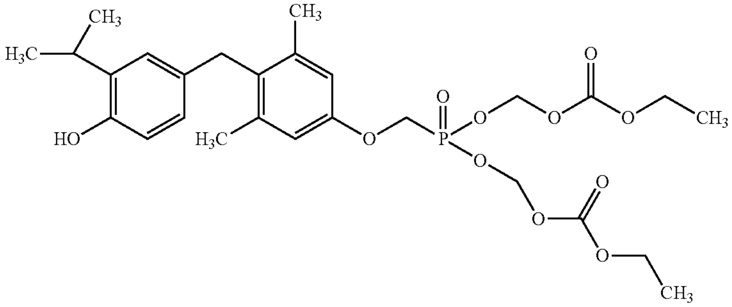 [SMILES: CCOC(=O)OCOP(=O)(COc1cc(C)c(Cc2ccc(O)c(C(C)C)c2)c(C)c1)OCOC(=O)OCC] | 12-2 |
| 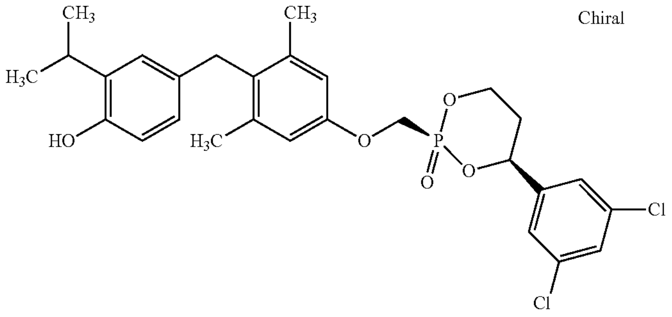 [SMILES: Cc1cc(OC[P@@]2(=O)OCC[C@@H](c3cc(Cl)cc(Cl)c3)O2)cc(C)c1Cc1ccc(O)c(C(C)C)c1] Chiral | cis-13-7 |
| 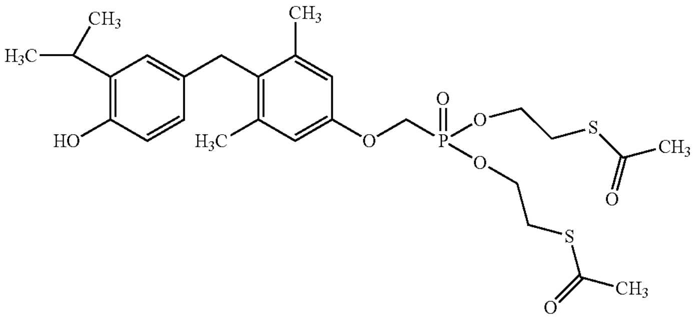 [SMILES: CC(=O)SCCOP(=O)(COc1cc(C)c(Cc2ccc(O)c(C(C)C)c2)c(C)c1)OCCSC(C)=O] | 14 |
| 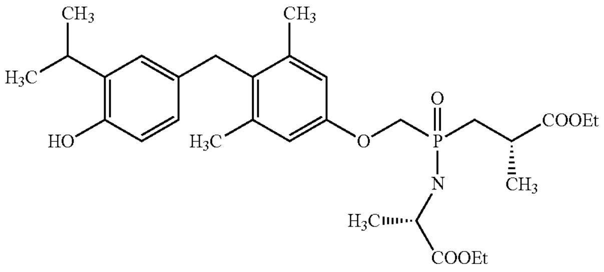 [SMILES: CCOC(=O)[C@H](C)CP(=O)(COc1cc(C)c(Cc2ccc(O)c(C(C)C)c2)c(C)c1)N[C@@H](C)C(=O)OCC] | 15-1 |

-continued
| Structure | Compound Number |
| --- | --- |
| 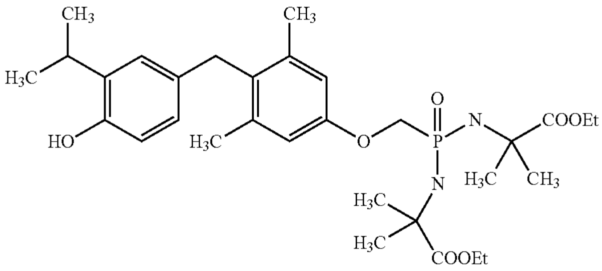 [SMILES: CCOC(=O)C(C)(C)NP(=O)(COc1cc(C)c(Cc2ccc(O)c(C(C)C)c2)c(C)c1)NC(C)(C)C(=O)OCC] | 15-2 |
| 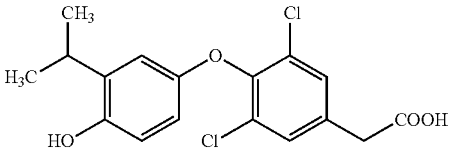 [SMILES: CC(C)c1cc(Oc2c(Cl)cc(CC(=O)O)cc2Cl)ccc1O] | 18 |
| 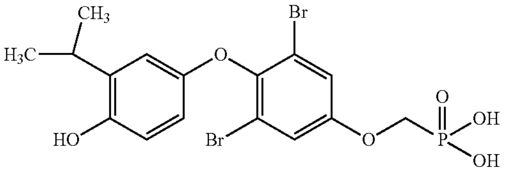 [SMILES: CC(C)c1cc(Oc2c(Br)cc(OCP(=O)(O)O)cc2Br)ccc1O] | 8-1 |
| 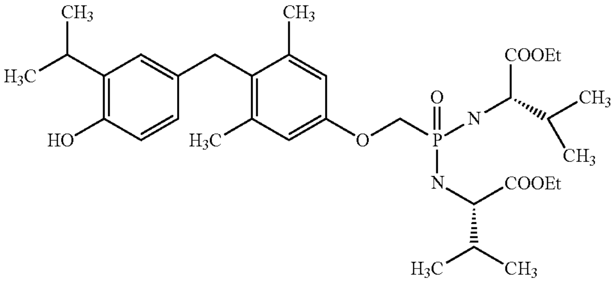 [SMILES: CCOC(=O)[C@@H](NP(=O)(COc1cc(C)c(Cc2ccc(O)c(C(C)C)c2)c(C)c1)N[C@H](C(=O)OCC)C(C)C)C(C)C] | 15-3 |
| 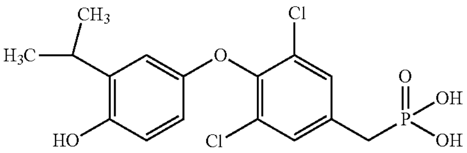 | 19 |
| 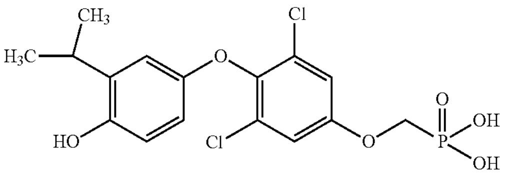 | 8-2 |
| 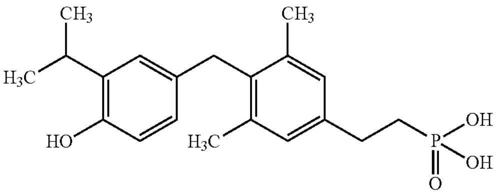 [SMILES: Cc1cc(CCP(=O)(O)O)cc(C)c1Cc1ccc(O)c(C(C)C)c1] | 24-1 |

-continued
| Structure | Compound Number |
|---|---|
| 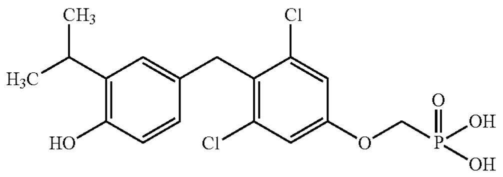 [SMILES: CC(C)c1cc(Cc2c(Cl)cc(OCP(=O)(O)O)cc2Cl)ccc1O] | 7-5 |
| 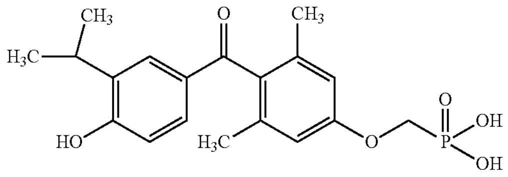 [SMILES: Cc1cc(OCP(=O)(O)O)cc(C)c1C(=O)c1ccc(O)c(C(C)C)c1] | 25 |
| 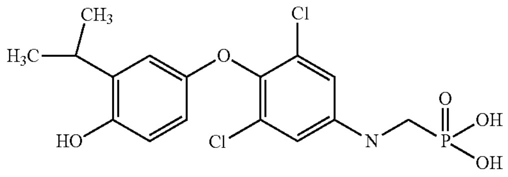 | 22 |
| 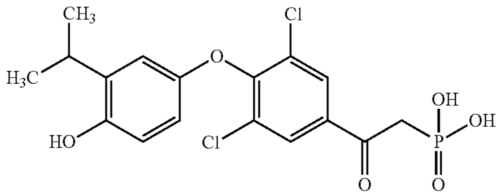 [SMILES: CC(C)c1cc(Oc2c(Cl)cc(C(=O)CP(=O)(O)O)cc2Cl)ccc1O] | 21 |
| 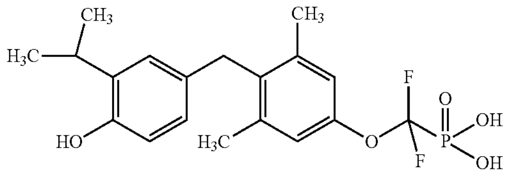 [SMILES: Cc1cc(OC(F)(F)P(=O)(O)O)cc(C)c1Cc1ccc(O)c(C(C)C)c1] | 7-6 |
| 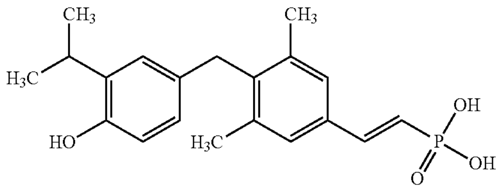 [SMILES: Cc1cc(/C=C/P(=O)(O)O)cc(C)c1Cc1ccc(O)c(C(C)C)c1] | 24-2 |
| 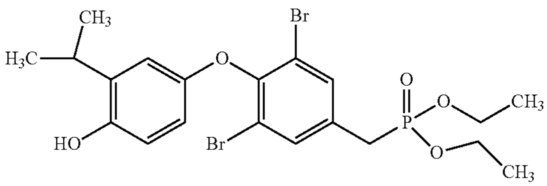 [SMILES: CCOP(=O)(Cc1cc(Br)c(Oc2ccc(O)c(C(C)C)c2)c(Br)c1)OCC] | 19-1 |
| 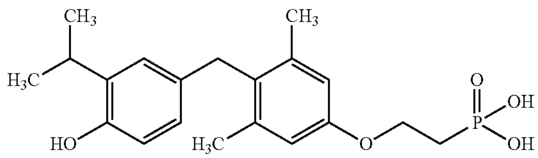 [SMILES: Cc1cc(OCCP(=O)(O)O)cc(C)c1Cc1ccc(O)c(C(C)C)c1] | 26 |

-continued
| Structure | Compound Number |
|---|---|
| 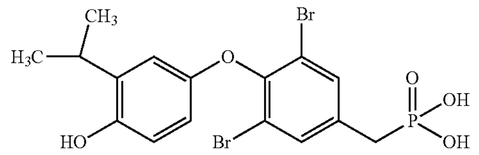 [SMILES: CC(C)c1cc(Oc2c(Br)cc(CP(=O)(O)O)cc2Br)ccc1O] | 19-2 |
| 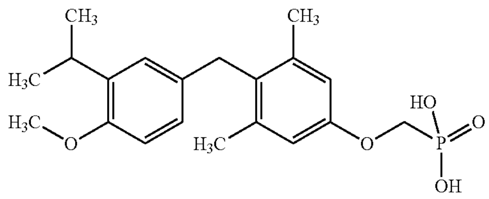 [SMILES: COc1ccc(Cc2c(C)cc(OCP(=O)(O)O)cc2C)cc1C(C)C] | 7-4 |
| 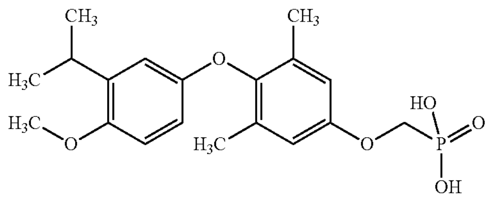 [SMILES: COc1ccc(Oc2c(C)cc(OCP(=O)(O)O)cc2C)cc1C(C)C] | 30 |
| 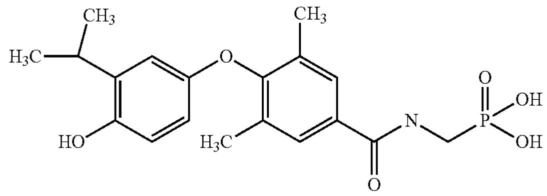 [SMILES: Cc1cc(C(=O)NCP(=O)(O)O)cc(C)c1Oc1ccc(O)c(C(C)C)c1] | 23 |
| 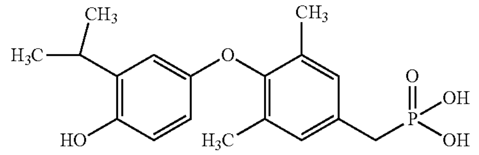 [SMILES: Cc1cc(CP(=O)(O)O)cc(C)c1Oc1ccc(O)c(C(C)C)c1] | 19-3 |
| 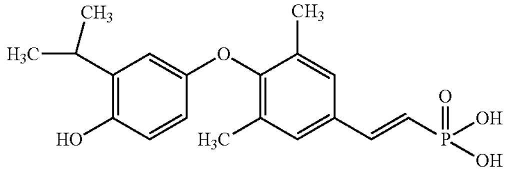 [SMILES: Cc1cc(/C=C/P(=O)(O)O)cc(C)c1Oc1ccc(O)c(C(C)C)c1] | 28 |
| 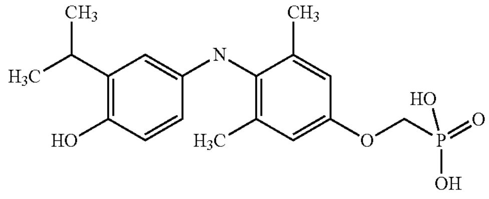 [SMILES: Cc1cc(OCP(=O)(O)O)cc(C)c1Nc1ccc(O)c(C(C)C)c1] | 20 |
| 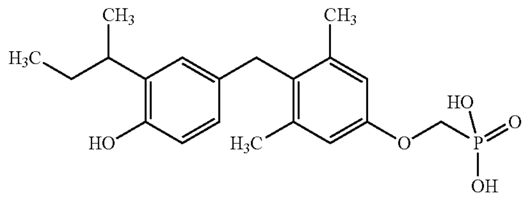 [SMILES: CCC(C)c1cc(Cc2c(C)cc(OCP(=O)(O)O)cc2C)ccc1O] | 7-3 |

-continued
| Structure | Compound Number |
|---|---|
| 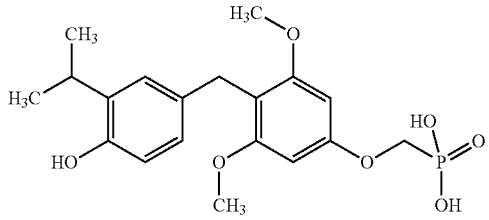 [SMILES: COc1cc(OCP(=O)(O)O)cc(OC)c1Cc1ccc(O)c(C(C)C)c1] | 7-2 |
| 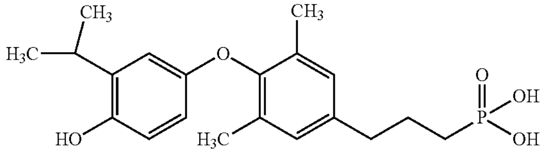 [SMILES: Cc1cc(CCCP(=O)(O)O)cc(C)c1Oc1ccc(O)c(C(C)C)c1] | 29 |
| 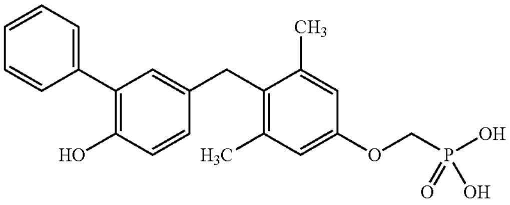 [SMILES: Cc1cc(OCP(=O)(O)O)cc(C)c1Cc1ccc(O)c(-c2ccccc2)c1] | 7-1 |
| 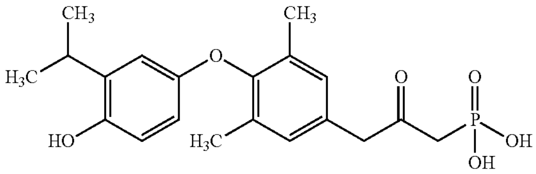 [SMILES: Cc1cc(CC(=O)CP(=O)(O)O)cc(C)c1Oc1ccc(O)c(C(C)C)c1] | 32 |
| 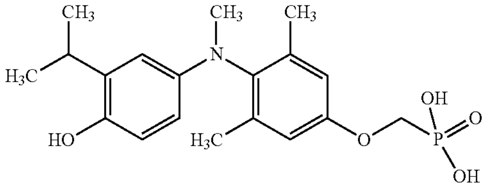 [SMILES: Cc1cc(OCP(=O)(O)O)cc(C)c1N(C)c1ccc(O)c(C(C)C)c1] | 20-1 |
| 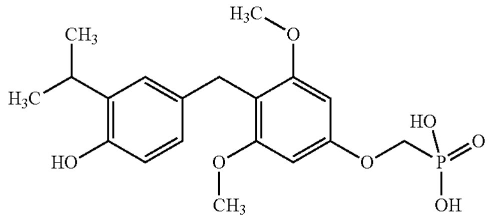 [SMILES: COc1cc(OCP(=O)(O)O)cc(OC)c1Cc1ccc(O)c(C(C)C)c1] | 24 |
| 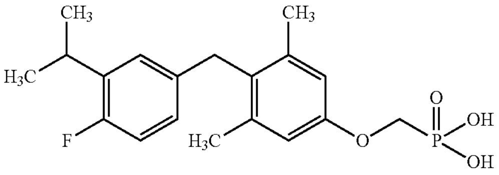 [SMILES: Cc1cc(OCP(=O)(O)O)cc(C)c1Cc1ccc(F)c(C(C)C)c1] | 27 |
| 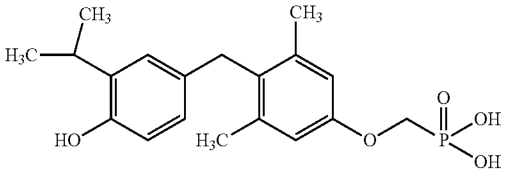 [SMILES: Cc1cc(OCP(=O)(O)O)cc(C)c1Cc1ccc(O)c(C(C)C)c1] | 31 |

-continued
| Structure | Compound Number |
| --- | --- |
| 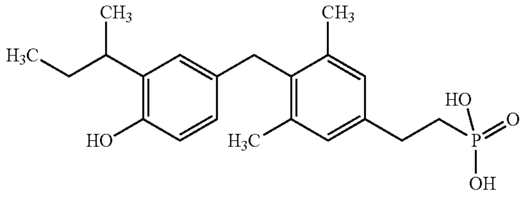 [SMILES: CCC(C)c1cc(Cc2c(C)cc(CCP(=O)(O)O)cc2C)ccc1O] | 24-3 |
| 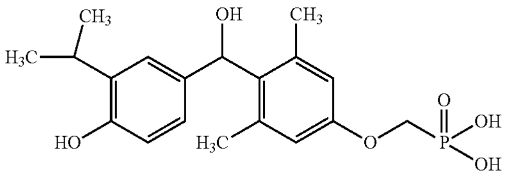 [SMILES: Cc1cc(OCP(=O)(O)O)cc(C)c1C(O)c1ccc(O)c(C(C)C)c1] | 33 |
| 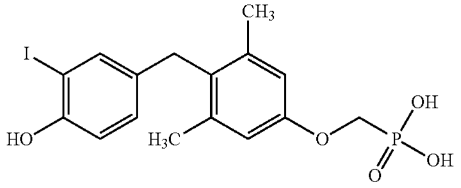 [SMILES: Cc1cc(OCP(=O)(O)O)cc(C)c1Cc1ccc(O)c(I)c1] | 34 |
| 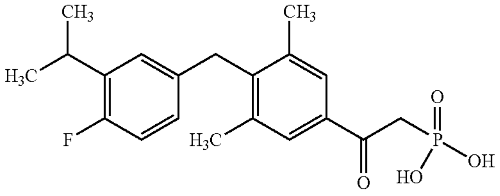 [SMILES: Cc1cc(C(=O)CP(=O)(O)O)cc(C)c1Cc1ccc(F)c(C(C)C)c1] | 41-2 |
| 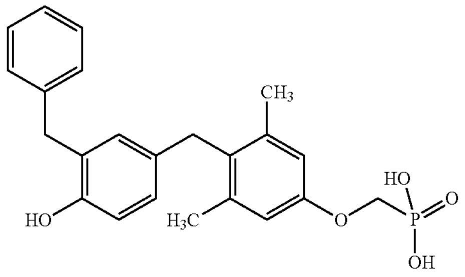 [SMILES: Cc1cc(OCP(=O)(O)O)cc(C)c1Cc1ccc(O)c(Cc2ccccc2)c1] | 38 |
| 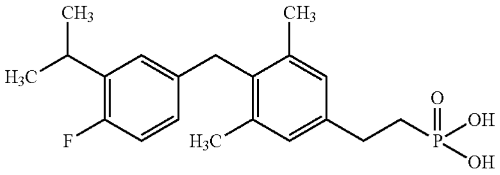 [SMILES: Cc1cc(CCP(=O)(O)O)cc(C)c1Cc1ccc(F)c(C(C)C)c1] | 42-2 |
| 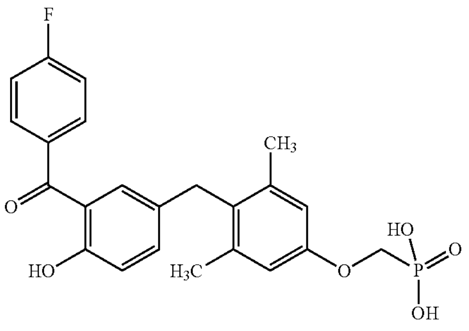 [SMILES: Cc1cc(OCP(=O)(O)O)cc(C)c1Cc1ccc(O)c(C(=O)c2ccc(F)cc2)c1] | 39 |

-continued
| Structure | Compound Number |
|---|---|
| 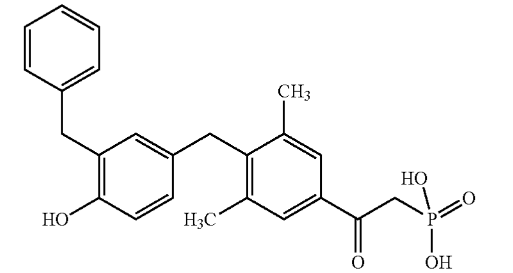 [SMILES: Cc1cc(C(=O)CP(=O)(O)O)cc(C)c1Cc1ccc(O)c(Cc2ccccc2)c1] | 41 |
| 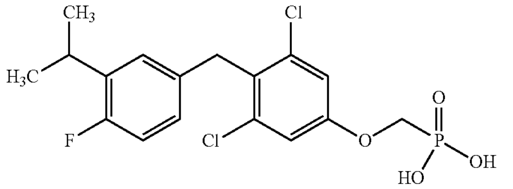 [SMILES: CC(C)c1cc(Cc2c(Cl)cc(OCP(=O)(O)O)cc2Cl)ccc1F] | 27-2 |
| 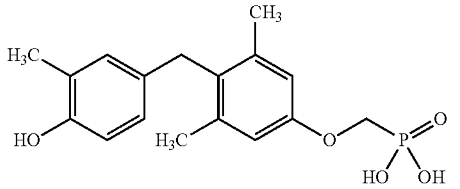 [SMILES: Cc1cc(Cc2c(C)cc(OCP(=O)(O)O)cc2C)ccc1O] | 7-7 |
| 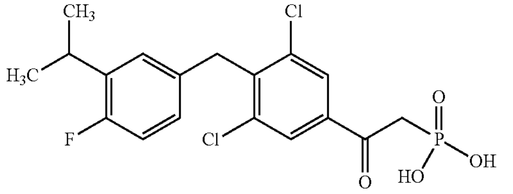 [SMILES: CC(C)c1cc(Cc2c(Cl)cc(C(=O)CP(=O)(O)O)cc2Cl)ccc1F] | 41-3 |
| 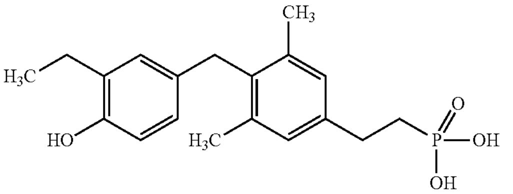 [SMILES: CCc1cc(Cc2c(C)cc(CCP(=O)(O)O)cc2C)ccc1O] | 24-4 |
| 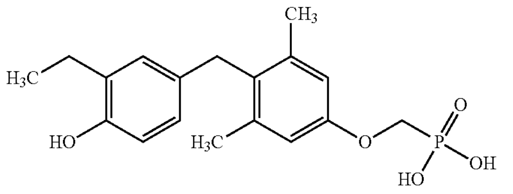 [SMILES: CCc1cc(Cc2c(C)cc(OCP(=O)(O)O)cc2C)ccc1O] | 7-8 |
| 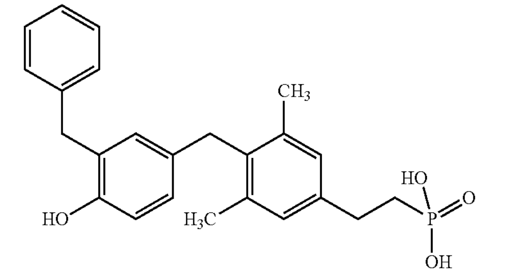 | 42 |

-continued
| Structure | Compound Number |
| --- | --- |
| 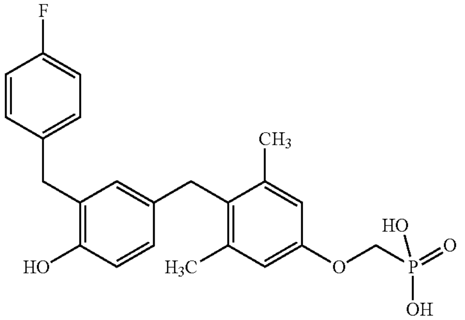 [SMILES: Cc1cc(OCP(=O)(O)O)cc(C)c1Cc1ccc(O)c(Cc2ccc(F)cc2)c1] | 40 |
| 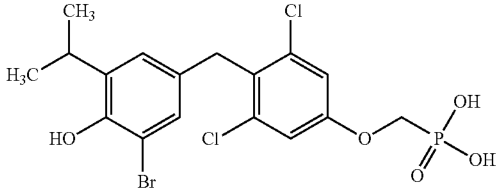 [SMILES: CC(C)c1cc(Cc2c(Cl)cc(OCP(=O)(O)O)cc2Cl)cc(Br)c1O] | 7-14 |
| 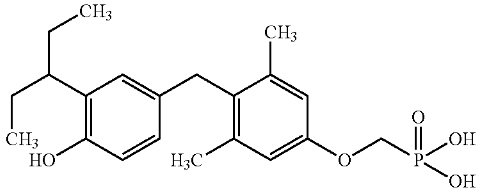 [SMILES: CCC(CC)c1cc(Cc2c(C)cc(OCP(=O)(O)O)cc2C)ccc1O] | 7-9 |
| 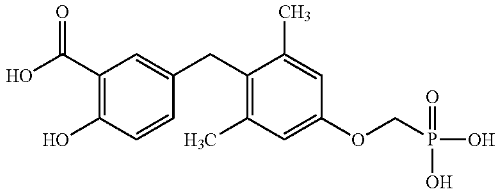 [SMILES: Cc1cc(OCP(=O)(O)O)cc(C)c1Cc1ccc(O)c(C(=O)O)c1] | 35 |
| 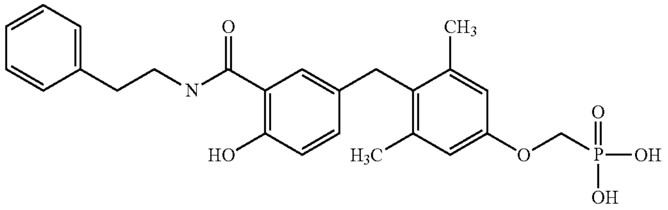 [SMILES: Cc1cc(OCP(=O)(O)O)cc(C)c1Cc1ccc(O)c(C(=O)NCCc2ccccc2)c1] | 37 |
| 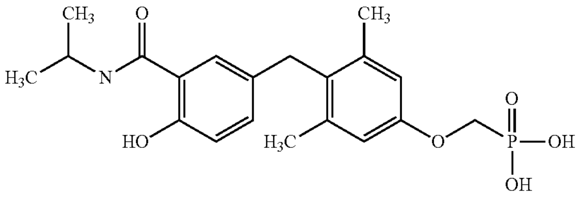 [SMILES: Cc1cc(OCP(=O)(O)O)cc(C)c1Cc1ccc(O)c(C(=O)NC(C)C)c1] | 36 |
| 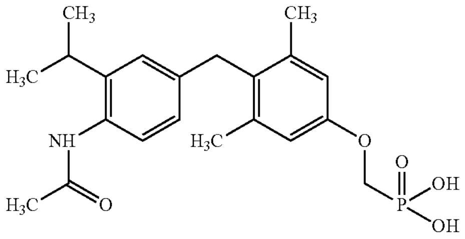 [SMILES: CC(=O)Nc1ccc(Cc2c(C)cc(OCP(=O)(O)O)cc2C)cc1C(C)C] | 7-12 |

-continued
| Structure | Compound Number |
|---|---|
| 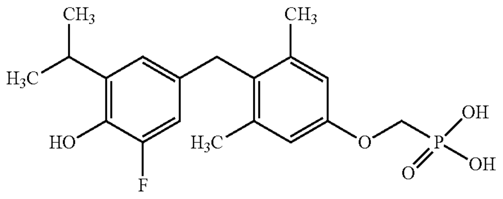 [SMILES: Cc1cc(OCP(=O)(O)O)cc(C)c1Cc1cc(F)c(O)c(C(C)C)c1] | 7-11 |
| 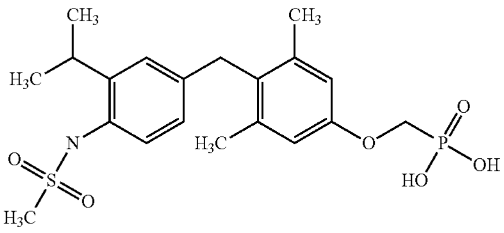 [SMILES: Cc1cc(OCP(=O)(O)O)cc(C)c1Cc1ccc(NS(C)(=O)=O)c(C(C)C)c1] | 7-13 |
| 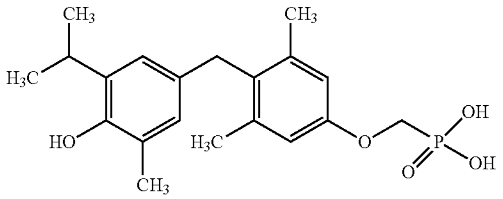 [SMILES: Cc1cc(Cc2c(C)cc(OCP(=O)(O)O)cc2C)cc(C(C)C)c1O] | 7-10 |
| 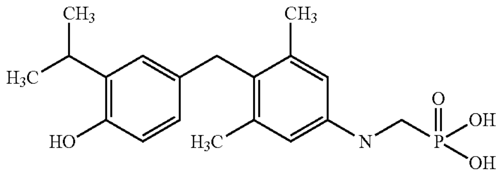 [SMILES: Cc1cc(NCP(=O)(O)O)cc(C)c1Cc1ccc(O)c(C(C)C)c1] | 47 |
| 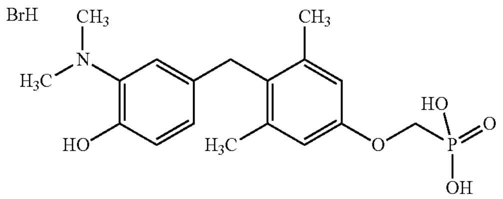 [SMILES: Br ; Cc1cc(OCP(=O)(O)O)cc(C)c1Cc1ccc(O)c(N(C)C)c1] | 49 |
| 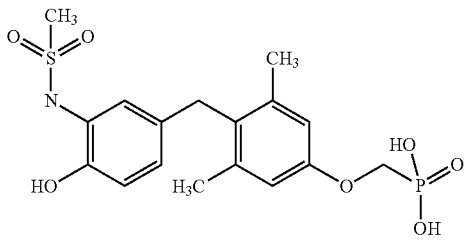 [SMILES: Cc1cc(OCP(=O)(O)O)cc(C)c1Cc1ccc(O)c(NS(C)(=O)=O)c1] | 51-1 |
| 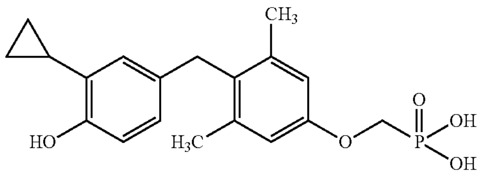 [SMILES: Cc1cc(OCP(=O)(O)O)cc(C)c1Cc1ccc(O)c(C2CC2)c1] | 48 |

-continued
| Structure | Compound Number |
| --- | --- |
| 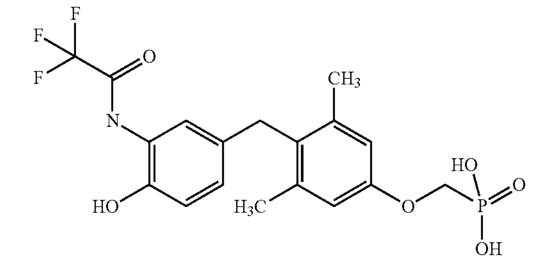 [SMILES: Cc1cc(OCP(=O)(O)O)cc(C)c1Cc1ccc(O)c(NC(=O)C(F)(F)F)c1] | 51-2 |
| 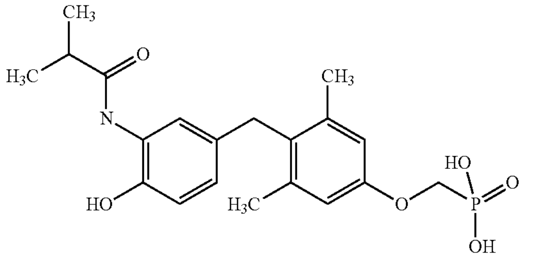 [SMILES: Cc1cc(OCP(=O)(O)O)cc(C)c1Cc1ccc(O)c(NC(=O)C(C)C)c1] | 51-3 |
| 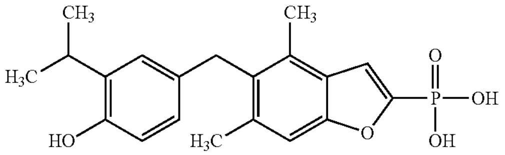 | 45 |
| 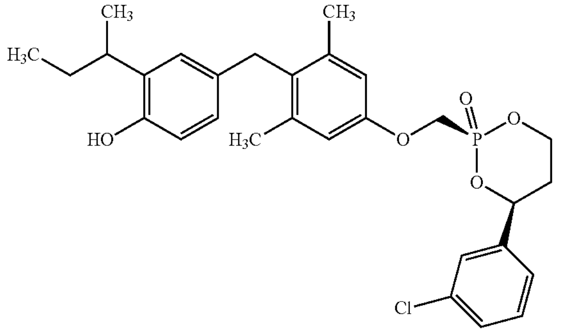 [SMILES: CCC(C)c1cc(Cc2c(C)cc(OC[P@@]3(=O)OCC[C@@H](c4cccc(Cl)c4)O3)cc2C)ccc1O] | 13-8 |
| 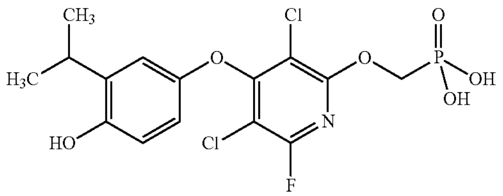 [SMILES: CC(C)c1cc(Oc2c(Cl)c(F)nc(OCP(=O)(O)O)c2Cl)ccc1O] | 57 |

-continued
| Structure | Compound Number |
| --- | --- |
| 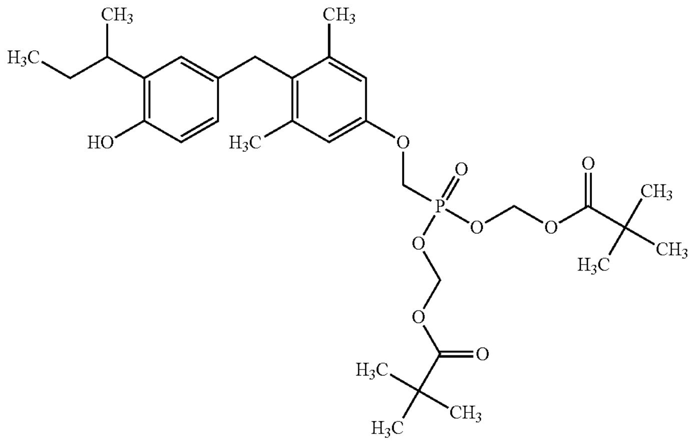 [SMILES: CCC(C)c1cc(Cc2c(C)cc(OCP(=O)(OCOC(=O)C(C)(C)C)OCOC(=O)C(C)(C)C)cc2C)ccc1O] | 12-4 |
| 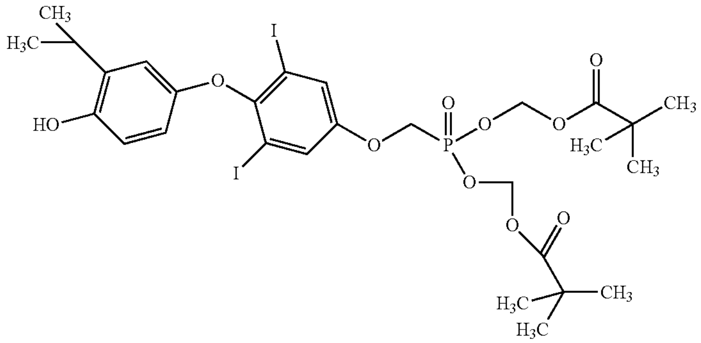 [SMILES: CC(C)c1cc(Oc2c(I)cc(OCP(=O)(OCOC(=O)C(C)(C)C)OCOC(=O)C(C)(C)C)cc2I)ccc1O] | 12-7 |
| 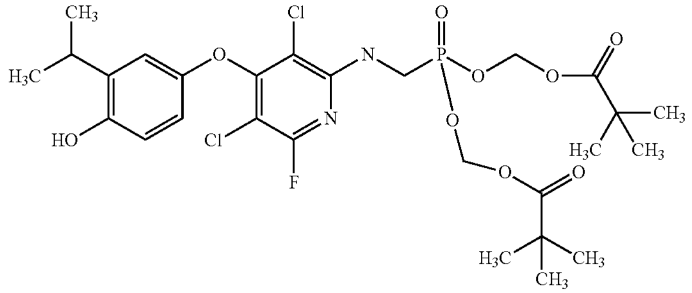 [SMILES: CC(C)c1cc(Oc2c(Cl)c(F)nc(NCP(=O)(OCOC(=O)C(C)(C)C)OCOC(=O)C(C)(C)C)c2Cl)ccc1O] | 12-9 |
| 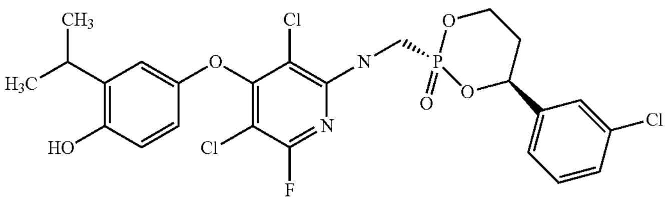 [SMILES: CC(C)c1cc(Oc2c(Cl)c(F)nc(NC[P@]3(=O)OCC[C@@H](c4cccc(Cl)c4)O3)c2Cl)ccc1O] | 13-12-trans |
| 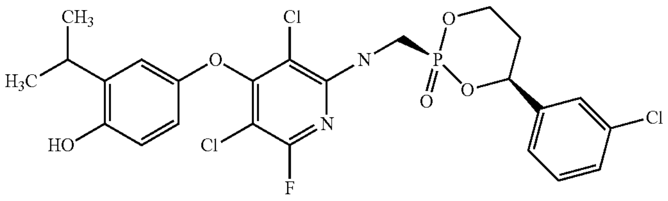 [SMILES: CC(C)c1cc(Oc2c(Cl)c(F)nc(NC[P@@]3(=O)OCC[C@@H](c4cccc(Cl)c4)O3)c2Cl)ccc1O] | 13-12-cis |

-continued
| Structure | Compound Number |
|---|---|
| 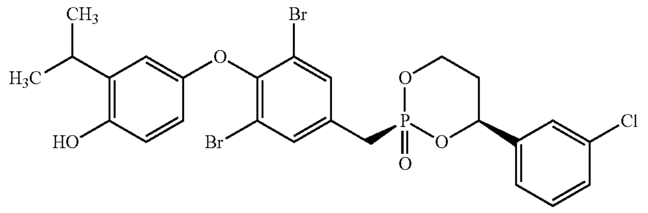 [SMILES: CC(C)c1cc(Oc2c(Br)cc(C[P@@]3(=O)OCC[C@@H](c4cccc(Cl)c4)O3)cc2Br)ccc1O] | 13-9 |
| 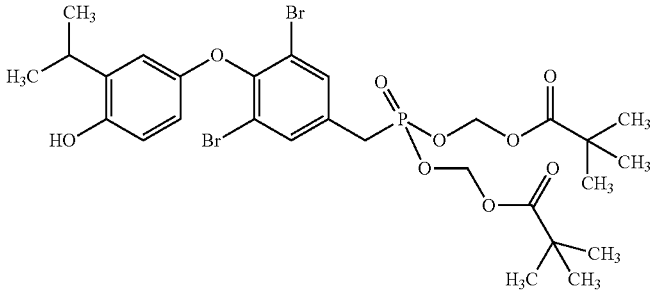 [SMILES: CC(C)c1cc(Oc2c(Br)cc(CP(=O)(OCOC(=O)C(C)(C)C)OCOC(=O)C(C)(C)C)cc2Br)ccc1O] | 12-5 |
| 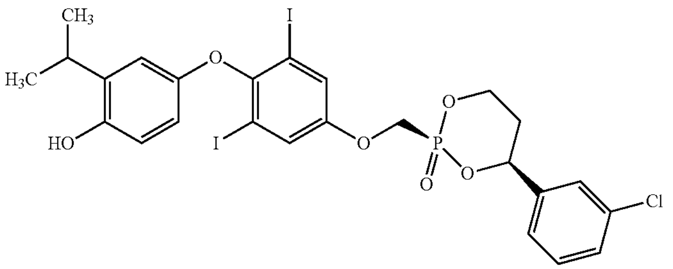 [SMILES: CC(C)c1cc(Oc2c(I)cc(OC[P@@]3(=O)OCC[C@@H](c4cccc(Cl)c4)O3)cc2I)ccc1O] | 13-10 |
| 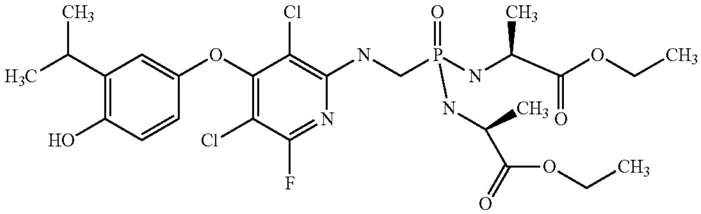 [SMILES: CCOC(=O)[C@H](C)NP(=O)(CNc1nc(F)c(Cl)c(Oc2ccc(O)c(C(C)C)c2)c1Cl)N[C@@H](C)C(=O)OCC] | 15-6 |
| 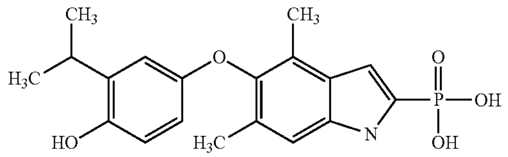 [SMILES: Cc1cc2[nH]c(P(=O)(O)O)cc2c(C)c1Oc1ccc(O)c(C(C)C)c1] | 66 |
| 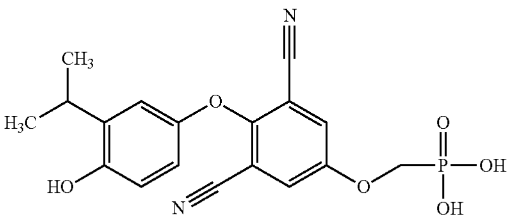 [SMILES: CC(C)c1cc(Oc2c(C#N)cc(OCP(=O)(O)O)cc2C#N)ccc1O] | 56 |
| 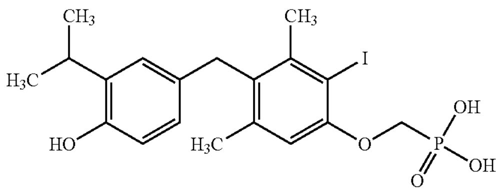 [SMILES: Cc1cc(OCP(=O)(O)O)c(I)c(C)c1Cc1ccc(O)c(C(C)C)c1] | 46 |

-continued
| Structure | Compound Number |
|---|---|
| 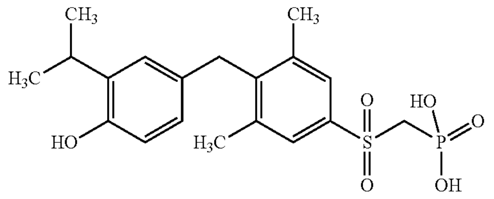 [SMILES: Cc1cc(S(=O)(=O)CP(=O)(O)O)cc(C)c1Cc1ccc(O)c(C(C)C)c1] | 52 |
| 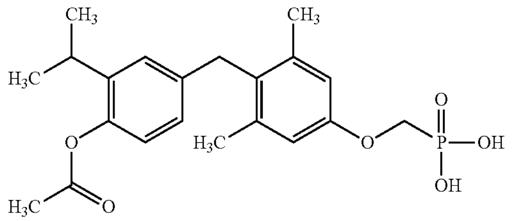 [SMILES: CC(=O)Oc1ccc(Cc2c(C)cc(OCP(=O)(O)O)cc2C)cc1C(C)C] | 58 |
| 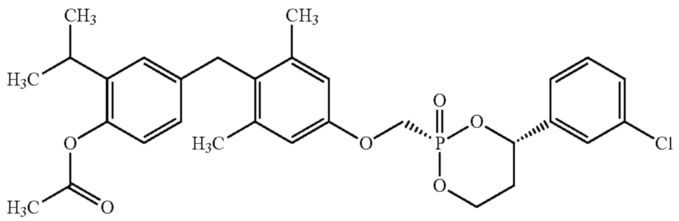 [SMILES: CC(=O)Oc1ccc(Cc2c(C)cc(OC[P@@]3(=O)OCC[C@@H](c4cccc(Cl)c4)O3)cc2C)cc1C(C)C] | 59 |
| 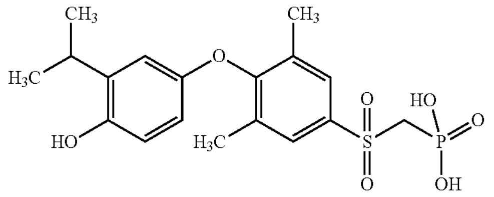 [SMILES: Cc1cc(S(=O)(=O)CP(=O)(O)O)cc(C)c1Oc1ccc(O)c(C(C)C)c1] | 53 |
| 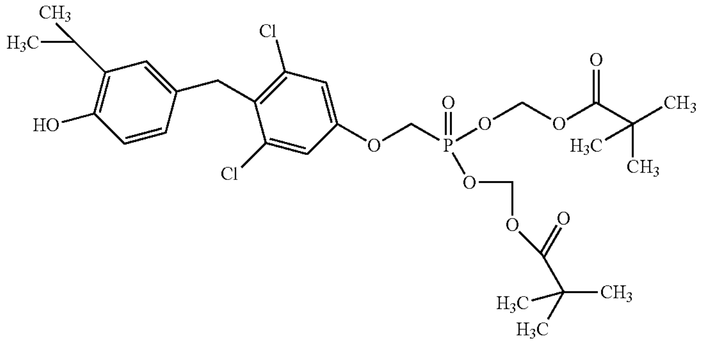 [SMILES: CC(C)c1cc(Cc2c(Cl)cc(OCP(=O)(OCOC(=O)C(C)(C)C)OCOC(=O)C(C)(C)C)cc2Cl)ccc1O] | 12-8 |
| 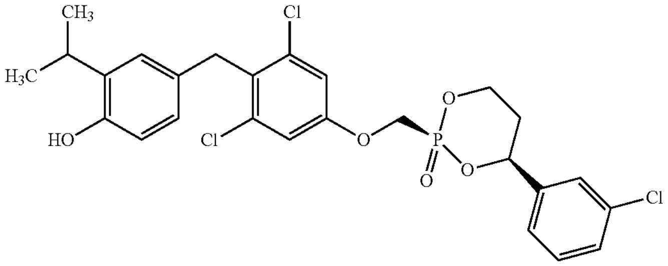 [SMILES: CC(C)c1cc(Cc2c(Cl)cc(OC[P@@]3(=O)OCC[C@@H](c4cccc(Cl)c4)O3)cc2Cl)ccc1O] | 13-11 |

-continued
| Structure | Compound Number |
| --- | --- |
| 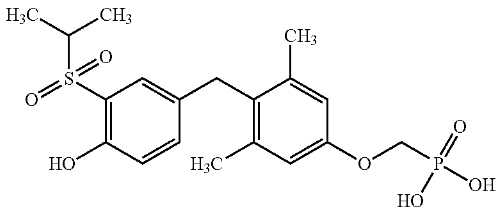 [SMILES: Cc1cc(OCP(=O)(O)O)cc(C)c1Cc1ccc(O)c(S(=O)(=O)C(C)C)c1] | 44 |
| 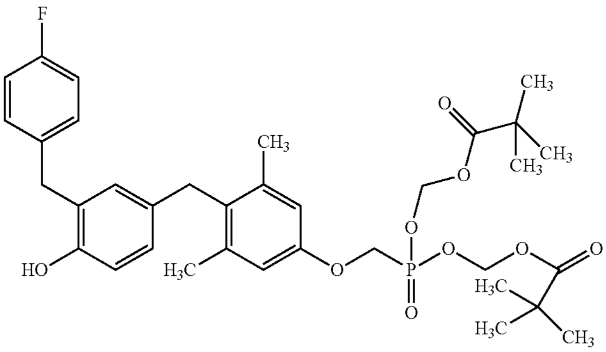 [SMILES: Cc1cc(OCP(=O)(OCOC(=O)C(C)(C)C)OCOC(=O)C(C)(C)C)cc(C)c1Cc1ccc(O)c(Cc2ccc(F)cc2)c1] | 12-6 |
| 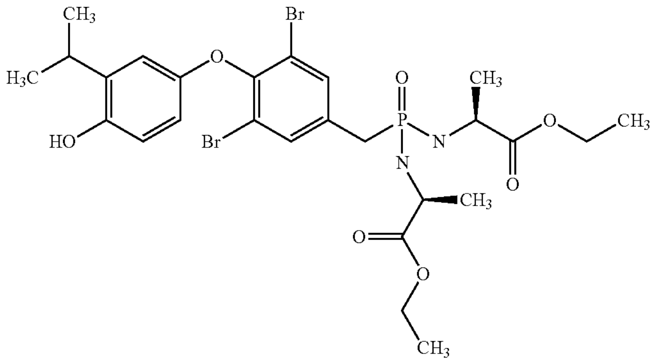 [SMILES: CCOC(=O)[C@H](C)NP(=O)(Cc1cc(Br)c(Oc2ccc(O)c(C(C)C)c2)c(Br)c1)N[C@@H](C)C(=O)OCC] | 15-5 |
| 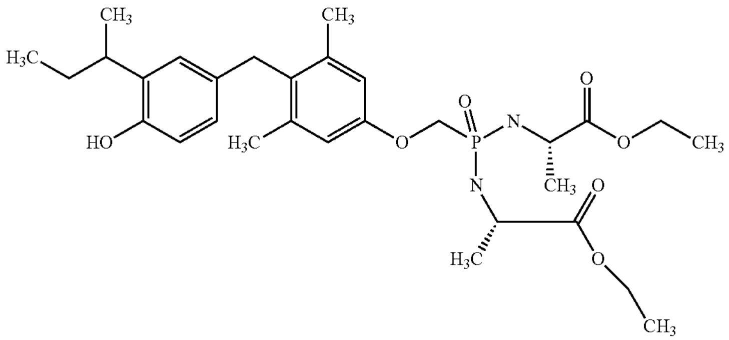 [SMILES: CCOC(=O)[C@H](C)NP(=O)(COc1cc(C)c(Cc2ccc(O)c(C(C)CC)c2)c(C)c1)N[C@@H](C)C(=O)OCC] | 15-4 |

-continued
| Structure | Compound Number |
|---|---|
| 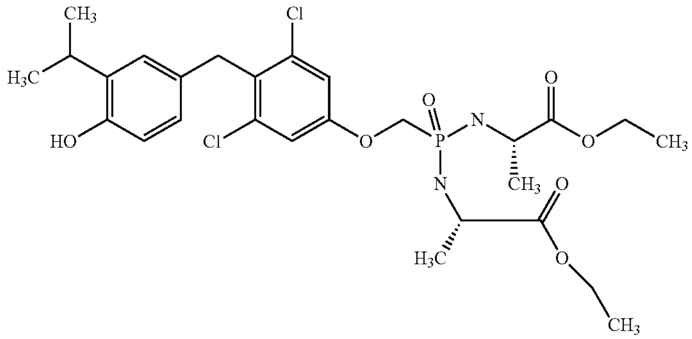 [SMILES: CCOC(=O)[C@H](C)NP(=O)(COc1cc(Cl)c(Cc2ccc(O)c(C(C)C)c2)c(Cl)c1)N[C@@H](C)C(=O)OCC] | 15-7 |
| 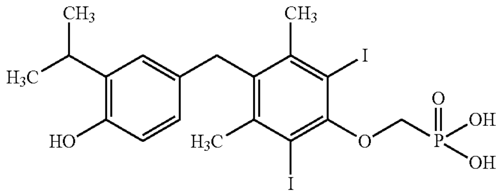 [SMILES: Cc1c(I)c(OCP(=O)(O)O)c(I)c(C)c1Cc1ccc(O)c(C(C)C)c1] | 65-1 |
| 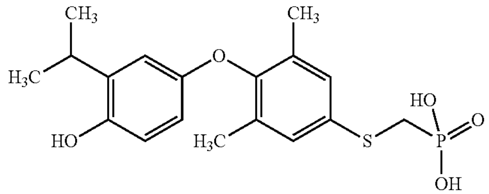 | 54 |
| 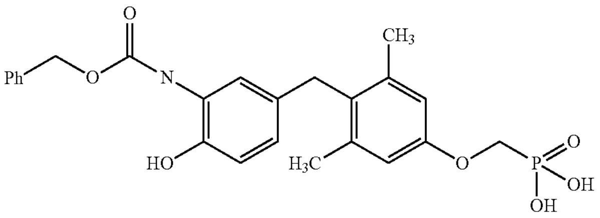 [SMILES: Cc1cc(OCP(=O)(O)O)cc(C)c1Cc1ccc(O)c(NC(=O)OCc2ccccc2)c1] | 50 |
| 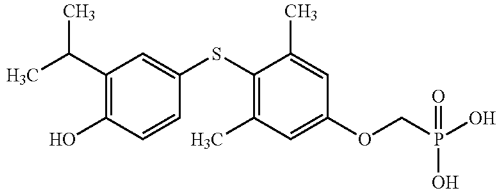 [SMILES: Cc1cc(OCP(=O)(O)O)cc(C)c1Sc1ccc(O)c(C(C)C)c1] | 43 |
| 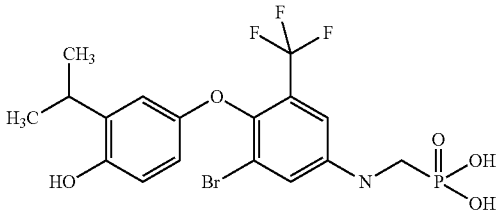 [SMILES: CC(C)c1cc(Oc2c(Br)cc(NCP(=O)(O)O)cc2C(F)(F)F)ccc1O] | 63 |
| 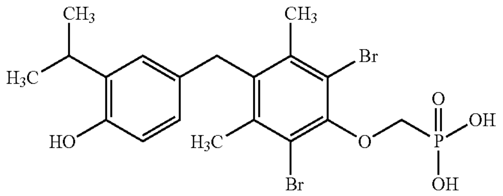 [SMILES: Cc1c(Br)c(OCP(=O)(O)O)c(Br)c(C)c1Cc1ccc(O)c(C(C)C)c1] | 65-2 |

-continued
| Structure | Compound Number |
|---|---|
| 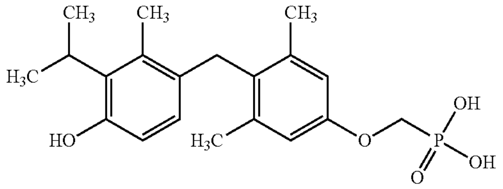 [SMILES: Cc1cc(OCP(=O)(O)O)cc(C)c1Cc1ccc(O)c(C(C)C)c1C] | 7-16 |
| 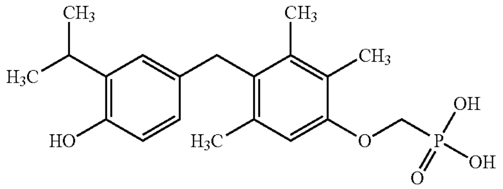 [SMILES: Cc1cc(OCP(=O)(O)O)c(C)c(C)c1Cc1ccc(O)c(C(C)C)c1] | 61 |
| 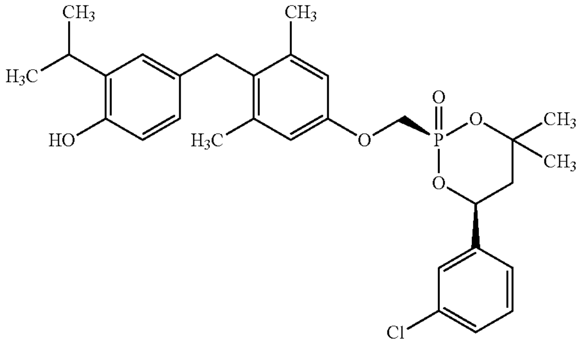 [SMILES: Cc1cc(OC[P@]2(=O)O[C@H](c3cccc(Cl)c3)CC(C)(C)O2)cc(C)c1Cc1ccc(O)c(C(C)C)c1] | 13-13-cis |
| 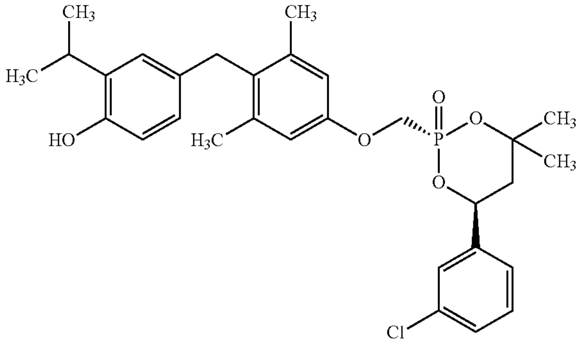 [SMILES: Cc1cc(OC[P@@]2(=O)O[C@H](c3cccc(Cl)c3)CC(C)(C)O2)cc(C)c1Cc1ccc(O)c(C(C)C)c1] | 13-13-trans |
| 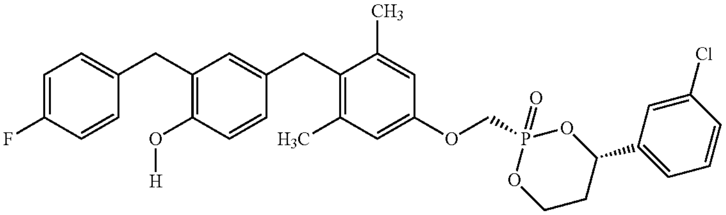 [SMILES: Cc1cc(OC[P@@]2(=O)OCC[C@@H](c3cccc(Cl)c3)O2)cc(C)c1Cc1ccc(O)c(Cc2ccc(F)cc2)c1] | 13-14-cis |
| 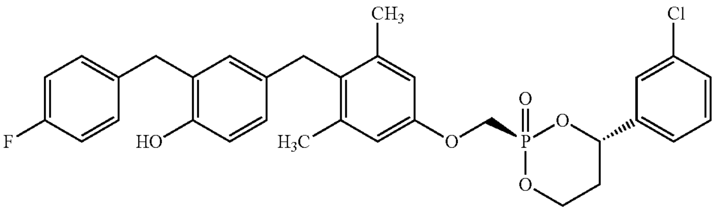 [SMILES: Cc1cc(OC[P@]2(=O)OCC[C@@H](c3cccc(Cl)c3)O2)cc(C)c1Cc1ccc(O)c(Cc2ccc(F)cc2)c1] | 13-14-trans |

-continued

| Structure | Compound Number |
|---|---|
| 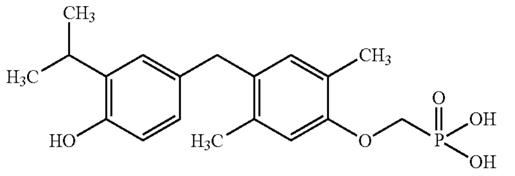 [SMILES: Cc1cc(OCP(=O)(O)O)c(C)cc1Cc1ccc(O)c(C(C)C)c1] | 7-17 |
| 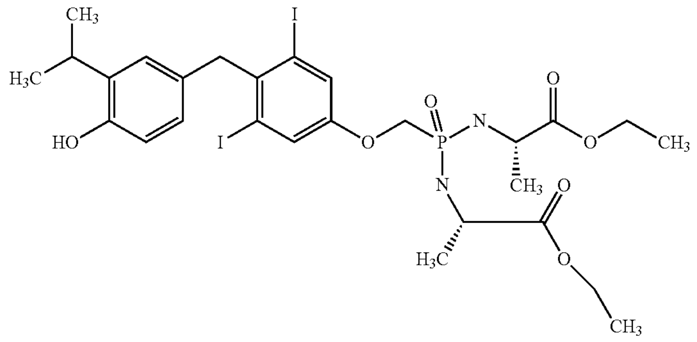 [SMILES: CCOC(=O)[C@H](C)NP(=O)(COc1cc(I)c(Cc2ccc(O)c(C(C)C)c2)c(I)c1)N[C@@H](C)C(=O)OCC] | 15-8 |
| 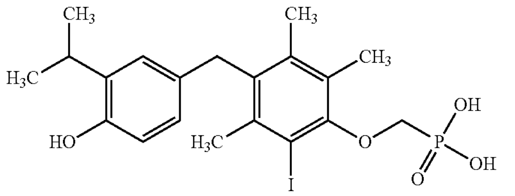 [SMILES: Cc1c(C)c(OCP(=O)(O)O)c(I)c(C)c1Cc1ccc(O)c(C(C)C)c1] | 62 |
| 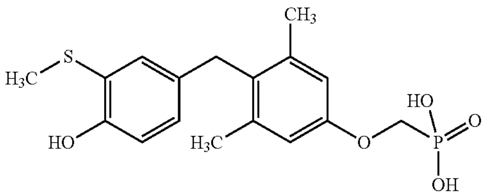 [SMILES: CSc1cc(Cc2c(C)cc(OCP(=O)(O)O)cc2C)ccc1O] | 55 |
| 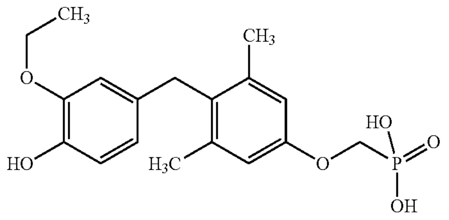 [SMILES: CCOc1cc(Cc2c(C)cc(OCP(=O)(O)O)cc2C)ccc1O] | 7-15 |

or pharmaceutically acceptable salts thereof.

The compounds described above may be prepared according to known methods, including those described in U.S. Pat. No. 7,829,552, which is incorporated herein by reference in its entirety. Additional TRβ agonists are described in U.S. Pat. No. 7,514,419; U.S. Application Publication No. 2009/002895; U.S. Application Publication No. 2010/0081634; U.S. Application Publication No. 2012/0046364; and PCT Application Publication No. WO 2011/038207, all of which are incorporated herein by reference in their entirety.

Pharmaceutical Compositions

The compounds useful as described above can be formulated into pharmaceutical compositions for use in treatment of the conditions described herein. Standard pharmaceutical formulation techniques are used, such as those disclosed in Remington's The Science and Practice of Pharmacy, 21st Ed., Lippincott Williams & Wilkins (2005), incorporated herein by reference in its entirety. Accordingly, some embodiments include pharmaceutical compositions comprising: (a) a safe and therapeutically effective amount of a compound described herein, or pharmaceutically acceptable salts thereof; and (b) a pharmaceutically acceptable carrier, diluent, excipient or combination thereof.

The term "pharmaceutically acceptable carrier" or "pharmaceutically acceptable excipient" includes any and all solvents, diluents, emulsifiers, binders, buffers, dispersion media, coatings, antibacterial and antifungal agents, isotonic and absorption delaying agents and the like, or any other such compound as is known by those of skill in the art to be useful in preparing pharmaceutical formulations. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions. In addition, various adjuvants such as are commonly used in the art may be included. These and other such compounds are described in the literature, e.g., in the Merck Index, Merck & Company, Rahway, NJ. Considerations for the inclusion of various components in pharmaceutical compositions are described, e.g., in Gilman et al. (Eds.) (1990); Goodman and Gilman's: The Pharmacological Basis of Therapeutics, 8th Ed., Pergamon Press.

Some examples of substances, which can serve as pharmaceutically-acceptable carriers or components thereof, are sugars, such as lactose, glucose and sucrose; starches, such as corn starch and potato starch; cellulose and its derivatives, such as sodium carboxymethyl cellulose, ethyl cellulose, and methyl cellulose; powdered tragacanth; malt; gelatin; talc; solid lubricants, such as stearic acid and magnesium stearate; calcium sulfate; vegetable oils, such as peanut oil, cottonseed oil, sesame oil, olive oil, corn oil and oil of theobroma; polyols such as propylene glycol, glycerine, sorbitol, mannitol, and polyethylene glycol; alginic acid; emulsifiers, such as the TWEENS; wetting agents, such as sodium lauryl sulfate; coloring agents; flavoring agents; tableting agents, stabilizers; antioxidants; preservatives; pyrogen-free water; isotonic saline; and phosphate buffer solutions.

The choice of a pharmaceutically-acceptable carrier to be used in conjunction with the subject compound is determined by the way the compound is to be administered.

The compositions described herein are preferably provided in unit dosage form. As used herein, a "unit dosage form" is a composition containing an amount of a compound that is suitable for administration to a subject, in a single dose, according to good medical practice. The preparation of a single or unit dosage form however, does not imply that the dosage form is administered once per day or once per course of therapy. A unit dosage form may comprise a single daily dose or a fractional sub-dose wherein several unit dosage forms are to be administered over the course of a day in order to complete a daily dose. According to the present disclosure, a unit dosage form may be given more or less often that once daily, and may be administered more than once during a course of therapy. Such dosage forms may be administered in any manner consistent with their formulation, including orally, parenterally, and may be administered as an infusion over a period of time (e.g., from about 30 minutes to about 2-6 hours). While single administrations are specifically contemplated, the compositions administered according to the methods described herein may also be administered as a continuous infusion or via an implantable infusion pump.

The methods as described herein may utilize any of a variety of suitable forms for a variety of routes for administration, for example, for oral, nasal, rectal, topical (including transdermal), ocular, intracerebral, intracranial, intrathecal, intra-arterial, intravenous, intramuscular, or other parental routes of administration. The skilled artisan will appreciate that oral and nasal compositions include compositions that are administered by inhalation, and made using available methodologies. Depending upon the particular route of administration desired, a variety of pharmaceutically-acceptable carriers well-known in the art may be used. Pharmaceutically-acceptable carriers include, for example, solid or liquid fillers, diluents, hydrotropes, surface-active agents, and encapsulating substances. Optional pharmaceutically-active materials may be included, which do not substantially interfere with the activity of the compound. The amount of carrier employed in conjunction with the compound is sufficient to provide a practical quantity of material for administration per unit dose of the compound. Techniques and compositions for making dosage forms useful in the methods described herein are described in the following references, all incorporated by reference herein: Modern Pharmaceutics, 4th Ed., Chapters 9 and 10 (Banker & Rhodes, editors, 2002); Lieberman et al., Pharmaceutical Dosage Forms: Tablets (1989); and Ansel, Introduction to Pharmaceutical Dosage Forms 8th Edition (2004).

Various oral dosage forms can be used, including such solid forms as tablets, capsules, granules and bulk powders. Tablets can be compressed, tablet triturates, enteric-coated, sugar-coated, film-coated, or multiple-compressed, containing suitable binders, lubricants, diluents, disintegrating agents, coloring agents, flavoring agents, flow-inducing agents, and melting agents. Liquid oral dosage forms include aqueous solutions, emulsions, suspensions, solutions and/or suspensions reconstituted from non-effervescent granules, and effervescent preparations reconstituted from effervescent granules, containing suitable solvents, preservatives, emulsifying agents, suspending agents, diluents, sweeteners, melting agents, coloring agents and flavoring agents.

The pharmaceutically-acceptable carriers suitable for the preparation of unit dosage forms for peroral administration is well-known in the art. Tablets typically comprise conventional pharmaceutically-compatible adjuvants as inert diluents, such as calcium carbonate, sodium carbonate, mannitol, lactose and cellulose; binders such as starch, gelatin and sucrose; disintegrants such as starch, alginic acid and croscarmelose; lubricants such as magnesium stearate, stearic acid, microcrystalline cellulose, carboxymethyl cellulose, and talc. Tablets may also comprise solubilizers or emulsifiers, such as poloxamers, cremophor/Kolliphor®/Lutrol®, methylcellulose, hydroxypropylmethylcellulose, or others as are known in the art. Glidants such as silicon dioxide can be used to improve flow characteristics of the powder mixture. Coloring agents, such as the FD&C dyes, can be added for appearance. Sweeteners and flavoring agents, such as aspartame, saccharin, menthol, peppermint, and fruit flavors, are useful adjuvants for chewable tablets. Capsules typically comprise one or more solid diluents disclosed above. The selection of carrier components depends on secondary considerations like taste, cost, and shelf stability, which can be readily made by a person skilled in the art.

Peroral (PO) compositions also include liquid solutions, emulsions, suspensions, and the like. The pharmaceutically-acceptable carriers suitable for preparation of such compositions are well known in the art. Typical components of carriers for syrups, elixirs, emulsions and suspensions include ethanol, glycerol, propylene glycol, polyethylene glycol, liquid sucrose, sorbitol and water. For a suspension, typical suspending agents include methyl cellulose, sodium carboxymethyl cellulose, AVICEL RC-591, tragacanth and sodium alginate; typical wetting agents include lecithin and polysorbate 80; and typical preservatives include methyl paraben and sodium benzoate. Peroral liquid compositions may also contain one or more components such as sweeteners, flavoring agents and colorants disclosed above.

Such compositions may also be coated by conventional methods, typically with pH or time-dependent coatings, such that the subject compound is released in the gastrointestinal tract in the vicinity of the desired topical application, or at various times to extend the desired action. Such dosage forms typically include, but are not limited to, one or more of cellulose acetate phthalate, polyvinylacetate phthalate, hydroxypropyl methyl cellulose phthalate, ethyl cellulose, Eudragit coatings, waxes and shellac.

Compositions described herein may optionally include other drug actives.

Other compositions useful for attaining systemic delivery of the subject compounds include sublingual, buccal and nasal dosage forms. Such compositions typically comprise one or more of soluble filler substances such as sucrose, sorbitol and mannitol; and binders such as acacia, microcrystalline cellulose, carboxymethyl cellulose and hydroxypropyl methyl cellulose. Glidants, lubricants, sweeteners, colorants, antioxidants and flavoring agents disclosed above may also be included.

A liquid composition, which is formulated for topical ophthalmic use, is formulated such that it can be administered topically to the eye. The comfort may be maximized as much as possible, although sometimes formulation considerations (e.g. drug stability) may necessitate less than optimal comfort. In the case that comfort cannot be maximized, the liquid may be formulated such that the liquid is tolerable to the patient for topical ophthalmic use. Additionally, an ophthalmically acceptable liquid may either be packaged for single use, or contain a preservative to prevent contamination over multiple uses.

For ophthalmic application, solutions or medicaments are often prepared using a physiological saline solution as a major vehicle. Ophthalmic solutions may preferably be maintained at a comfortable pH with an appropriate buffer system. The formulations may also contain conventional, pharmaceutically acceptable preservatives, stabilizers and surfactants.

Preservatives that may be used in the pharmaceutical compositions disclosed herein include, but are not limited to, benzalkonium chloride, PHMB, chlorobutanol, thimerosal, phenylmercuric, acetate and phenylmercuric nitrate. A useful surfactant is, for example, Tween 80. Likewise, various useful vehicles may be used in the ophthalmic preparations disclosed herein. These vehicles include, but are not limited to, polyvinyl alcohol, povidone, hydroxypropyl methyl cellulose, poloxamers, carboxymethyl cellulose, hydroxyethyl cellulose and purified water.

Tonicity adjustors may be added as needed or convenient. They include, but are not limited to, salts, particularly sodium chloride, potassium chloride, mannitol and glycerin, or any other suitable ophthalmically acceptable tonicity adjustor.

Various buffers and means for adjusting pH may be used so long as the resulting preparation is ophthalmically acceptable. For many compositions, the pH will be between 4 and 9. Accordingly, buffers include acetate buffers, citrate buffers, phosphate buffers and borate buffers. Acids or bases may be used to adjust the pH of these formulations as needed.

Ophthalmically acceptable antioxidants include, but are not limited to, sodium metabisulfite, sodium thiosulfate, acetylcysteine, butylated hydroxyanisole and butylated hydroxytoluene.

Other excipient components, which may be included in the ophthalmic preparations, are chelating agents. A useful chelating agent is edetate disodium, although other chelating agents may also be used in place or in conjunction with it.

For topical use, including for transdermal administration, creams, ointments, gels, solutions or suspensions, etc., containing the compound disclosed herein are employed. Topical formulations may generally be comprised of a pharmaceutical carrier, co-solvent, emulsifier, penetration enhancer, preservative system, and emollient.

For intravenous administration, the compounds and compositions described herein may be dissolved or dispersed in a pharmaceutically acceptable diluent, such as a saline or dextrose solution. Suitable excipients may be included to achieve the desired pH, including but not limited to NaOH, sodium carbonate, sodium acetate, HCl, and citric acid. In various embodiments, the pH of the final composition ranges from 2 to 8, or preferably from 4 to 7. Antioxidant excipients may include sodium bisulfite, acetone sodium bisulfite, sodium formaldehyde, sulfoxylate, thiourea, and EDTA. Other non-limiting examples of suitable excipients found in the final intravenous composition may include sodium or potassium phosphates, citric acid, tartaric acid, gelatin, and carbohydrates such as dextrose, mannitol, and dextran. Further acceptable excipients are described in Powell, et al., Compendium of Excipients for Parenteral Formulations, PDA J Pharm Sci and Tech 1998, 52 238-311 and Nema et al., Excipients and Their Role in Approved Injectable Products: Current Usage and Future Directions, PDA J Pharm. Sci. Tech. 2011, 65 287-332, both of which are incorporated herein by reference in their entirety. Antimicrobial agents may also be included to achieve a bacteriostatic or fungistatic solution, including but not limited to phenylmercuric nitrate, thimerosal, benzethonium chloride, benzalkonium chloride, phenol, cresol, and chlorobutanol.

The compositions for intravenous administration may be provided to caregivers in the form of one more solids that are reconstituted with a suitable diluent such as sterile water, saline or dextrose in water shortly prior to administration. In other embodiments, the compositions are provided in solution ready to administer parenterally. In still other embodiments, the compositions are provided in a solution that is further diluted prior to administration. In embodiments that include administering a combination of a compound described herein and another agent, the combination may be provided to caregivers as a mixture, or the caregivers may mix the two agents prior to administration, or the two agents may be administered separately.

The actual unit dose of the active compounds described herein depends on the specific compound, and on the condition to be treated. In some embodiments, the dose may be from about 0.01 mg/kg to about 120 mg/kg or more of body weight, from about 0.05 mg/kg or less to about 70 mg/kg, from about 0.1 mg/kg to about 50 mg/kg of body weight, from about 1.0 mg/kg to about 10 mg/kg of body weight, from about 5.0 mg/kg to about 10 mg/kg of body weight, or from about 10.0 mg/kg to about 20.0 mg/kg of body weight. In some embodiments, the dose may be less than 100 mg/kg, 90 mg/kg, 80 mg/kg, 70 mg/kg, 60 mg/kg, 50 mg/kg, 40 mg/kg, 30 mg/kg, 25 mg/kg, 20 mg/kg, 10 mg/kg, 7.5 mg/kg, 6 mg/kg, 5 mg/kg, 4 mg/kg, 3 mg/kg, 2.5 mg/kg, 1 mg/kg, 0.5mg/kg, 0.1 mg/kg, 0.05 mg/kg or 0.005 mg/kg of body weight. In some embodiments, the actual unit dose is 0.05, 0.07, 0.1, 0.3, 1.0, 3.0, 5.0, 10.0 or 25.0 mg/kg of body weight. Thus, for administration to a 70 kg person, the dosage range would be from about 0.1 mg to 70 mg, from about 1 mg to about 50 mg, from about 0.5 mg to about 10 mg, from about 1 mg to about 10 mg, from about 2.5 mg to about 30 mg, from about 35 mg or less to about 700 mg or more, from about 7 mg to about 600 mg, from about 10 mg to about 500 mg, or from about 20 mg to about 300 mg, or from about 200 mg to about 2000 mg. In some embodiments, the actual unit dose is 5 mg. In some embodiments the actual unit dose is 10 mg. In some embodiments, the actual unit dose is 25 mg. In some embodiments, the actual unit dose is 250 mg or less. In some embodiments, the actual unit dose is 100 mg or less. In some embodiments, the actual unit dose is 70 mg or less Said compounds may also be incorporated into formulations for delivery outside the systemic circulation. Such formulations may include enteric-coated capsules, tablets, soft-gels, spray dried powders, polymer matrices, hydrogels, enteric-coated solids, crystalline solids, amorphous solids, glassy solids, coated micronized particles, liquids, nebulized liquids, aerosols, or microcapsules.

Methods of Administration

The compositions described above may be administered through any suitable route of administration, for example, by injection, such as subcutaneously, intramuscularly, intraperitoneally, intravenously, or intraarterially; topically, such as by cream, lotion, or patch; orally, such as by a pill, dissolved liquid, oral suspension, buccal film, or mouthrinse; nasally, such as by a nasal aerosol, powder, or spray; or ocularly, such as by an eye drop). In some embodiments, the composition may be administered one, twice, three times, our four times per day. In other embodiments, the composition may be administered once, twice, or three times per week. In other embodiments, the composition is administered every other day, every three days, or every four days. In other embodiments, the composition every other week, every three weeks, or every four weeks. In other embodiments, the composition is administered once per month or twice per month.

In some embodiments, an initial loading dose is administered which is higher than subsequent doses (maintenance doses). The dosage form or mode of administration of a maintenance dose may be different from that used for the loading dose. In any of the embodiments disclosed herein, a maintenance dose may comprise administration of the unit dosage form on any dosing schedule contemplated herein, including but not limited to, monthly or multiple times per month, biweekly or multiple times each two weeks, weekly or multiple times per week, daily or multiple times per day. It is contemplated within the present disclosure that dosing holidays may be incorporated into the dosing period of the maintenance dose. Such dosing holidays may occur immediately after the administration of the loading dose or at any time during the period of administration of the maintenance dose. In some embodiments, the loading dose is 300 mg or less; 250 mg or less, 200 mg or less, 150 mg or less, or 100 mg or less. In some embodiments, the maintenance dose is 300 mg or less; 200 mg or less, 100 mg or less, 50 mg or less, 25 mg or less, 10 mg or less, 5 mg or less, or 1 mg or less.

Methods of Treatment

Some embodiments according to the methods and compositions of the present disclosure relate to a method for the reduction or prevention of the deposition of extracellular matrix proteins, comprising administering an effective amount of a compound described herein to a subject in need thereof. In some embodiments, said deposition of extracellular matrix proteins may comprise abnormal or excessive deposition of said proteins. In some embodiments, said extracellular matrix proteins may comprise one or more of collagen, keratin, elastin, or fibrin. In some embodiments, said extracellular matrix proteins may comprise collagen. In some embodiments, said extracellular matrix proteins may comprise Type I collagen. In some embodiments, said extracellular matrix proteins may comprise Collagen Type Ia. In some embodiments, said extracellular matrix proteins may comprise Type III collagen. Some embodiments according to the compositions and methods of the present disclosure relate to a method for the treatment of a fibrosis or its symptoms or sequelae, comprising administering an effective amount of a compound described herein to a subject in need thereof.

In some embodiments, the compounds and compositions comprising the compounds described herein can be used to treat a variety of conditions arising from fibrosis or inflammation, and specifically including those associated with abnormal collagen deposition. Example conditions include glycogen storage disease type III (GSD III), glycogen storage disease type VI (GSD VI), glycogen storage disease type IX (GSD IX), non-alcoholic steatohepatitis (NASH), cirrhosis, hepatitis, scleroderma, alcoholic fatty liver disease, atherosclerosis, asthma, cardiac fibrosis, organ transplant fibrosis, muscle fibrosis, pancreatic fibrosis, bone-marrow fibrosis, liver fibrosis, cirrhosis of liver and gallbladder, fibrosis of the spleen, pulmonary fibrosis, idiopathic pulmonary fibrosis, diffuse parenchymal lung disease, idiopathic interstitial fibrosis, diffuse interstitial fibrosis, interstitial pneumonitis, desquamative interstitial pneumonia, respiratory bronchiolitis, interstitial lung disease, chronic interstitial lung disease, acute interstitial pneumonitis, hypersensitivity pneumonitis, nonspecific interstitial pneumonia, cryptogenic organizing pneumonia, lymphocytic interstitial pneumonia, pneumoconiosis, silicosis, emphysema, interstitial fibrosis, sarcoidosis, mediastinal fibrosis, cardiac fibrosis, atrial fibrosis, endomyocardial fibrosis, renal fibrosis, chronic kidney disease, Type II diabetes, macular degeneration, keloid lesions, hypertrophic scar, nephrogenic systemic fibrosis, injection fibrosis, complications of surgery, fibrotic chronic allograft vasculopathy and/or chronic rejection in transplanted organs, fibrosis associated with ischemic reperfusion injury, post-vasectomy pain syndrome, fibrosis associated with rheumatoid arthritis, arthrofibrosis, Dupuytren's disease, dermatomyositis-polymyositis, mixed connective tissue disease, fibrous proliferative lesions of the oral cavity, fibrosing intestinal strictures, Crohn's disease, glial scarring, leptomeningeal fibrosis, meningitis, systemic lupus erythematosus, fibrosis due to radiation exposure, fibrosis due to mammary cystic rupture, myelofibrosis, retroperitoneal fibrosis, progressive massive fibrosis, or symptoms or sequelae thereof, or other diseases of conditions resulting in the excessive deposition of extracellular matrix components, such as collagen.

In some embodiments the methods of the present disclosure comprise methods for the treatment, amelioration, or prevention of a fibrotic condition. In some embodiments, said fibrotic condition may be secondary to another condition. In some embodiments, said fibrotic condition or primary condition may further comprise chronic inflammation of an organ, tissue, spatial region, or fluid-connected area of the body of a subject. In some embodiments, said inflammation may comprise activation of one or more TGF-beta dependent signaling pathways. In some embodiments, said TGF-β dependent signaling pathways may comprise one or more elements responsive to T3 or T4. In some embodiments, said fibrotic condition may comprise abnormal or excessive deposition of one or more of collagen, keratin, or elastin. In some embodiments, said fibrotic condition may comprise abnormal or excessive deposition of collagen. In some embodiments, said fibrotic condition may comprise abnormal or excessive deposition of Type I collagen. In some embodiments, said fibrotic condition may comprise abnormal or excessive deposition of Collagen Type Ia. In some embodiments, said fibrotic condition may comprise abnormal or excessive deposition of Type III collagen. In some embodiments said fibrotic condition may comprise one or more of glycogen storage disease type III (GSD III), glycogen storage disease type VI (GSD VI), glycogen storage disease type IX (GSD IX), non-alcoholic steatohepatitis (NASH), cirrhosis, hepatitis, scleroderma, alcoholic fatty liver disease, atherosclerosis, asthma, cardiac fibrosis, organ transplant fibrosis, muscle fibrosis, pancreatic fibrosis, bone-marrow fibrosis, liver fibrosis, cirrhosis of liver and gallbladder, fibrosis of the spleen, scleroderma, pulmonary fibrosis, idiopathic pulmonary fibrosis, diffuse parenchymal lung disease, idiopathic interstitial fibrosis, diffuse interstitial fibrosis, interstitial pneumonitis, desquamative interstitial pneumonia, respiratory bronchiolitis, interstitial lung disease, chronic interstitial lung disease, acute interstitial pneumonitis, hypersensitivity pneumonitis, nonspecific interstitial pneumonia, cryptogenic organizing pneumonia, lymphocytic interstitial pneumonia, pneumoconiosis, silicosis, emphysema, interstitial fibrosis, sarcoidosis, mediastinal fibrosis, cardiac fibrosis, atrial fibrosis, endomyocardial fibrosis, renal fibrosis, chronic kidney disease, Type II diabetes, macular degeneration, keloid lesions, hypertrophic scar, nephrogenic systemic fibrosis, injection fibrosis, complications of surgery, fibrotic chronic allograft vasculopathy and/or chronic rejection in transplanted organs, fibrosis associated with ischemic reperfusion injury, post-vasectomy pain syndrome, fibrosis associated with rheumatoid arthritis, arthrofibrosis, Dupuytren's disease, dermatomyositis-polymyositis, mixed connective tissue disease, fibrous proliferative lesions of the oral cavity, fibrosing intestinal strictures, Crohn's disease, glial scarring, leptomeningeal fibrosis, meningitis, systemic lupus erythematosus, fibrosis due to radiation exposure, fibrosis due to mammary cystic rupture, myelofibrosis, retroperitoneal fibrosis, progressive massive fibrosis. In some embodiments, said fibrotic condition may comprise one or more of GSD III, GSD IX, Non Alcoholic Steatohepatitis, cirrhosis of the liver and/or pancreas, scleroderma, idiopathic pulmonary fibrosis, psoriasis, alcoholic fatty liver disease, Dupuytren's disease, and/or any combination thereof.

According to the methods and compositions of the present disclosure, thyroid receptor agonists such as those disclosed herein, and especially including Compounds 1-4, may be administered to a subject for the treatment, amelioration, prevention, or cure of a fibrotic condition, or a condition for which fibrosis is a symptom or sequela. According to the methods and composition as disclosed herein, said fibrotic condition or condition having fibrosis as a sequela may further comprise chronic inflammation. According to the methods and compositions as disclosed herein, said fibrotic condition or condition having fibrosis as a sequela may further comprise activation of one or more TGF-β dependent signaling pathways. According to the methods and compositions as disclosed herein, said fibrotic condition or condition having fibrosis as a sequela may further comprise activation and/or repression of one or more Thyroid Receptor Beta (TRβ) dependent signaling pathways. According to the methods and compositions as disclosed herein, said fibrotic condition or condition having fibrosis as a sequela may further comprise the involvement of signaling pathways responsive to triiodothyronine (T3), thyroxine (T4), any combination thereof, or mimetics thereof. According to the methods and compositions as disclosed herein, said fibrotic condition or condition having fibrosis as a sequela may further comprise the involvement of receptors responsive to T3, T4, any combination thereof, or mimetics thereof. In some embodiments according to the methods and compositions disclosed herein, said fibrotic condition or condition having fibrosis as a sequela may comprise the involvement of TRβ. In some embodiments according to the methods and compositions disclosed herein, said fibrotic condition or condition having fibrosis as a sequela may comprise one or more conditions which are prevented, ameliorated, or cured by the administration of one or more agonists of TRβ. In some embodiments according to the methods and compositions disclosed herein, said fibrotic condition or condition having fibrosis as a sequela may comprise one or more conditions which are prevented, ameliorated, or cured by the administration of one or more of Compounds 1-4. In some embodiments, said one or more agonists of TRβ, or said one or more of Compounds 1-4, may be coadministered with one or more active drug compounds and/or one or more excipients. In some embodiments, said one or more agonists of TRβ, or said one or more of Compounds 1-4, may be administered prior to, during, or after a surgical intervention, phototherapy, or ultrasound therapy. In some embodiments, said one or more agonists of TRß, or said one or more of Compounds 1-4, may be coadministered with one or more of Pirfenidone, nintedanib, and/or a fibroblast growth factor receptor antagonist, and/or a collagenase, such as *Clostridium histolyticum* collagenase.

In some embodiments, the compositions and methods described herein provide compositions and methods for the treatment, amelioration, prevention or cure of collagen deposition. In some embodiments, said collagen deposition comprises and abnormal or excessive deposition of collagen. In some embodiments, said collagen deposition may comprise abnormal or excessive deposition of Type I collagen. In some embodiments, said collagen deposition may comprise abnormal or excessive deposition of Collagen Type Ia. In some embodiments, said collagen deposition may comprise abnormal or excessive deposition of Type III collagen. According to the methods and compositions as disclosed herein, said collagen deposition may further comprise the involvement of receptors responsive to T3, T4, any combination thereof, or mimetics thereof. In some embodiments according to the methods and compositions disclosed herein, said collagen deposition may comprise the involvement of TRβ. In some embodiments according to the methods and compositions disclosed herein, said collagen deposition may be prevented, ameliorated, or cured by the administration of one or more agonists of TRβ. In some embodiments according to the methods and compositions disclosed herein, said collagen deposition may be prevented, ameliorated, or cured by the administration of one or more of Compounds 1-4. In some embodiments, said one or more agonists of TRβ, or said one or more of Compounds 1-4, may be coadministered with one or more active drug compounds and/or one or more excipients. In some embodiments, said one or more agonists of TRβ, or said one or more of Compounds 1-4, may be administered prior to, during, or after a surgical intervention, phototherapy, or ultrasound therapy. In some embodiments, said one or more agonists of TRβ, or said one or more of Compounds 1-4, may be coadministered with one or more of Pirfenidone, nintedanib, and/or a fibroblast growth factor receptor antagonist, and/or a collagenase, such as *Clostridium histolyticum* collagenase.

In some embodiments, administration of compounds 1-4, of compound 2, or of any of the compounds or compositions as disclosed herein results in a reduction in the expression of the Cola1, Col3a1, αSMA, and/or Galectin1 genes or any combination or product thereof in the subject to which said compound or composition is administered. In some embodiments, administration of compounds 1-4, of compound 2, or of any of the compounds or compositions as disclosed herein results in a reduction in the degree of fibrosis observable by histology, histochemistry, immunohistochemistry, or the like, and/or reduction s in the amount, accumulation, or distribution of type 1 collagen and/or hydroxyproline or any combination thereof in the subject to which said compound or composition is administered. In some embodiments, administration of compounds 1-4, of compound 2, or of any of the compounds or compositions as disclosed herein results in a reduction in total serum lipids, total serum cholesterol, total serum triglycerides, total liver lipids, total liver cholesterol, total liver triglycerides, or any combination thereof.

The methods described herein are further illustrated by the following examples.

EXAMPLE 1

DIO-NASH mice were acclimatized for 3 weeks, with pre-treatment liver biopsy samples collected prior to acclimatization. Mice were randomly assigned to one of five dosing groups, with 12 mice per group. Assigned dosages were: Compound 2 (low): 3 mg/kg; Compound 2 (high): 10 mg/kg; Compound 1: 10 mg/kg; and Elafibranor (30 mg·kg). One group was mock treated with vehicle only as a control. Dosage forms were administered orally once per day. After 8 weeks, animals were sacrificed and liver samples were taken. Liver samples were assayed for total liver hydroxyproline, and subjected to immunohistochemical observation for fibrosis stage as well as the extent of ColaI (Collagen Type Ia) staining. As shown in FIG. 1, Compound 2-treated animals show lower total liver hydroxyproline levels than control-treated or mock-treated animals. Since hydroxyproline is a significant component of collagen, and collagen is the most significant source of hydroxyproline in animal tissues, levels of hydroxyproline provide a reliable proxy for the presence of collagen in a sample.

Figure 2:
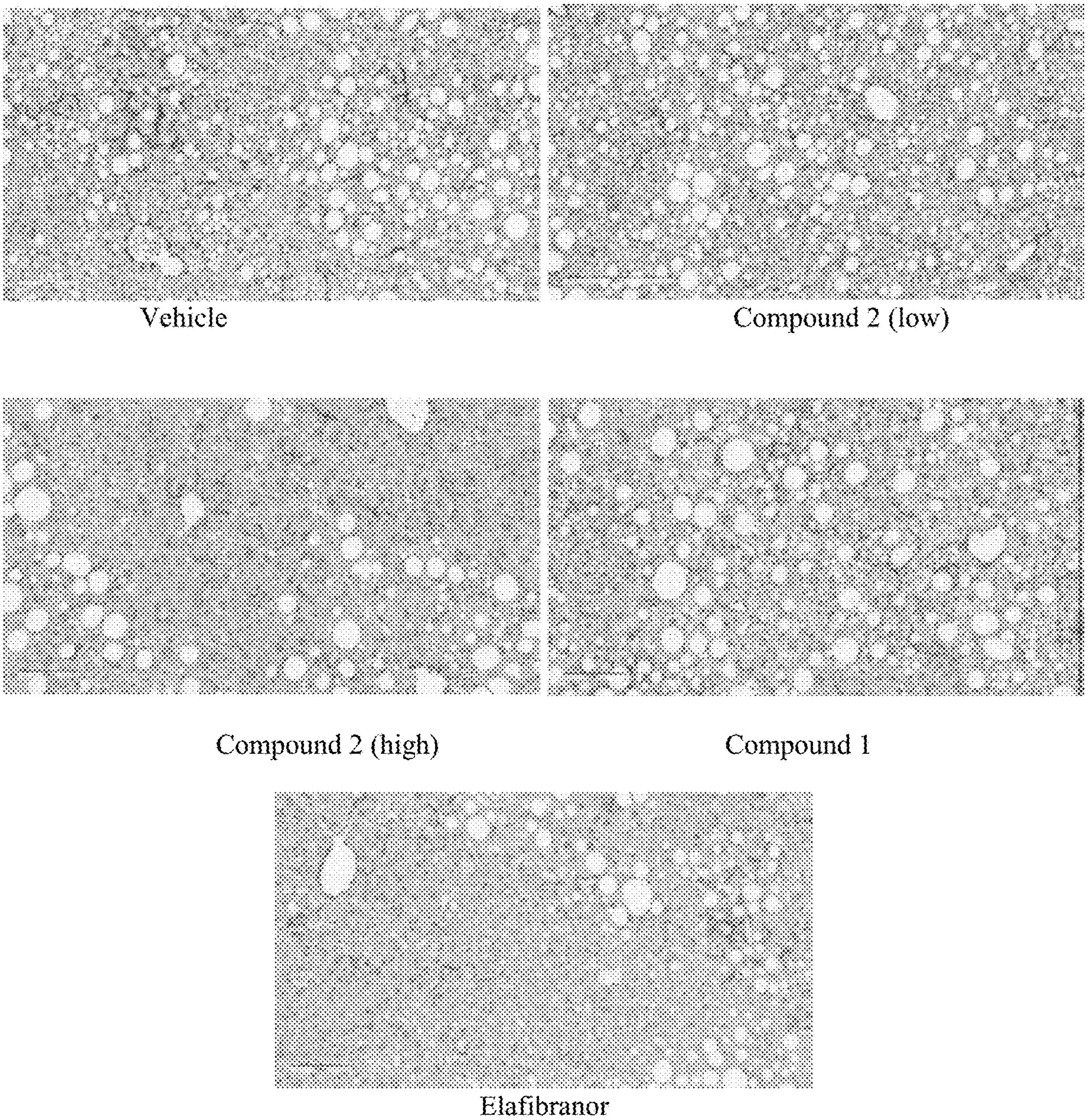
FIG. 2 shows representative images of liver stained with Picro-Sirius Red (to visualize collagen I and III deposition, red stain) at the end of the treatment period following 8 weeks of treatment with vehicle, low dose Compound 2 (see Example 1), high dose Compound 2 (see Example 1), Compound 1, or elafibranor (control) (magnification 10×, scale bar=200 μm).
Figure 3:
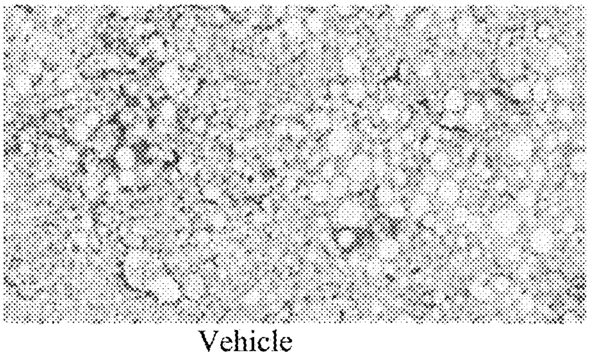
FIG. 3 shows representative images of liver stained with anti-type I collagen (col1a1) (Southern Biotech, Cat. 131001) at the end of the treatment period following 8 weeks of treatment with vehicle, low dose Compound 2 (see Example 1), high dose Compound 2 (see Example 1), Compound 1, or elafibranor (control) (magnification 20×, scale bar=100 μm).
Figure 3:
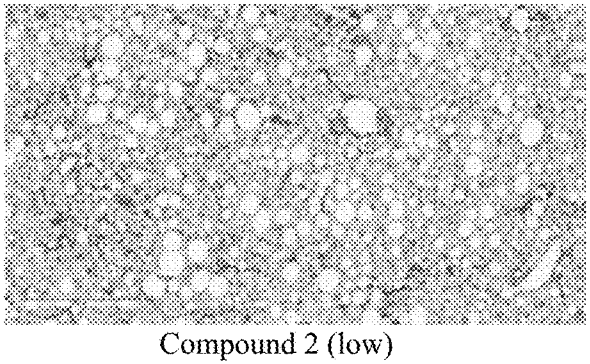
Figure 3:
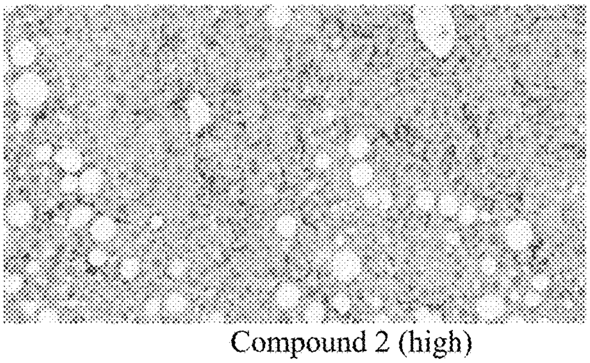
Figure 3:
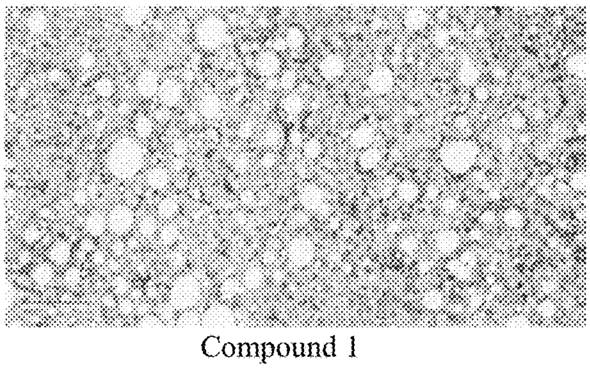
Figure 3:
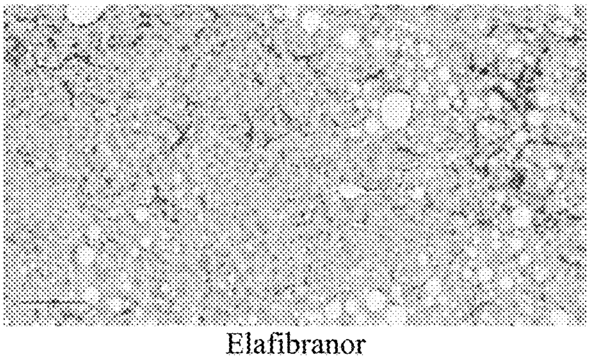
Figure 4:
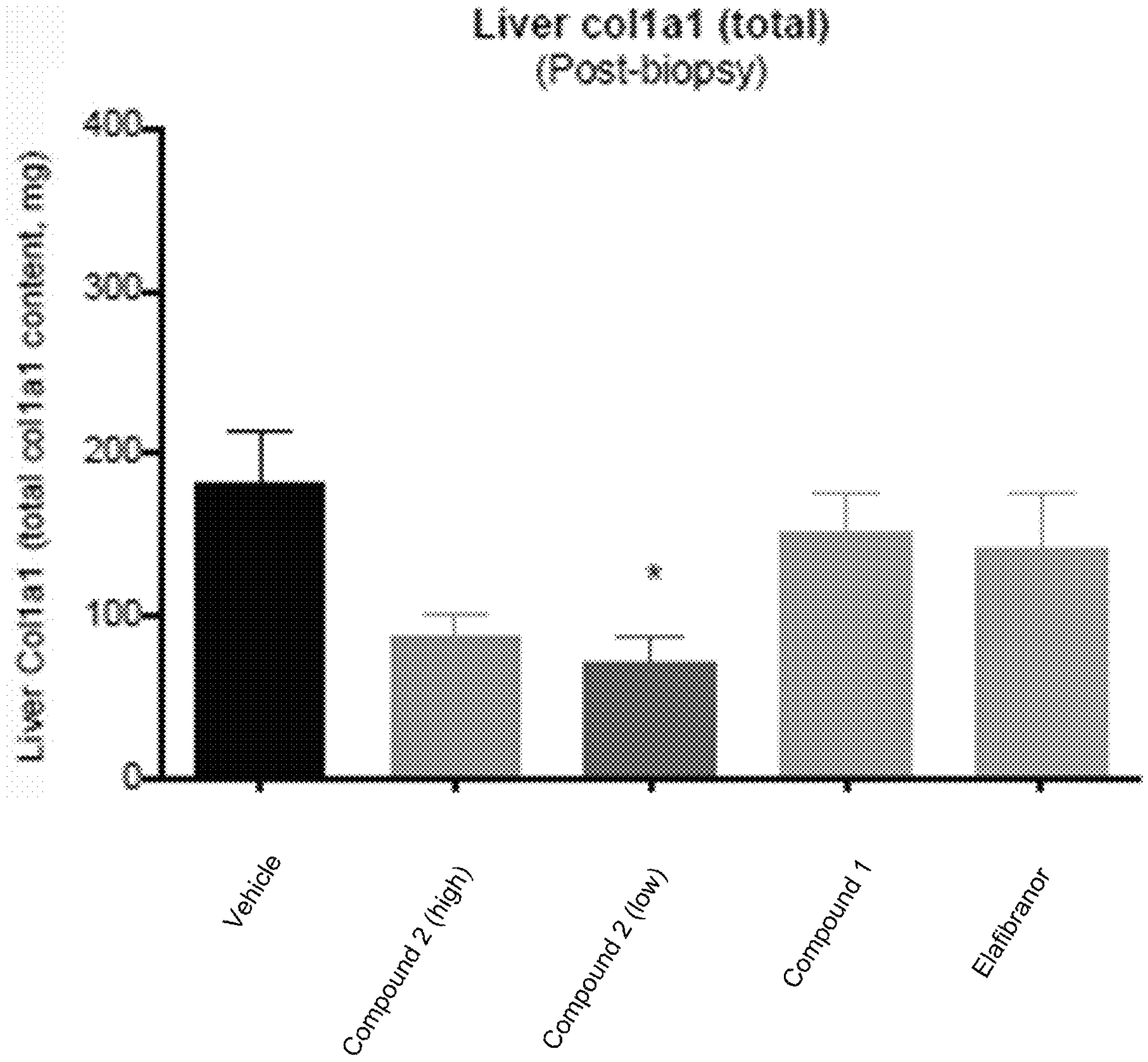
FIG. 4 shows total Liver ColA1 content post-biopsy following 8 weeks of treatment with vehicle, low dose Compound 2 (see Example 1), high dose Compound 2 (see Example 1), Compound 1, or elafibranor (control). Compound 2-treated animals show lower total liver ColA1 content than control-treated or mock-treated animals.
Figure 5:
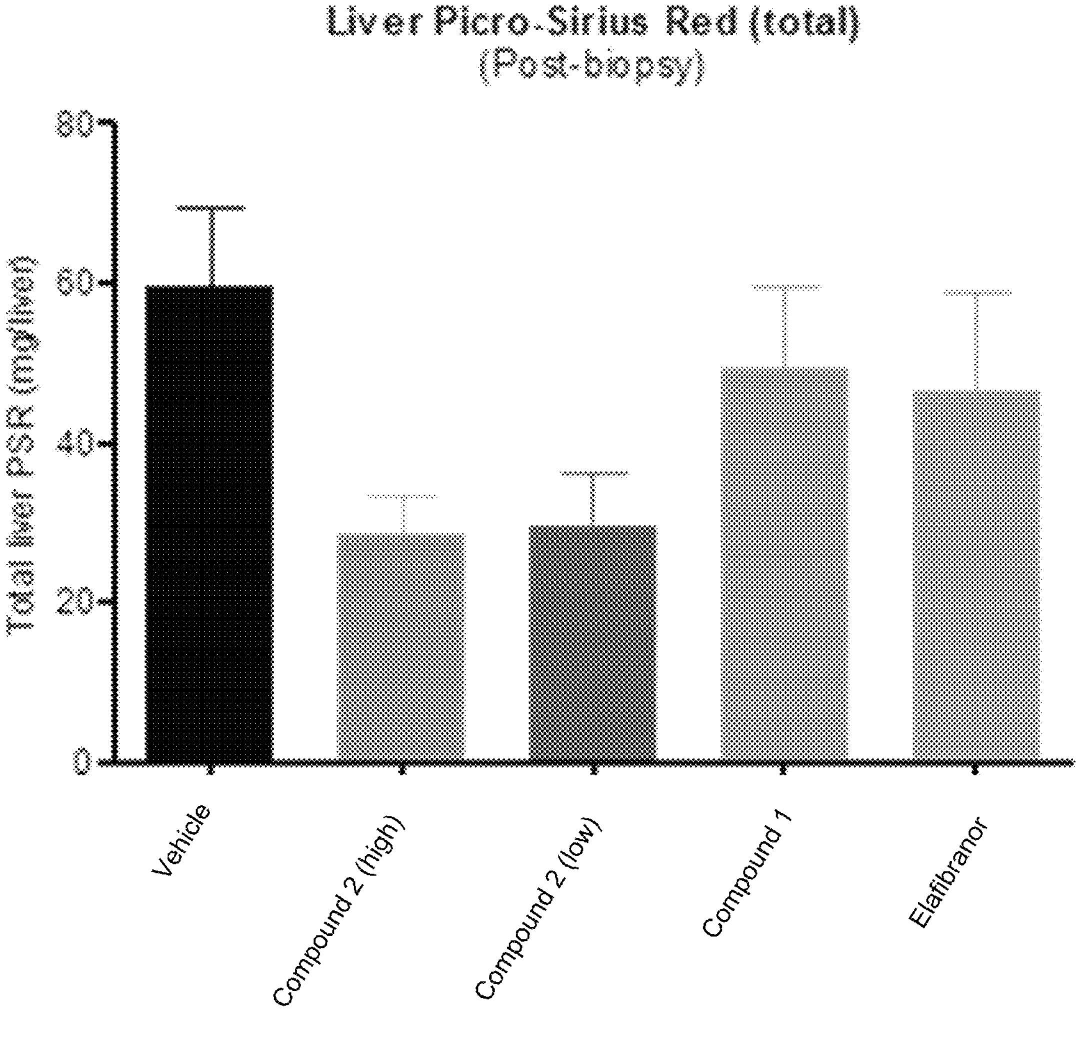
FIG. 5 shows liver Picro-Sirius Red (PSR) staining, post-biopsy, as determined by histological quantitative assessment following 8 weeks of treatment with vehicle, low dose Compound 2 (see Example 1), high dose Compound 2 (see Example 1), Compound 1, or elafibranor (control). Total (mg/liver) liver collagen 1 and 3 were determined by morphometry following Picro-Sirius Red staining. Liver sections from Compound-1-treated animals showed lower PSR staining than those from mock-treated animals; liver sections from Compound 2-treated animals showed lower PSR staining than control-treated or mock-treated animals. Data expressed as mean±SEM (n=11-12).

Terminal liver biopsy samples were also subjected to histochemical staining and immunohistochemical staining. Representative images of liver stained with Picro-Sirius Red (to visualize collagen I and III deposition, red stain) at the end of the treatment period following 8 weeks of treatment with vehicle, low dose Compound 2, high dose Compound 2, Compound 1, or elafibranor are shown in FIG. 2. As shown in FIG. 5, total liver collagen (mg/liver) 1 and 3 was determined by morphometry following Picro-Sirius Red staining. Liver sections from Compound-1-treated animals showed lower PSR staining than those from mock-treated animals; liver sections from Compound 2-treated animals showed lower PSR staining than control-treated or mock-treated animals. Representative images of liver stained with anti-type I collagen (col1a1) (Southern Biotech, Cat. 131001) at the end of the treatment period following 8 weeks of treatment with vehicle, low dose Compound 2, high dose Compound 2, Compound 1, or elafibranor are shown in FIG. 3. The extent of ColA1 content was calculated as the total liver ColA1 staining in terminal liver biopsy samples. As shown in FIG. 4, Compound 2-treated animals show lower total liver ColA1 content than control-treated or mock-treated animals.

Fibrosis scores were also calculated based on observation of terminal liver biopsy samples. Additionally, a higher proportion of animals treated with Compound 1 or Compound 2 showed a reduction in fibrosis score post-treatment than did mock treated animals. No Compound 2-treated animals showed increases in their fibrosis score post-treatment.

EXAMPLE 2

Pulmonary fibrosis is induced in healthy male Dunkin-Hartley guinea pigs by administering bleomycin intratracheally. Control subjects are developed by intratracheal administration of saline solution. After the establishment of pulomnary fibrosis in the bleomycin treated animals, test articles comprising any one of Compounds 1-4, or any other compound disclosed herein, are administered to each subject as appropriate for its formulation, daily or as appropriate, for 6-10 weeks. Unilateral lung biopsies are taken prior to the first administration of the test articles and again after sacrifice following the last administration of the test articles. Biopsy samples are analyzed as described in Example I, with the addition of immunohistochemical staining for type III collagen. Lungs from animals treated with the compounds disclosed herein, especially those animals treated with Compound 2, show reduced levels of hydroxyproline, decreased Collagen III staining, and decreased fibrosis score relative to the levels shown prior to the administration of the test articles. Mock treated animals show little or no reduction in fibrosis, hydroxyproline content, or Collagen III content.

EXAMPLE 2

Palmar fascia fibrosis is induced in nude mice by introducing fibroblasts from fibrotic cords of Dupuytren's disease patients as described in Stish, L. et al., BMC Musculoskelet. Disord. 16: 138-148 (2015) which is hereby incorporated by reference with respect to its description of the establishment of an animal model system for the study of palmar fascia fibrosis. After the establishment of palmar fascia fibrosis in the fibroblast treated animals, test articles comprising any one of Compounds 1-4, or any other compound disclosed herein, are administered to each subject as appropriate for its formulation, daily or as appropriate, for 6-10 weeks Unilateral forepaw biopsies are taken prior to the first administration of the test articles and again after sacrifice following the last administration of the test articles. Biopsy samples are analyzed as described in Example I, with the addition of immunohistochemical staining for type III collagen. Palmar fascia from animals treated with the compounds disclosed herein, especially those animals treated with Compound 2, show reduced levels of hydroxyproline, decreased Collagen III staining, and decreased fibrosis score relative to the levels shown prior to the administration of the test articles. Mock treated animals show little or no reduction in fibrosis, hydroxyproline content, or Collagen III content.

EXAMPLE 3

Hypertrophic skin lesions are induced in Sprague-Dawley Rats by subcutaneous injection of capsaicin as described in Wallengren, J. et al., Skin Pharm. Appl. Skin Physiol. 15(3): 154-165 (2002), which is hereby incorporated by reference with respect to its description of the induction of hypertrophic skin lesions in rats; or in C57BL or other appropriate strain mice by subcutaneous administration of $CCl_4$ and/or bleomycin, as described in Alonso-Merino et al., Proc. Nat. Acad. Sci. 113(24): E3451-60 (2016), which is incorporated herein for its disclosure of the induction of fibrotic skin lesions in mice. After the establishment of hypertrophic skin lesions in the capsaicin, $CCl_4$ and/or bleomycin treated animals, test articles comprising any one of Compounds 1-4, or any other compound disclosed herein, are administered to each subject animal as appropriate for its formulation, daily or as appropriate, for 6-10 weeks. Skin biopsies from the injection site are taken prior to the first administration of the test articles and again after sacrifice following the last administration of the test articles. Biopsy samples are analyzed as described in Example I, with the addition of immunohistochemical staining for type III collagen. Injection site skin samples from animals treated with the compounds disclosed herein, especially those animals treated with Compound 2, show reduced levels of hydroxyproline, decreased Collagen III staining, and decreased fibrosis score relative to the levels shown prior to the administration of the test articles. Mock treated animals show little or no reduction in fibrosis, hydroxyproline content, or Collagen III content.

EXAMPLE 4

Glucose-6-phosphatase-α deficient mice that manifest GSD-3- like hepatic symptoms, including hypercholesterolemia and hyperlipidemia (Agl−/−, see e.g. Liu, K. M. et al., Mol. Genet. Metabol. 111(4):467-76 (2014)) are treated with test articles comprising any one of Compounds 1-4, or any other compound disclosed herein, administered to each subject as appropriate for its formulation, daily or as appropriate, for 6-10 weeks. Liver biopsies are taken prior to the first administration of the test articles and again after sacrifice following the last administration of the test articles. Biopsy samples are analyzed as described in Example I. Liver samples from animals treated with the compounds disclosed herein, especially those animals treated with Compound 2, show reduced levels of hydroxyproline, decreased Collagen I staining, and decreased fibrosis score relative to the levels shown prior to the administration of the test articles. Mock treated animals show little or no reduction in fibrosis, hydroxyproline content, or Collagen I content.

EXAMPLE 5

Phosphorylase kinase deficient mice that manifest GSD-8/9- like hepatic symptoms, including hypercholesterolemia and hyperlipidemia (PhKc−/−, see, e.g., Varsanyi, M. et al., Biochem. Genet. 18(3-4):247-61 (1980)), are treated with test articles comprising any one of Compounds 1-4, or any other compound disclosed herein, administered to each subject as appropriate for its formulation, daily or as appropriate, for 6-10 weeks. Liver biopsies are taken prior to the first administration of the test articles and again after sacrifice following the last administration of the test articles. Biopsy samples are analyzed as described in Example I. Liver samples from animals treated with the compounds disclosed herein, especially those animals treated with Compound 2, show reduced levels of hydroxyproline, decreased Collagen I staining, and decreased fibrosis score relative to the levels shown prior to the administration of the test articles. Mock treated animals show little or no reduction in fibrosis, hydroxyproline content, or Collagen I content.

EXAMPLE 6

Figure 6:
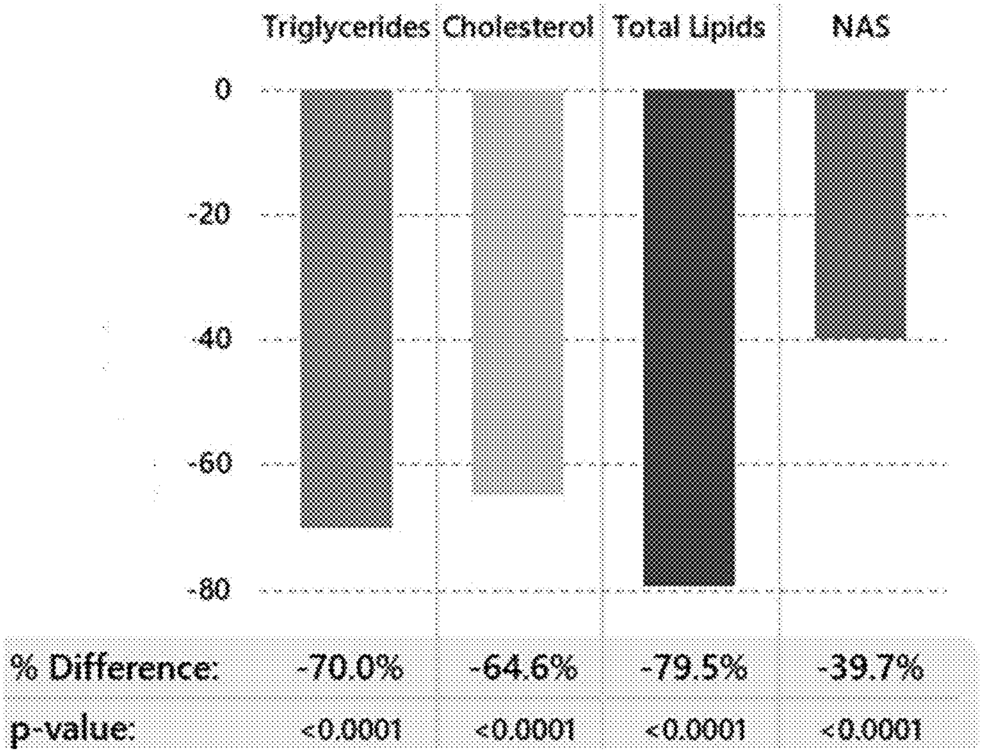
FIG. 6 shows the percent reduction in total liver triglycerides, cholesterol, and lipids as well as the percent reduction in NAS for Compound 2-treated animals vs. vehicle-treated controls following 8 weeks of dosing with Compound 2 in a diet-induced mouse model of NASH (See Example 6).

Compound 2 was evaluated in a diet-induced NASH mouse model (See, e.g., Hansen, H. et al., Drug Discovery Today 22(17): 1701-1718 (2017) which is hereby incorporated by reference with respect to its disclosure of diet-induced, genetic, chemical, and other NASH mouse models). Diet-driven NASH in this model does not rely on chemical/toxin effects to generate steatohepatitis/fibrosis. Animals were biopsied pre-study, and only animals with NASH and fibrosis were selected for study. Selected animals were acclimatized and randomized, with experimental groups of 11-12 animals per cohort receiving oral dosing of compound 2 according to the following schedules. Daily dosing for 8 weeks; or daily dosing for week 0-1 followed by weekly dosing for weeks 2-8. At week 8, animals were sacrificed and tissues analyzed. Plasma enzymes (P-ALT (alanine aminotransferase) and P-AST (aspartate aminotransferase)), total plasma triglycerides, and total plasma cholesterol were measured, and terminal necropsy of each liver was carried out, assaying total liver biochemistry including total liver triglycerides, and total liver cholesterol, as well as histological evaluation of NAFLD activity score (done pre- and post-treatment), fibrosis stage (also done pre- and post-treatment), steatosis, Col1a1 level, and galactin-3 level. Tissue samples were preserved for characterization using RNAseq; RNAseq was used to determine expression levels for genes showing differential expression in compound 2-treated vs. vehicle treated animals and/or genes known to be implicated in fibrosis. Significant reductions in liver triglycerides and cholesterol were observed in treatment groups relative to untreated controls. As shown in FIG. 6, total lipid content in the liver was reduced by approximately 80%, with similar reductions in plasma lipids and significant improvements in NAS scores. No significant toxicity was observed.

Figure 7:
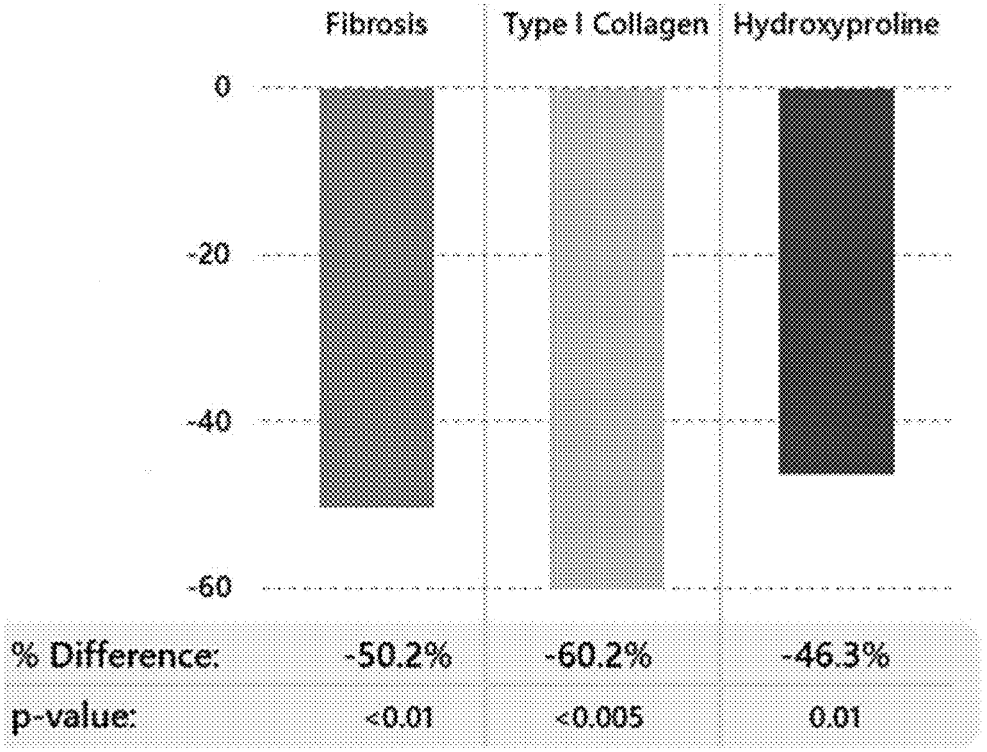
FIG. 7 shows the percent reduction in liver fibrosis for Compound 2-treated animals vs. vehicle-treated controls following 8 weeks of dosing with Compound 2 in a diet-induced mouse model of NASH (See Example 6). Liver fibrosis is assessed in terms of fibrosis score, the level of Type I collagen present, and the level of hydroxyproline present in post-treatment liver samples.
Figure 8:
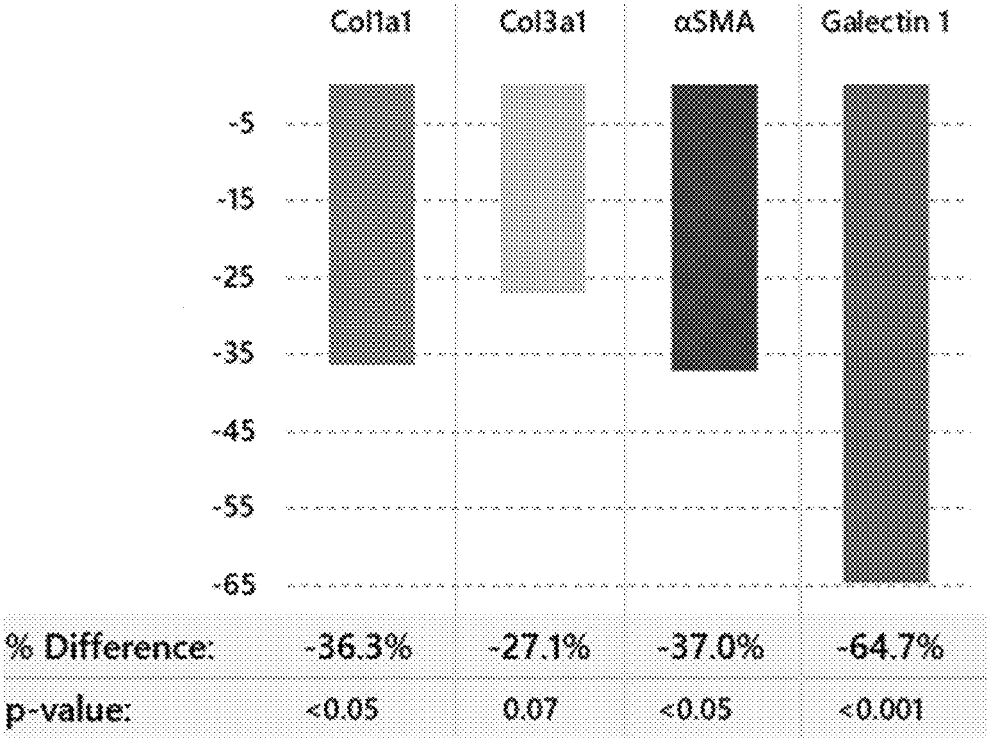
FIG. 8 shows the percent reduction in pro-fibrogenic gene expression for Compound 2-treated animals vs. vehicle-treated controls following 8 weeks of dosing with Compound 2 in a diet-induced mouse model of NASH (See Example 6). Pro-fibrogenic gene expression is assessed in terms of the levels of expression of Cola1, Col3a1, αSMA, and Galectin 1 in post-treatment liver samples.

As shown in FIG. 7, significant reductions in fibrosis, type 1 collagen deposition, and hydroxyproline (50.2%, 60.2%, and 46.3%, respectively) were also seen relative to pre-treatment samples. Post-treatment, expression of pro-fibrotic genes Col1a1, Col3a1, αSMA, and Galectin 1 were reduced by 36.3%, 27.1%, 37%, and 64.7%, respectively (FIG. 8), confirming the results observed by histology. Thus, 8-week dosing with compound 2 resulted in marked improvements in histological, biochemical, and genetic markers related to steatosis, fibrosis, and non-alcoholic steatohepatitis in a diet-induced NASH model.

With respect to the use of substantially any plural and/or singular terms herein, those having skill in the art can translate from the plural to the singular and/or from the singular to plural as is appropriate to the context and/or application. The various singular/plural permutations can be expressly set forth herein for sake of clarity.

It will be understood by those within the art that, in general, terms used herein, and especially in the appended claims (for example, bodies of the appended claims) are generally intended as "open" terms (for example, the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims can contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (for example, "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (for example, the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (for example, "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (for example, "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible sub-ranges and combinations of sub-ranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into sub-ranges as discussed above. Finally, as will be understood by one skilled in the art, a range includes each individual member. Thus, for example, a group having 1-3 articles refers to groups having 1, 2, or 3 articles. Similarly, a group having 1-5 articles refers to groups having 1, 2, 3, 4, or 5 articles, and so forth.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A method of treating fibrosis, a fibrotic condition or a fibrotic symptom in a subject in need thereof comprising administering to said subject in need thereof a compound having the structure:

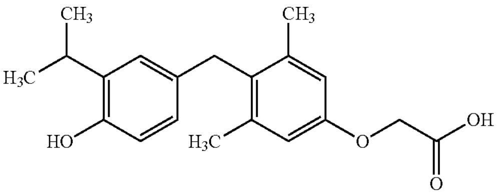 [SMILES: Cc1cc(OCC(=O)O)cc(C)c1Cc1ccc(O)c(C(C)C)c1]

or a pharmaceutically acceptable salt thereof.

2. The method of claim 1, wherein said subject has one or more fibrotic conditions selected from glycogen storage disease type III (GSD III), glycogen storage disease type VI (GSD VI), glycogen storage disease type IX (GSD IX), non-alcoholic steatohepatitis (NASH), cirrhosis, hepatitis, scleroderma, alcoholic fatty liver disease, atherosclerosis, asthma, cardiac fibrosis, organ transplant fibrosis, muscle fibrosis, pancreatic fibrosis, bone-marrow fibrosis, liver fibrosis, cirrhosis of liver and gallbladder, fibrosis of the spleen, pulmonary fibrosis, idiopathic pulmonary fibrosis, diffuse parenchymal lung disease, idiopathic interstitial fibrosis, diffuse interstitial fibrosis, interstitial pneumonitis, desquamative interstitial pneumonia, respiratory bronchiolitis, interstitial lung disease, chronic interstitial lung disease, acute interstitial pneumonitis, hypersensitivity pneumonitis, nonspecific interstitial pneumonia, cryptogenic organizing pneumonia, lymphocytic interstitial pneumonia, pneumoconiosis, silicosis, emphysema, interstitial fibrosis, sarcoidosis, mediastinal fibrosis, cardiac fibrosis, atrial fibrosis, endomyocardial fibrosis, renal fibrosis, chronic kidney disease, Type II diabetes, macular degeneration, keloid lesions, hypertrophic scar, nephrogenic systemic fibrosis, injection fibrosis, complications of surgery, fibrotic chronic allograft vasculopathy and/or chronic rejection in transplanted organs, fibrosis associated with ischemic reperfusion injury, post-vasectomy pain syndrome, fibrosis associated with rheumatoid arthritis, arthrofibrosis, Dupuytren's disease, dermatomyositis-polymyositis, mixed connective tissue disease, fibrous proliferative lesions of the oral cavity, fibrosing intestinal strictures, Crohn's disease, glial scarring, leptomeningeal fibrosis, meningitis, systemic lupus erythematosus, fibrosis due to radiation exposure, fibrosis due to mammary cystic rupture, myelofibrosis, retroperitoneal fibrosis, progressive massive fibrosis, or symptoms or sequelae thereof, or other diseases or conditions resulting in the excessive deposition of extracellular matrix components, such as collagen, which may be affected by interventions within the TRβ pathway, or any combination thereof.

3. The method of claim 1, wherein said fibrosis, fibrotic condition or fibrotic symptom is a primary fibrosis.

4. The method of claim 1, wherein said fibrosis, fibrotic condition or fibrotic symptom is secondary to another condition.

5. The method of claim 1, wherein said fibrosis, fibrotic condition or fibrotic symptom comprises one or more of scleroderma, atherosclerosis, cardiac fibrosis, organ transplant fibrosis, muscle fibrosis, pancreatic fibrosis, bone-marrow fibrosis, liver fibrosis, fibrosis of the spleen, pulmonary fibrosis, idiopathic pulmonary fibrosis, idiopathic interstitial fibrosis, diffuse interstitial fibrosis, interstitial lung disease, chronic interstitial lung disease, pneumoconiosis, silicosis, interstitial fibrosis, sarcoidosis, mediastinal fibrosis, cardiac fibrosis, atrial fibrosis, endomyocardial fibrosis, renal fibrosis, macular degeneration, keloid lesions, hypertrophic scar, nephrogenic systemic fibrosis, injection fibrosis, fibrotic complications of surgery, fibrotic chronic allograft vasculopathy, fibrosis associated with ischemic reperfusion injury, arthrofibrosis, Dupuytren's disease, fibrous proliferative lesions of the oral cavity, fibrosing intestinal strictures, glial scarring, leptomeningeal fibrosis, fibrosis due to radiation exposure, fibrosis due to mammary cystic rupture, myelofibrosis, retroperitoneal fibrosis, progressive massive fibrosis or any combination thereof.

6. The method of claim 1, wherein said fibrosis, fibrotic condition or fibrotic symptom is secondary to one or more of glycogen storage disease type III (GSD III), glycogen storage disease type VI (GSD VI), glycogen storage disease type IX (GSD IX), non-alcoholic steatohepatitis (NASH), cirrhosis, hepatitis, scleroderma, alcoholic fatty liver disease, atherosclerosis, asthma, cirrhosis of the gallbladder, diffuse parenchymal lung disease, interstitial pneumonitis, desquamative interstitial pneumonia, respiratory bronchiolitis, interstitial lung disease, chronic interstitial lung disease, acute interstitial pneumonitis, hypersensitivity pneumonitis, nonspecific interstitial pneumonia, cryptogenic organizing pneumonia, lymphocytic interstitial pneumonia, emphysema, chronic kidney disease, Type II diabetes, macular degeneration, chronic rejection in transplanted organs, post-vasectomy pain syndrome, rheumatoid arthritis, dermatomyositis-polymyositis, mixed connective tissue disease, Crohn's disease, meningitis, systemic lupus erythematosus, or symptoms or sequelae thereof, or other diseases or conditions resulting in the excessive deposition of extracellular matrix components, such as collagen, which may be affected by interventions within the TRβ pathway, or any combination thereof.

7. The method of claim 1, wherein said fibrosis, fibrotic condition or fibrotic symptom is a symptom or sequela of GSD III, GSD VI, GSD IX, Non Alcoholic Steatohepatitis, cirrhosis of the liver or pancreas, Dupuytren's disease, scleroderma, idiopathic pulmonary fibrosis, or alcoholic fatty liver disease, or any combination thereof.

8. The method of claim 1, comprising administering a composition comprising said compound and one or more pharmaceutically acceptable excipients.

9. The method of claim 1, wherein said composition is formulated for oral, intravenous, intraarterial, intestinal, rectal, vaginal, nasal, pulmonary, topical, intradermal, transdermal, transbuccal, translingual, sublingual, or ophthalmic administration, or any combination thereof.

10. The method of claim 1, wherein said subject shows abnormal or excessive deposition of collagen.

11. The method of claim 1, wherein said subject shows abnormal or excessive deposition of collagen type 1.

12. The method of claim 1, wherein said subject shows abnormal or excessive deposition of collagen type 1a.

13. The method of claim 1, wherein said subject shows abnormal or excessive deposition of collagen type III.

14. The method of claim 1, wherein said administration of said compound results in the prevention, amelioration, or cure of said fibrosis, fibrotic condition, or fibrotic symptom.

15. The method of claim 1, wherein said administration of said compound results in the reduction in the amount of extracellular matrix proteins present in one or more tissues of said subject.

16. The method of claim 1, wherein said administration of said compound results in the reduction in the amount of collagen present in one or more tissues of said subject.

17. The method of claim 1, wherein said administration of said compound results in the reduction in the amount of Type I, Type Ia, or Type III collagen present in one or more tissues of said subject.

* * * * *